US008148080B2

(12) United States Patent
Nakamura et al.

(10) Patent No.: US 8,148,080 B2
(45) Date of Patent: Apr. 3, 2012

(54) GENE AND PROTEIN RELATING TO HEPATOCELLULAR CARCINOMA AND METHODS OF USE THEREOF

(75) Inventors: Yusuke Nakamura, Yokohama (JP); Yoichi Furukawa, Kawasaki (JP)

(73) Assignee: Oncotherapy Science, Inc., Kanagawa (JP)

( * ) Notice: Subject to any disclaimer, the term of this patent is extended or adjusted under 35 U.S.C. 154(b) by 0 days.

(21) Appl. No.: 12/727,370

(22) Filed: Mar. 19, 2010

(65) Prior Publication Data

US 2010/0248240 A1    Sep. 30, 2010

Related U.S. Application Data

(60) Division of application No. 10/788,847, filed on Feb. 27, 2004, now Pat. No. 7,767,392, which is a continuation-in-part of application No. PCT/JP02/09876, filed on Sep. 25, 2002.

(60) Provisional application No. 60/324,261, filed on Sep. 25, 2001, provisional application No. 60/391,666, filed on Jun. 26, 2002, provisional application No. 60/450,644, filed on Feb. 28, 2003.

(30) Foreign Application Priority Data

Aug. 23, 2002   (CA) ..................... 2399569

(51) Int. Cl.
   *C12Q 1/68*   (2006.01)
(52) U.S. Cl. ..................................... 435/6.14
(58) Field of Classification Search .................. None
   See application file for complete search history.

(56) References Cited

U.S. PATENT DOCUMENTS

| | | | |
|---|---|---|---|
| 6,783,961 B1 | 8/2004 | Edwards et al. | |
| 2003/0157531 A1 | 8/2003 | Costa et al. | |
| 2004/0235018 A1 | 11/2004 | Nakamura et al. | |
| 2009/0035303 A1 | 2/2009 | Nakamura et al. | |
| 2009/0035771 A1 | 2/2009 | Nakamura et al. | |
| 2009/0142344 A1 | 6/2009 | Nakamura et al. | |
| 2009/0191181 A1 | 7/2009 | Nakamura et al. | |
| 2010/0184088 A1 | 7/2010 | Nakamura | |

FOREIGN PATENT DOCUMENTS

| | | |
|---|---|---|
| EP | 1033401 | 9/2000 |
| EP | 1591448 | 11/2005 |
| WO | WO-99/39200 | 8/1999 |
| WO | WO-00/17355 | 3/2000 |
| WO | WO-00/44900 | 8/2000 |
| WO | WO-0129221 | 4/2001 |
| WO | WO-0153456 | 7/2001 |
| WO | WO-02059377 | 8/2002 |
| WO | WO-02090578 | 11/2002 |
| WO | WO-02092002 | 11/2002 |
| WO | WO-03010180 | 2/2003 |
| WO | WO-03/027143 A2 | 4/2003 |
| WO | WO-03/027143 A3 | 4/2003 |
| WO | WO-03/027322 A2 | 4/2003 |
| WO | WO-03/027322 A3 | 4/2003 |
| WO | WO-03027143 A2 | 4/2003 |
| WO | WO-2004076623 | 9/2004 |
| WO | WO-2008152816 | 12/2008 |

OTHER PUBLICATIONS

Hamamoto, R. et al., "SMYD3 encodes a histone methyltransferase involved in the proliferation of cancer cells", Nature Cell Biol., 2004, vol. 6: pp. 731-740.*
Genbank entry for AB057595, Aug. 18, 2004, 1 page.*
Ansieu et al., *J. Bio. Chem.*, 277(7):4906-4910 (2002).
Aratani, et al., *Mol. Cell. Biol.*, 21(14):4460-4469 (2001).
Brummelkamp, et al., *Sci.*, 296(5567):550-553 (2002).
Carnici et al., "Normalization and subtraction of cap-trapper-selected cDNAs to prepare full-length cDNA libraries for rapid discovery of new genes", *Genome Res.*, 10(10):1617-1630 (2000).
Cerione, et al., *Curr. Opin. Cell Biol.*, 8(2):216-222 (1996).
Chardin, et al., *Nature*, 384(6608):481-484 (1996).
Chiosis et al., *BioOrg. Med. Chem.*, 10(11):3555-3564 (2002).
Choi, et al., *Can.*, 79(10):1879-1883 (1997).
Cukierman, et al., *Sci.*, 270(5244):1999-2002 (1995).
Database Accession No. AAA08583, Jul. 2000.
Database Accession No. BE747972, Sep. 2000.
Database Accession No. AK000206, Feb. 22, 2000.
Database Accession No. BG773806, May 16, 2001.
Database Uniport 7.2, run on Sep. 21, 2006.
Delwel, et al., Mot Cell. Biol., 13(7):4291-4300 (1993).
Du et al., "Hypermethylation in Human Cancers of the *RIZI* Tumor Suppressor Gene, a Member of a Histone/Protein Methyltransferase Superfamily", *Can. Res.*, 61:8094-8099 (2001).
Echeverri et al., "siRNA Design: It's All in the Algorithm", Applied BioSystems (Internet Artcile), www.ambion.com, 11:3 (2004).
Eck et al., "Gene-based therapy", in Goodman & Gilman's the Pharmacological Basis of Therapeutics, Ninth Edition, Chapter 5, pp. 77-101 (1996).
Elbashir, et al., *Nature*, 411(6836):494-498 (2001).
EMBL Accession No. AK024733, Sep. 29, 2000.
EMBL Accession No. AL557360, Feb. 11, 2001.
Fantin et al., Can. Cell., 2(1):29-42 (2002).
Firestein et al., "Set domain-dependent regulation of transcriptional silencing and growth control by SUV39H1, a mammalian ortholog of *Drosophila* Su(var)3-9", *Mol. Cell. Biol.*, 20(7):4900-4909 (2000).
Fu, et al., *J. Viral.*, 67(12):6965-6972 (1993).
Gelmetti, et al., *Mol. Cell. Biol.*, 18(12):7185-7191 (1998).
GenBank Accession No. AACO2474.1, Feb. 1998.
Genbank Accession No. AAG66728:Nov. 26, 2001.
GenBank Accession No. AB057596, May 14, 2002.
Genbank Accession No. BC031010:Jun. 13, 2002.
Ghanem, et al., *Can.*, 92(12):3120-3129 (2001).
Golub, et al., *Sci.*, 286(5439):531-537 (1999).
Gross, et al., *EMBO J.*, 15(8):1961-1870 (1996).

(Continued)

*Primary Examiner* — Michael Burkhart
(74) *Attorney, Agent, or Firm* — Mintz. Levin, Cohn, Ferris, Glovsky and Popeo, P.C.; Ingrid A. Beattie; Cynthia A. Kozakiewicz

(57) ABSTRACT

The present invention provides a novel human gene ZNFN3A1 whose expression is markedly elevated in a great majority of HCCs compared to corresponding non-cancerous liver tissues. The gene encodes a protein having a zinc finger domain as well as a SET domain and has been found to form a regulatory complex with RNA helicase and RNA polymerase.

1 Claim, 25 Drawing Sheets

OTHER PUBLICATIONS

Hamamoto, et al., *Jpn. J. Can. Res.*, 92(Supplement):117(#208), and English translation, (2001).
Hamamoto, et al., *94th Annual Mtg. of the Am. Assoc. for Can. Res.*, 44:54(#236), and English translation, (2003).
Hamamoto, et al., *94th Annual Mtg. of the Am. Assoc. for Can. Res.*, 44(Second Edition):47(#236),and English translation, (2003).
Hamamoto, et al., *Jpn. Assoc. Mot. Target Thar. Can.*, 36(#SY-1), and English translation, (2002).
Hamamoto, et al., *Jpn. J. Can. Res.*, 286(#3339-0P), and English translation, (2003).
Hamamoto, et al., *Jpn. J. Can. Res.*, 93(Supplement):78(#2032), and English translation, (2002).
Hamamoto, et al., *Proceedings of the Am. Assoc. for Can. Res. Ann.*, 43:13(#63), and English translation, (2002).
Hammond, et al., *Nature*, 404(6775):293-296 (2000).
Hannon, et al., *Nature*, 418(6894):244-251 (2002).
Herbst, et al., *Can.*, 94(5):1593-1611 (2002).
Hermouet, et al., *Proc. Natl. Acad. Sci. USA*, 88(23):10455-10459 (1991).
Ito, et al., *Br. J. Can.*, 84(10):1377-1383 (2001).
Jackson, et al., *Trends Biochem. Sci.*, 25(10):489-495 (2000).
Kato, et al., *Jpn. J. Can. Res.*, 93(Supplement):78(2033), and English translation, (2002).
Katoh et al., "Molecular Cloning and Characterization of Strabismus 2 (STB2)", *Intl. J. Oncol.*, 20(5):993-998 (2002).
Katoh et al., "Strabismus (STB)/Vang-like (VANGL) Gene Family (Review)", *Int. J. MOI. Med.*, 10(1):11-15 (2002).
Kennell et al., *Proc. Nucleic Acid Res. Mol. Biol.*, 11:259-301 (1971).
Kibar, et al., *Nat. Genet.*, 28(3):251-255 (2001).
Lüking, et al., *Crit. Rev. Biochem. Mot Biol.*, 33(4):259-296 (1998).
Lutterbach, et al., *Mot. Cell. Biol.*, 18(12):7176-7184 (1998).
Lyons, et al., *Sci.*, 249(4969):655-659 (1990).
Masselink, el al., *Oncogene*, 19(12):1538-1546 (2000).
Mendelsohn, et al., *Oncogene*, 19(56):6550-6565 (2000).
Miyagishi, et al., *Nat. Biotechnol.*, 19:497-500 (2002).
Miyaki, et al., *Int. J. Cancer*, 85(4):518-522 (2000).
Mochizuki, et al., *Gene*, 181(1-2):39-43 (1996).
Moss, et al., *J. Biol. Chem.*, 270(21):12327-12330 (1995).
Nakajima, et al., *Cell*, 90(6):1107-1112 (1997).
Ngo et al., The Protein Folding Problem and Tertiary Structure Prediction , 492-495 (1994).
Okabe, et al., *Cancer Res.*, 61(5):2129-2137 (2001).
Orkin et al., "Report and recommendations of the panel to assess the NIH investment in research on gene therapy", pp. 1-41 (1995).
Pace, et al., *Proc. Natl. Acad. Sci. USA*, 88(16):7031-7035 (1991).
Perou, et al., *Nature*, 406(6797):747-752 (2000).
Randazzo, et al., *Proc. Natl. Acad. Sci. USA*, 97(8):4011-4016 (2000).
Rea et al., "Regulation of chromatin structure by site-specific histone H3 methyltransferase", *Nature*, 406:593-599 (2000).
Rozovskaia et al., "Self-association of the SET domains of human ALL-1 and of *Drosophila* TRITHORAX and ASH1 proteins", *Oncogene*, 19(3):351-357 (2000).
Rudinger et al., Peptide Hormones: University Park Press, 1-7 (1976).
Sharp, P.A., *Genes Dev.*, 13(2):139-141 (1999).
Shiff et al., J. Clin. Invest., 96(1):491-503 (1995).
Stockand et al., "S-Adenosyl-[-homocysteine Hydolase Regulates Aldosterone-induced $Na^=$ Transport", *J. Bio. Chem.*, 274(6):3842-3850 (1999).
Strahl et al., "Methylation of histone HS at lysine 4 is highly conserved and correlates with transcriptionally active nuclei in *Tetrahymena*", *PNAS*, 96(26):14967-14972 (1999).
Strausberg et al., "Generation and initial analysis of more than 15, 000 full-length human and mouse cDNA sequences", *PNAS*, 99(26):16899-16903 (2002).
Tanaka, et al., *Biochim. Biophys. Acta*, 1536(1):1-12 (2001).
Tang, et al., *Mol. Cell. Biol.*, 19(5):3540-3550 (1999).
Tanner, et al., *Mot. Cell*, 8(2):251-262 (2001).
Verma et al., "Gene therapy—promises, problems and prospects", *Nature*, 389(6648):239-242 (1997).
von Marschall, et al., *Gut.*, 48(1):87-96 (2001).
Westermarck, et al., *EMBO J.*, 21(3):451-460 (2002).
Wolff, et al., *Develop.*, 125(6):1149-1159 (1998).
Yagyu, et al., *Jpn. J. Can. Res.*, 92(Supplement):118(209), and English translation, (2001).
Yagyu, et al., *Mt. J. Oncol.*, 20(6):1173-1178 (2002).
Ying, et al., *Biochem. Biophys. Res. Commun.*, 286(2):394-400 (2001).

* cited by examiner

```
ZNFN3A1  :   1 MEPLKVEKFATANRGNGLRAVTPLRPGELLFRSDPLAYTVCKGSRGVVCDRCLLGKEKLM  60
               ME LKVEKF TANRGNGLRAV PLRPGELLFRSDPLAYTVCKGSRGVVCDRCLLGKEKLM
AK010447:   1 MEALKVEKFTTANRGNGLRAVAPLRPGELLFRSDPLAYTVCKGSRGVVCDRCLLGKEKLM  60

ZNFN3A1  :  61 RCSQCRVAKYCSAKCQKKAWPDHKRECKCLKSCKPRYPPDSVRLLGRVVFKLMDGAPSES 120
               RCSQCR AKYCSAKCQKKAWPDH+REC CLKSCKPRYPPDSVRLLGRV+ KLMD PSES
AK010447:  61 RCSQCRIAKYCSAKCQKKAWPDHRRECSCLKSCKPRYPPDSVRLLGRVIVKLMDEKPSES 120

ZNFN3A1  : 121 EKLYSFYDLESNINKLTEDKKEGLRQLVMTFQHFMREEIQDASQLPPAFDLFEAFAKVIC 180
               EKLYSFYDLESNI+KLTEDKKEGLRQL MTFQHFMREEIQDASQLPP+FDLFEAFAKVIC
AK010447: 121 EKLYSFYDLESNISKLTEDKKEGLRQLAMTFQHFMREEIQDASQLPPSFDLFEAFAKVIC 180

ZNFN3A1  : 181 NSFTICNAEMQEVGVGLYPSISLLNHSCDPNCSIVFNGPHLLLRAVRDIEVGEELTICYL 240
               NSFTICNAEMQEVGVGLYPS+SLLNHSCDPNCSIVFNGPHLLLRAVR+IE GEELTICYL
AK010447: 181 NSFTICNAEMQEVGVGLYPSMSLLNHSCDPNCSIVFNGPHLLLRAVREIEAGEELTICYL 240

ZNFN3A1  : 241 DMLMTSEERRKQLRDQYCFECDCFRCQTQDKDADMLTGDEQVWKEVQESLKKIEELKAHW 300
               DMLMTSEERRKQLRDQYCFECDC RCQTQDKDADMLTGDEQ+WKEVQESLKKIEELKAHW
AK010447: 241 DMLMTSEERRKQLRDQYCFECDCIRCQTQDKDADMLTGDEQIWKEVQESLKKIEELKAHW 300

ZNFN3A1  : 301 KWEQVLAMCQAIISSNSERLPDINIYQLKVLDCAMDACINLGLLEEALFYGTRTMEPYRI 360
               KWEQVLA+CQAII+SNS RLPDINIYQLKVLDCAMDACINLG+LEEALFY  RTMEPYRI
AK010447: 301 KWEQVLALCQAIINSNSNRLPDINIYQLKVLDCAMDACINLGMLEEALFYAMRTMEPYRI 360

ZNFN3A1  : 361 FFPGSHPVRGVQVMKVGKLQLHQGMFPQAMKNLRLAFDIMRVTHGREHSLIEDLILLLEE 420
               FFPGSHPVRGVQVMKVGKLQLHQGMFPQAMKNLRLAFDIM+VTHGREHSLIEDLILLLEE
AK010447: 361 FFPGSHPVRGVQVMKVGKLQLHQGMFPQAMKNLRLAFDIMKVTHGREHSLIEDLILLLEE 420

ZNFN3A1  : 421 CDANIRAS 428    (SEQ ID NO: 1)
               CDANIRAS        (SEQ ID NO: 81)
AK010447: 421 CDANIRAS 428    (SEQ ID NO: 82)
```

FIG.2B

FIG.3A   FIG.3B   FIG.3C
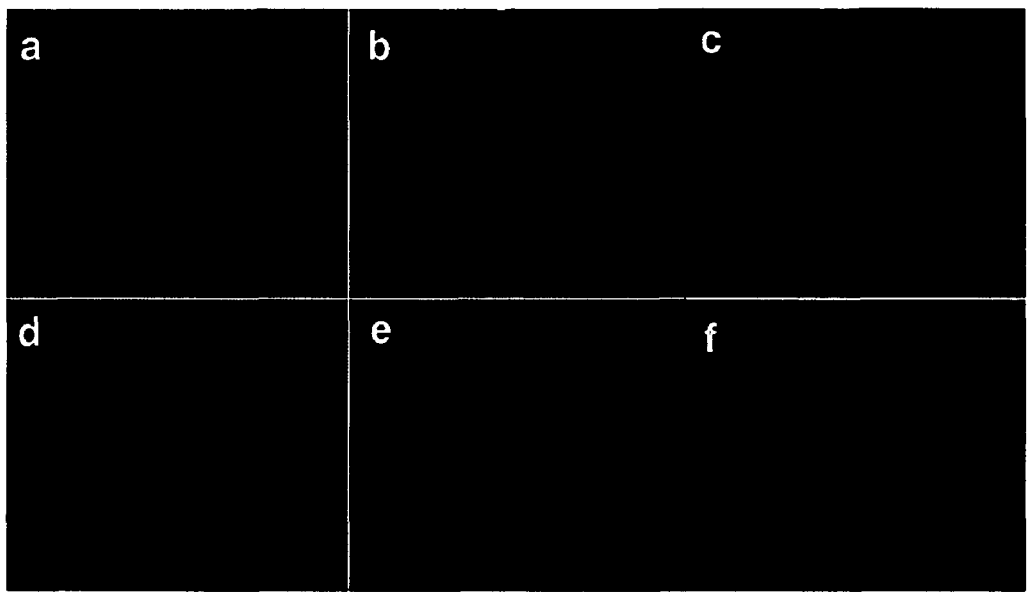
FIG.3D   FIG.3E   FIG.3F
FIG.3G   FIG.3H   FIG.3I
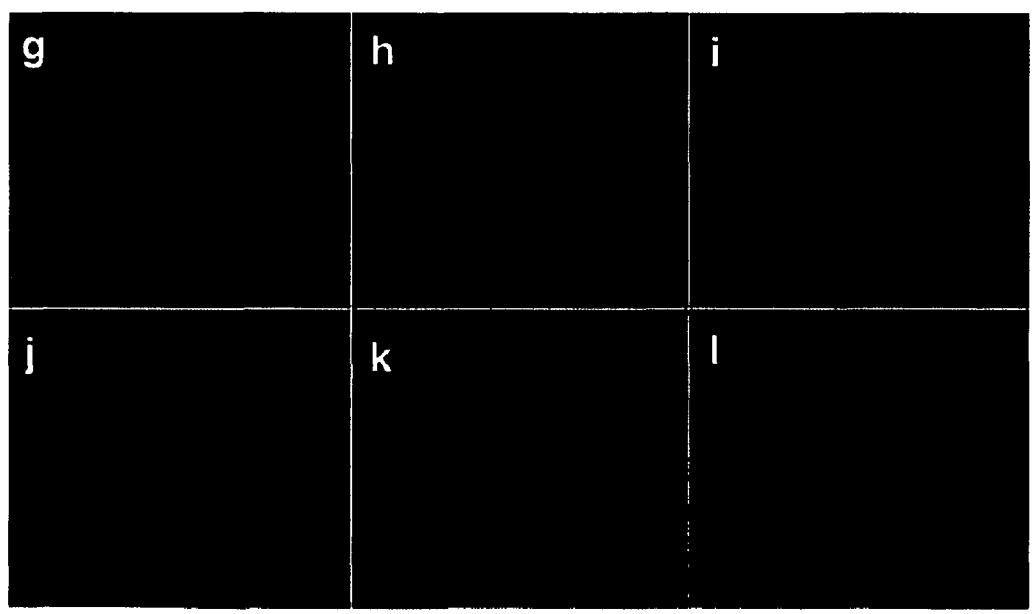
FIG.3J   FIG.3K   FIG.3L Bait: pAS2-1 (empty)  Bait: pAS2-1 (ZNFN3A1)
Prey: pACT2-KIAA0054  Prey: pACT2-KIAA0054

|  | Experimental probability | Theoretical probability | Experimental / Theoretical |
|---|---|---|---|
| C C C T C | (37.0%) | 0.015 (1.5%) | 24.6 |
| C C C T C C | (34.8%) | 0.0034 (0.34%) | 102.3 |
| C C C C T C C | (20.7%) | 0.00079 (0.079%) | 262 |
| C C C T C C T | (20.0%) | 0.00079 (0.079%) | 253 |
| (C) C C C T C C (T) | (10.6%) | 0.00018 (0.018%) | 589 |
| (A) G G A G G G (G) | (10.6%) | 0.00018 (0.018%) | 589 |

ZNFN3A1     β-actin

GENE AND PROTEIN RELATING TO HEPATOCELLULAR CARCINOMA AND METHODS OF USE THEREOF

RELATED APPLICATIONS

This application is a divisional of U.S. Ser. No. 10/788,847 which is a continuation in part of PCT/JP02/09876, filed Sep. 25, 2002, which claims priority to U.S. Ser. No. 60/324,261, filed Sep. 25, 2001; U.S. Ser. No. 60/391,666, filed Jun. 26, 2002; and CASN 2,399,569, filed Aug. 23, 2002 and claims the benefit of U.S. Ser. No. 60/450,644, filed Feb. 28, 2003, each of which is incorporated herein by reference in its entirety.

INCORPORATION-BY-REFERENCE OF SEQUENCE LISTING

The contents of the text file named "25371021D02USSeqList.txt", which was created on Jun. 3, 2010 and is 41.1 KB in size, are hereby incorporated by reference in their entirety.

FIELD OF THE INVENTION

The present invention relates to the field of biological science, more specifically to the field of cancer research. In particular, the present invention relates a novel protein, ZNFN3A1, involved in the proliferation of cancer cells, specifically hepatocellular carcinoma cells. The proteins of the present invention useful, for example, as target molecules for developing drugs against liver cancer.

BACKGROUND OF THE INVENTION

Hepatocellular carcinoma (HCC) is one of the most common cancers worldwide and its incidence is gradually increasing in Japan as well as in United States (Akriviadis E A, et al., Br J Surg. 1998 October; 85(10):1319-31). Recent medical advances have made great progress in diagnosis, a large number of patients with HCCs are still diagnosed at advanced stages and their complete cures from the disease remain difficult. In addition, patients with hepatic cirrhosis or chronic hepatitis have a high risk to HCCs, they may develop multiple liver tumors, or new tumors even after complete removal of initial tumors. Therefore development of highly effective chemotherapeutic drugs and preventive strategies are matters of pressing concern.

SUMMARY OF THE INVENTION

The present application provides an isolated gene, ZNFN3A1, and its encoded polypeptide that is overexpressed in hepatocellular carcinomas (HCC). ZNFN3A1 is an oncoprotein having of zinc finger domain and SET domain. The expression of, ZNFN3A1, is up-regulated in HCCs, and confers an oncogenic activity to cancer cells through a transactivating RNA polymerase II complex, which, in turn, enhances transcription of target genes, including EGFR. Thus, ZNFN3A1 is a novel molecular target for HCCs.

The present application provides a novel human protein, ZNFN3A1, or a functional equivalent thereof, that promotes cell proliferation and the transcriptional activation of target genes. Preferably, the ZNFN3A1 protein includes a 428-amino acid protein with a zinc finger motif encoded by the open reading frame of SEQ. ID. NO.1. The zinc finger domain (MYND) is positioned at codons 49-87 and the SET (Su 3-9, Enhancer-of-zeste, Trihorrax) domain is positioned at codons 117-246. The ZNFN3A1 protein preferably includes the amino acid sequence set forth in SEQ. ID. NO.2. The present application also provides an isolated protein encoded from at least a portion of the ZNFN3A1 polynucleotide sequence, or polynucloetide sequences at least 15%, and more preferably at least 25% complementary to the sequence set forth in SEQ. ID. NO. 1.

The present invention further provides a novel human gene, ZNFN3A1, whose expression is elevated in of HCCs as compared to corresponding non-cancerous liver tissues. The isolated ZNFN3A1 gene includes a polynucleotide sequence as described in SEQ. ID. NO. 1. In particular, the ZNFN3A1 cDNA includes 1622 nucleotides that contain an open reading frame of 1284 nucleotides. The present invention further includes polynucleotides which hybridize to and which are at least 15%, and more preferably at least 25% complementary to the polynucleotide sequence set forth in SEQ. ID. NO. 1, to the extent that they encode a ZNFN3A1 protein or a functional equivalent thereof. Examples of such polynucleotides are degenerates of SEQ. ID. NO. 1.

As used herein, an "isolated ZNFN3A1 gene" is a polynucleotide the structure of which is not identical to that of any naturally occurring polynucleotide or to that of any fragment of a naturally occurring genomic polynucleotide spanning more than three separate genes. An isolated ZNFN3A1 gene includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide. Accordingly, in one aspect, the invention provides an isolated polynucleotide that encodes a polypeptide described herein or a fragment thereof. Preferably, the isolated polypeptide includes a nucleotide sequence that is at least 60% identical to the nucleotide sequence shown in SEQ ID NO: 1. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO: 1. In the case of an isolated polynucleotide which is longer than or equivalent in length to the reference sequence, e.g., SEQ ID NO: 1, the comparison is made with the full length of the reference sequence. Where the isolated polynucleotide is shorter than the reference sequence, e.g., shorter than SEQ ID NO: 1, the comparison is made to segment of the reference sequence of the same length (excluding any loop required by the homology calculation).

Also provided is a transcription activation complex that includes a ZNFN3A1 protein and at least one co-activator thereof. A co-activator is an RNA helicase and/or an RNA polymerase. The RNA helicase is for example, RNA helicase KIAA0054. Alternatively, the RNA polymerase is a RNA polymerase II. Optionally, the complex includes the ZNFN3A1 protein, RNA helicase and RNA polymerase II. The transcription activation complex activates transcription of genes including, for example epidermal growth factor receptor (EGFR) through a direct binding of the complex with an element of "(C)CCCTCC(T)" in the 5' flanking region of the EGFR gene.

The present application also provides a therapeutic agent for treating a cancer. The therapeutic agent is a polynucleotide sequence set forth in (SEQ. ID. NO. 29). Alternatively, the therapeutic agent is as at least a portion of the antisense S-oligonucleotides of the ZNFN3A1 polynucleotide sequence shown and described in SEQ. ID. NO. 1. A suitable antisense S-oligonucleotide is 5'-GCGGGAGGATGGAGCC-3' (SEQ. ID. NO. 29). The therapeutic agent is used to treat hepatoma cells. The course of action of the therapeutic agent is desirably to inhibit growth of hepatoma cells. The therapeutic agent is applied to mammals including humans and domesticated mammals.

An antibody that recognizes the ZNFN3A1 protein is also provided by the present application. In part, an antisense DNA, ribozyme, and RNAi (RNA interference) of the ZNFN3A1 gene is also provided.

Further, a method of screening for a candidate compound for an anti-cancer agent is provided. The method includes contacting the ZNFN3A1 polypeptide with candidate compounds, and selecting compounds that bind to the ZNFN3A1 polypeptide.

The ZNFN3A1 polypeptide may also be contacted with the candidate compounds in the presence of a co-activator under the suitable condition for the formation of the complex of ZNFN3A1 polypeptide and the co-activator thereof. The compounds that inhibit the formation of the complex may then be selected. The co-activator may include RNA helicase and/or RNA polymerase II.

The present invention further provides a method of screening for a candidate compound for an anti-cancer agent, wherein the method includes contacting the ZNFN3A1 polypeptide, a co-activator thereof, and a DNA containing the target sequence of the polypeptide with candidate compounds under the suitable condition for the formation of the complex of ZNFN3A1 polypeptide and the DNA, and selecting compounds that inhibit the formation of the complex. The target sequence is desirably a CBS sequence flanking the 5' region of EGFR.

Also provided is a method of screening for a candidate compound for an anti-cancer agent, wherein the method includes contacting the ZNFN3A1 polypeptide, a co-activator thereof, and a reporter gene with a transcriptional regulatory region recognized by the complex of the polypeptide and the co-activator with candidate compounds under the suitable condition for the expression of the reporter gene, and selecting compounds that inhibit the expression of the reporter gene.

The present invention further provides a method for diagnosis of cancer that includes determining an expression level of the ZNFN3A1 gene in biological sample of specimen, comparing the expression level of ZNFN3A1 gene with that in normal sample, and defining a high expression level of the ZNFN3A1 gene in the sample as having a cancer. The cancer is a hepatocellular carcinoma.

The present invention also provides a method of producing a protein by transfecting or transforming a host cell with a polynucloetide sequence encoding the ZNFN3A1 protein, and expressing the polynucleotide sequence.

The invention further features methods of inhibiting cell growth. Cell growth is inhibited by contacting a cell with a composition of a ZNFN3A1 small interfering RNA (siRNA). ZNFN3A1 is a zinc finger protein that is overexpressed in tumors such as hepatocellular carcinoma. Growth of the cell expressing ZNFN3A1 can be inhibited by the present invention. The cell is further contacted with a transfection-enhancing agent. The cell is provided in vitro, in vivo or ex vivo. The subject is a mammal, e.g., a human, non-human primate, mouse, rat, dog, cat, horse, or cow. The cell is a hepatic cell or a colon cell. Alternatively, the cell is a tumor cell (i.e., cancer cell) such as a colorectal cancer cell or a liver cancer cell. For example, the cell is a colorectal adenocarcinoma cell or a hepatocellular carcinoma cell. By inhibiting cell growth is meant that the treated cell proliferates at a lower rate or has decreased viability than an untreated cell. Cell growth is measured by proliferation assays known in the art.

By the term "siRNA" is meant a double stranded RNA molecule which prevents translation of a target mRNA. Standard techniques of introducing siRNA into the cell are used, including those in which DNA is a template from which RNA is transcribed. The siRNA includes a sense ZNFN3A1 nucleic acid sequence, an anti-sense ZNFN3A1 nucleic acid sequence or both. The siRNA is constructed such that a single transcript has both the sense and complementary antisense sequences from the target gene, e.g., a hairpin.

The method is used to alter gene expression a cell in which expression of ZNFN3A1 is upregulated, e.g., as a result of malignant transformation of the cells. Binding of the siRNA to an ZNFN3A1 transcript in the target cell results in a reduction in ZNFN3A1 production by the cell. The length of the oligonucleotide is at least 10 nucleotides and may be as long as the naturally-occurring ZNFN3A1 transcript. Preferably, the oligonucleotide is 19-25 nucleotides in length. Most preferably, the oligonucleotide is less than 75, 50, 25 nucleotides in length. Exemplary oligonucleotides contain nucleotides 451-471 (SEQ ID NO:69), 532-552 (SEQ ID NO:71), 623-643 (SEQ ID NO:72), 625-645 (SEQ ID NO:73), 636-656 (SEQ ID NO:74), 726-746 (SEQ ID NO:75), 923-943 (SEQ ID NO:77), 1065-1085 (SEQ ID NO:79), and 1258-1278 (SEQ ID NO:80) of a ZNFN3A1 gene when numbered in accordance with SEQ ID NO:1. For example, the ZNFN3A1 siRNA oligonucleotides which inhibit ZNFN3A1 expression in mammalian cells include oligonucleotides containing SEQ ID NO:69, SEQ ID NO:71, SEQ ID NO:72, SEQ ID NO:73, SEQ ID NO:74, SEQ ID NO:75, SEQ ID NO:77, SEQ ID NO:79 or SEQ ID NO:80 as the target sequence.

Also included in the invention are isolated nucleic acid molecules that include the nucleic acid sequence of SEQ ID NO:69, SEQ ID NO:71, SEQ ID NO:72, SEQ ID NO:73, SEQ ID NO:74, SEQ ID NO:75, SEQ ID NO:77, SEQ ID NO:79 or SEQ ID NO:80, or a nucleic acid molecule that is complementary to the nucleic acid sequence of SEQ ID NO:69, SEQ ID NO:71, SEQ ID NO:72, SEQ ID NO:73, SEQ ID NO:74, SEQ ID NO:75, SEQ ID NO:77, SEQ ID NO:79 or SEQ ID NO:80. As used herein, an "isolated nucleic acid" is a nucleic acid removed from its original environment (e.g., the natural environment if naturally occurring) and thus, synthetically altered from its natural state. In the present invention, isolated nucleic acid includes DNA, RNA, and derivatives thereof. When the isolated nucleic acid is RNA or derivatives thereof, base "t" should be replaced with "u" in the nucleotide sequences. As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Complementary nucleic acid sequences hybridize under appropriate conditions to form stable duplexes containing few or no mismatches. Furthermore, the sense strand and antisense strand of the isolated nucleotide of the present invention, can form double stranded nucleotide or hairpin loop structure by the hybridization. In a preferred embodiment, such duplexes contain no more than 1 mismatch for every 10 matches. In an especially preferred embodiment, where the strands of the duplex are fully complementary, such duplexes contain no mismatches. The nucleic acid molecule is less than 1622 nucleotides in length. For example, the nucleic acid molecule is less than 500, 200, or 75 nucleotides in length. Also included in the invention is a vector containing one or more of the nucleic acids described herein, and a cell containing the vectors. The isolated nucleic acids of the present invention are useful for siRNA against ZNFN3A1 or DNA encoding the siRNA. When the nucleic acids are used for siRNA or coding DNA thereof, the sense strand is preferably longer than 19 nucleotides, and more preferably longer than 21 nucleotides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

FIG. 1A is a bar chart depicting the relative expression ratios of A6681 in 20 primary HCCs examined by cDNA microarray. Its expression was significantly up-regulated in eleven of the twelve (91.7%) clinical HCCs that passed through the cutoff filter (both Cy3 and Cy5 signals greater than 25,000). FIG. 1B is a photograph depicting the expression of HCC candidate genes shown by ethidium bromide staining of RT-PCR products (T, tumor tissue; N, normal tissue). Expression of GAPDH served as an internal control. FIG. 1C is a photograph depicting multiple-tissue northern blot analysis of A6681 in various adult human tissues.

FIG. 2B is an illustration depicting the homology between the deduced amino acid sequence of ZNFN3A1 and AK010447. The zf-MYND [zinc finger protein (MYND domain containing)] domain (A), and SET [(Su (var) 3-9, Enhancer-of-zeste, Trithorax)] domain (B) showed 94% and 95% identity, respectively.

FIGS. 3A-3R are photographs depicting the subcellular localization of ZNFN3A1 observed by immunocytochemistry, particularly through fluorescent immunohistochemical staining. FIGS. 3A-3C depict SNU475 cells transfected with plasmid DNA designed to express EGFP-tagged ZNFN3A1 (pEGFP-ZNFN3A1). FIGS. 3D-3F depict SNU475 cells transfected with plasmid DNA designed to express FLAG-tagged ZNFN3A1 (pFLAG-ZNFN3A1). Fluorescent micrographs of anti-FLAG (d), DAPI (e), merge (f). FIGS. 3G-3R depict endogenous expression of ZNFN3A1 in SNU475 cells (g-l) and SNU423 cells (m-r). Fluorescent micrographs of anti-ZNFN3A1 (g, j, m, p), DAPI (h, k, n, q), merge (i, l, o, r). Cells were inoculated in the low concentration ($1.25 \times 10^4$ cells/well) (g-i, m-o) and high concentration ($1.0 \times 10^5$ cells/well) (j-l, p-r).

FIG. 4A are illustrations depicting the FACS analysis of Huh7 cells synchronized by aphidicolin. The cells were growth-arrested in $G_1$ phase by incubation with 7.5 µg/ml aphidicolin for 36 h and released from $G_1$ by removal of aphidicolin. FACS was performed 0, 4, 8, and 12 h later. FIG. 4B are photographs depicting the fluorescent immunocytochemical staining of endogenous ZNFN3A1 protein in Huh7 synchronized by aphidicolin.

FIG. 5A is a photograph depicting the results of a colony formation assay of ZNFN3A1 in NIH3T3 cells, comparing the expression of ZNFN3A1 in mock, NIH3T3-antisense ZNFN3A1, and NIH3T3-sense ZNFN3A1. FIG. 5B is a bar chart depicting the number of colonies counted by electric densitometry. Colonies were counted by electric densitometry. Colony numbers are presented as mean±SD of triplicate plates. A (*) denotes a significant difference ($p<0.05$) as determined by a Fisher's protected least significant test. FIG. 5C are photographs depicting the growth induction of NIH3T3 cells by expressing ZNFN3A1 stably. Expression of ZNFN3A1 mRNA in stable-transfectant (NIH3T3-ZNFN3A1) cells determined by RT-PCR. FIG. 5D is a line graph depicting the time course of cell numbers measured by trypan blue staining method.

FIG. 6A is an illustration depicting the construct of sense (Se) or antisense (As) oligonucleotides designed to suppress ZNFN3A1. FIG. 6B are photographs depicting the expression of ZNFN3A1 in SNU475 cells treated with either sense (Se) or antisense (As) oligonucleotides for 24 h and examined by RT-PCR and western blotting using anti-ZNFN3A1 antibody. FIG. 6C are photographs depicting the results of a colony formation assay using sense or antisense oligonucleotides against ZNFN3A1 mRNA in Huh7, Alexander, SNU423, and SNU475 cells. Antisense oligonucleotides (As) suppressed growth. FIG. 6D is a bar chart depicting the results of an MIT assay, which assesses cell viability, 72 hours after sense or antisense oligonucleotide treatment in Huh7, Alexander, SNU423, and SNU475 cells. FIG. 6E is an illustration depicting the results of FACS analysis, which assesses cell cycle, of Huh7 cells 72 hours after treatment with sense (Se) or antisense (As) oligonucleotides.

FIG. 7A, is an illustration depicting the conserved domain of KIAA0054 and the regions for binding to ZNFN3A1. FIG. 7B are photographs depicting the results of a yeast two-hybrid experiment, wherein pAS2-1 containing ZNFN3A1 were co-transfected into yeast strain AH109 with library vectors containing two different length of KIAA0054. The results show the confirmation of binding between ZNFN3A1 and KIAA0054 in yeast strain AH109. FIG. 7C are photographs depicting the confirmation of binding between ZNFN3A1 and KIAA0054 in mammalian cells. Lysates from HeLa cells were immunoprecipitated with anti-FLAG or anti-HA antibody. The immunoprecipitates were analysed by immunoblotting with anti-HA or anti-FLAG antibody. Lysate was directly analysed by immunoblotting as a control.

FIG. 10A is an illustration of the sequence of oligonucleotides isolated by binding and amplification reactions with GST fusion proteins containing full length ZNFN3A1. The sequences of the core containing the random nucleotide region are shown. FIG. 10B are photographs depicting the reverse transcription analysis of extended transcripts of several genes in COS 7 stable transformant that expressed ZNFN3A1 exogenously.

DETAILED DESCRIPTION OF THE INVENTION

Figure 1A:
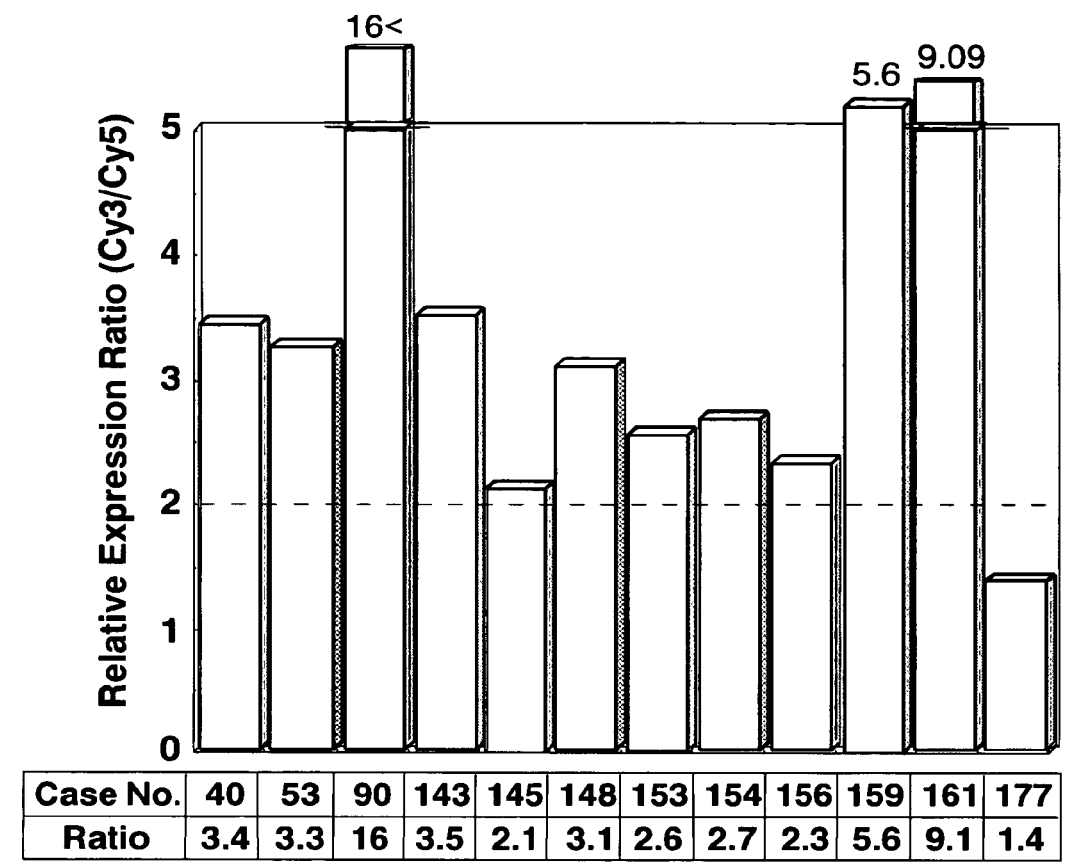
FIGS. 1A-1C depict the expression of A6681 and ZNFN3A1 in HCCs.

The words "a", "an", and "the" as used herein mean "at least one" unless otherwise specifically indicated.

The present invention identifies a novel human gene ZNFN3A1 whose expression is markedly elevated in HCCs compared to non-cancerous liver tissues. The ZNFN3A1 cDNA consists of 1622 nucleotides that contain an open reading frame of 1284 nucleotides as set forth in SEQ. ID. NO. 1. The open reading frame encodes a 428-amino acid protein with a zinc finger motif This protein has been named ZNFN3A1 (zinc finger protein, subfamily 3A (MYND containing), 1) by a nomenclature committee. The nucleic acid and polypeptide sequences of ZNFN3A1 are shown in Tables 1 and 2. In Table 1, the 5' and 3' untranslated region is shown in italic, the start and stop codons are in bold.

The subcellular localization of ZNFN3A1 protein is altered during cell cycle progression and by the density of cultured cells. ZNFN3A1 protein accumulates in the nucleus when cells are in middle to late S phase or cultured in sparse conditions. Whereas, ZNFN3A1 protein localizes in the cytoplasm as well as in the nucleus when cells are in other phases of the cell cycle or grown in a dense condition.

ZNFN3A1 directly associates with a RNA helicase KIAA0054, and forms a complex with RNA polymerase II, which activates transcription of downstream genes including epidermal growth factor receptor (EGFR) through a direct binding of the complex with an element of "(C)CCCTCC(T)" in the 5' flanking region of the EGFR gene.

Exogenous expression of ZNFN3A1 into NIH3T3 cells resulted in increased cell growth. In contrast, suppression of its expression with antisense S-oligonucleotides resulted in a significant growth-inhibition of hepatoma cells. These findings indicate that ZNFN3A1 renders oncogenic activities to cancer cells by transcriptional activation of target genes including EGFR through a complex with RNA helicase and RNA polymerase II, and that inhibition of the activity of the complex is a strategy for the treatment of HCC.

TABLE 1

| Nucleic Acid Sequence of ZNFN3A1 (SEQ ID No: 1) | |
|---|---|
| *gtgcgcgcag ggcgcaggcg cgcgggtccc ggcagcccgt gagacgcccg ctgctggacg* | 60 |
| *cgggtagccg tctgaggtgc cggagctgcg ggagg* atg gag ccg ctg aag gtg | 113 |
| gaa aag ttc gca acc gcc aac agg gga aac ggg ctg cgc gcc gtg acc | 161 |
| ccg ctg cgc ccc gga gag cta ctc ttc cgc tcg gat ccc ttg gcg tac | 209 |
| acg gtg tgc aag ggg agt cgt ggc gtc gtc tgc gac cgc tgc ctt ctc | 257 |
| ggg aag gaa aag ctg atg cga tgc tct cag tgc cgc gtc gcc aaa tac | 305 |
| tgt agt gct aag tgt cag aaa aaa gct tgg cca gac cac aag cgg gaa | 353 |
| tgc aaa tgc ctt aaa agc tgc aaa ccc aga tat cct cca gac tcc gtt | 401 |
| cga ctt ctt ggc aga gtt gtc ttc aaa ctt atg gat gga gca cct tca | 449 |
| gaa tca gag aag ctt tac tca ttt tat gat ctg gag tca aat att aac | 497 |
| aaa ctg act gaa gat aag aaa gag ggc ctc agg caa ctc gta atg aca | 545 |
| ttt caa cat ttc atg aga gaa gaa ata cag gat gcc tct cag ctg cca | 593 |

TABLE 1-continued

Nucleic Acid Sequence of ZNFN3A1 (SEQ ID No: 1)

```
cct gcc ttt gac ctt ttt gaa gcc ttt gca aaa gtg atc tgc aac tct    641
ttc acc atc tgt aat gcg gag atg cag gaa gtt ggt gtt ggc cta tat    689
ccc agt atc tct ttg ctc aat cac agc tgt gac ccc aac tgt tcg att    737
gtg ttc aat ggg ccc cac ctc tta ctg cga gca gtc cga gac atc gag    785
gtg gga gag gag ctc acc atc tgc tac ctg gat atg ctg atg acc agt    833
gag gag cgc cgg aag cag ctg agg gac cag tac tgc ttt gaa tgt gac    881
tgt ttc cgt tgc caa acc cag gac aag gat gct gat atg cta act ggt    929
gat gag caa gta tgg aag gaa gtt caa gaa tcc ctg aaa aaa att gaa    977
gaa ctg aag gca cac tgg aag tgg gag cag gtt ctg gcc atg tgc cag   1025
gcg atc ata agc agc aat tct gaa cgg ctt ccc gat atc aac atc tac   1073
cag ctg aag gtg ctc gac tgc gcc atg gat gcc tgc atc aac ctc ggc   1121
ctg ttg gag gaa gcc ttg ttc tat ggt act cgg acc atg gag cca tac   1169
agg att ttt tcc cca gga agc cat ccc gtc aga ggg gtt caa gtg atg   1217
aaa gtt ggc aaa ctg cag cta cat caa ggc atg ttt ccc caa gca atg   1265
aag aat ctg aga ctg gct ttt gat att atg aga gtg aca cat ggc aga   1313
gaa cac agc ctg att gaa gat ttg att cta ctt tta gaa gaa tgc gac   1361
gcc aac atc aga gca tcc taa gggaacgcag tcagagggaa atacggcgtg      1412
tgtctttgtt gaatgcctta ttgaggtcac acactctatg ctttgttagc tgtgtgaacc 1472
tctcttattg gaaattctgt tccgtgtttg tgtaggtaaa taaaggcaga catggttttgc 1532
aaaccacaag aatcattagt tgtagagaag cacgattata ataaattcaa aacatttggt 1592
tgaggatgcc aaaaaaaaaa aaaaaaaaa                                   1622
```

TABLE 2

Polypeptide Sequence of ZNFN3A1 (SEQ ID NO: 2)

```
Met Glu Pro Leu Lys Val Glu Lys Phe Ala Thr Ala Asn Arg Gly Asn
1               5                   10                  15

Gly Leu Arg Ala Val Thr Pro Leu Arg Pro Gly Glu Leu Leu Phe Arg
            20                  25                  30

Ser Asp Pro Leu Ala Tyr Thr Val Cys Lys Gly Ser Arg Gly Val Val
        35                  40                  45

Cys Asp Arg Cys Leu Leu Gly Lys Glu Lys Leu Met Arg Cys Ser Gln
    50                  55                  60

Cys Arg Val Ala Lys Tyr Cys Ser Ala Lys Cys Gln Lys Lys Ala Trp
65                  70                  75                  80

Pro Asp His Lys Arg Glu Cys Lys Cys Leu Lys Ser Cys Lys Pro Arg
                85                  90                  95

Tyr Pro Pro Asp Ser Val Arg Leu Leu Gly Arg Val Val Phe Lys Leu
            100                 105                 110

Met Asp Gly Ala Pro Ser Glu Ser Glu Lys Leu Tyr Ser Phe Tyr Asp
        115                 120                 125

Leu Glu Ser Asn Ile Asn Lys Leu Thr Glu Asp Lys Lys Glu Gly Leu
    130                 135                 140
```

TABLE 2-continued

Polypeptide Sequence of ZNFN3A1 (SEQ ID NO: 2)

```
Arg Gln Leu Val Met Thr Phe Gln His Phe Met Arg Glu Glu Ile Gln
145                 150                 155                 160

Asp Ala Ser Gln Leu Pro Pro Ala Phe Asp Leu Phe Glu Ala Phe Ala
                165                 170                 175

Lys Val Ile Cys Asn Ser Phe Thr Ile Cys Asn Ala Glu Met Gln Glu
                180                 185                 190

Val Gly Val Gly Leu Tyr Pro Ser Ile Ser Leu Leu Asn His Ser Cys
            195                 200                 205

Asp Pro Asn Cys Ser Ile Val Phe Asn Gly Pro His Leu Leu Leu Arg
    210                 215                 220

Ala Val Arg Asp Ile Glu Val Gly Glu Glu Leu Thr Ile Cys Tyr Leu
225                 230                 235                 240

Asp Met Leu Met Thr Ser Glu Glu Arg Arg Lys Gln Leu Arg Asp Gln
                245                 250                 255

Tyr Cys Phe Glu Cys Asp Cys Phe Arg Cys Gln Thr Gln Asp Lys Asp
                260                 265                 270

Ala Asp Met Leu Thr Gly Asp Glu Gln Val Trp Lys Glu Val Gln Glu
            275                 280                 285

Ser Leu Lys Lys Ile Glu Glu Leu Lys Ala His Trp Lys Trp Glu Gln
    290                 295                 300

Val Leu Ala Met Cys Gln Ala Ile Ile Ser Ser Asn Ser Glu Arg Leu
305                 310                 315                 320

Pro Asp Ile Asn Ile Tyr Gln Leu Lys Val Leu Asp Cys Ala Met Asp
                325                 330                 335

Ala Cys Ile Asn Leu Gly Leu Leu Glu Glu Ala Leu Phe Tyr Gly Thr
                340                 345                 350

Arg Thr Met Glu Pro Tyr Arg Ile Phe Phe Pro Gly Ser His Pro Val
            355                 360                 365

Arg Gly Val Gln Val Met Lys Val Gly Lys Leu Gln Leu His Gln Gly
    370                 375                 380

Met Phe Pro Gln Ala Met Lys Asn Leu Arg Leu Ala Phe Asp Ile Met
385                 390                 395                 400

Arg Val Thr His Gly Arg Glu His Ser Leu Ile Glu Asp Leu Ile Leu
                405                 410                 415

Leu Leu Glu Glu Cys Asp Ala Asn Ile Arg Ala Ser
            420                 425
```

ZNFN3A1 Nucleic Acids and Polypeptides

The present invention provides novel human gene ZNFN3A1, including a polynucleotide sequence as described in SEQ. ID. NO. 1, as well as degenerates and mutants thereof, to the extent that they encode a ZNFN3A1 protein, including the amino acid sequence set forth in SEQ. ID. NO.2 or its functional equivalent. Proteins functionally equivalent to ZNFN3A1 include, for example, homologous proteins of other organisms corresponding to the human ZNFN3A1 protein, as well as mutants of human ZNFN3A1 proteins.

The term "functionally equivalent" is meant that the subject protein has the activity to promote cell proliferation like ZNFN3A1 proteins or to confer oncogenic activity to cancer cells by forming a transactivating complex with an RNA helicase or an RNA polymerase or both, which, in turn, enhances the transcription of target genes, such as EGFR. Whether the subject protein has a cell proliferation activity or not can be judged by introducing the DNA encoding the subject protein into a cell, such as NIH3T3, expressing the protein, and detecting promotion of proliferation of the cells or increase in colony forming activity. The ability of a subject protein to form a complex with either an RNA polymerase or an RNA helicase or both may be assayed by co-immunoprecipitation, such as those described in the Examples below. The enhancement of EGFR transcription may be further assayed using reporter plasmids such as those described in the Examples below.

Methods for preparing proteins functionally equivalent to a given protein are well known by a person skilled in the art and include known methods of introducing mutations into the protein. For example, one skilled in the art can prepare proteins functionally equivalent to the human ZNFN3A1 protein by introducing an appropriate mutation in the amino acid sequence of the human ZNFN3A1 protein by site-directed mutagenesis (Hashimoto-Gotoh, T. et al. (1995), Gene 152, 271-275; Zoller, M J, and Smith, M. (1983), Methods Enzymol. 100, 468-500; Kramer, W. et al. (1984), Nucleic Acids Res. 12, 9441-9456; Kramer W, and Fritz H J. (1987) Methods. Enzymol. 154, 350-367; Kunkel, T A (1985), Proc. Natl. Acad. Sci. USA. 82, 488-492; Kunkel (1988), Methods Enzymol. 85, 2763-2766). Amino acid mutations can also occur in nature. The protein of the present invention includes those proteins having the amino acid sequences of the human ZNFN3A1 protein in which one or more amino acids are mutated, provided the resulting mutated proteins are functionally equivalent to the human ZNFN3A1 protein. The number of amino acids to be mutated in such a mutant is generally 10 amino acids or less, preferably 6 amino acids or less, and more preferably 3 amino acids or less.

Mutated or modified proteins, proteins having amino acid sequences modified by substituting (i.e., deleting, adding and/or replacing) one or more amino acid residues of a certain amino acid sequence, have been known to retain the original biological activity (Mark, D. F. et al., Proc. Natl. Acad. Sci. USA (1984) 81, 5662-5666, Zoller, M. J. & Smith, M., Nucleic Acids Research (1982) 10, 6487-6500, Wang, A. et al., Science 224, 1431-1433, Dalbadie-McFarland, G et al., Proc. Natl. Acad. Sci. USA (1982) 79, 6409-6413).

The amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a protein to which one or more amino acids residues are added to the amino acid sequence of human ZNFN3A1 protein (SEQ. ID. NO. 2) is a fusion protein containing the human ZNFN3A1 protein. Fusion proteins are, fusions of the human ZNFN3A1 protein and other peptides or proteins, and are included in the present invention. Fusion proteins are made by techniques well known to a person skilled in the art, such as by linking the DNA encoding the human ZNFN3A1 protein of the invention with DNA encoding other peptides or proteins, so that the frames match, inserting the fusion DNA into an expression vector and expressing it in a host. There is no restriction as to the peptides or proteins fused to the protein of the present invention.

Peptides that are fused to the protein of the present invention include, for example, FLAG (Hopp, T. P. et al., Biotechnology (1988) 6, 1204-1210), 6×His containing six H is (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Additional examples of proteins that are fused to a protein of the invention include GST (glutathione-S-transferase), Influenza agglutinin (HA), immunoglobulin constant region, β-galactosidase, MBP (maltose-binding protein), and such.

Fusion proteins are prepared by fusing commercially available DNA, encoding the fusion peptides or proteins discussed above, with the DNA encoding the protein of the present invention and expressing the fused DNA prepared.

An alternative method known in the art to isolate functionally equivalent proteins is, for example, the method using a hybridization technique (Sambrook, J. et al., Molecular Cloning 2nd ed. 9.47-9.58, Cold Spring Harbor Lab. Press, 1989). One skilled in the art can readily isolate a DNA having high homology with a whole or part of the DNA sequence (SEQ. ID. NO. 1) encoding the human ZNFN3A1 protein, and isolate functionally equivalent proteins to the human ZNFN3A1 protein from the isolated DNA. The proteins of the present invention include those that are encoded by DNA that hybridize with a whole or part of the DNA sequence encoding the human ZNFN3A1 protein and are functionally equivalent to the human ZNFN3A1 protein. These proteins include mammal homologues corresponding to the protein derived from human or mouse (for example, a protein encoded by a monkey, rat, rabbit and bovine gene). In isolating a cDNA highly homologous to the DNA encoding the human ZNFN3A1 protein from animals, it is particularly preferable to use tissues from skeletal muscle or testis.

The condition of hybridization for isolating a DNA encoding a protein functionally equivalent to the human ZNFN3A1 protein can be routinely selected by a person skilled in the art. For example, hybridization may be performed by conducting prehybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringent condition is, for example, 42° C., 2×SSC, 0.1% SDS, or preferably 50° C., 2×SSC, 0.1% SDS. More preferably, high stringent conditions is used. A high stringent condition is, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors such as temperature and salt concentration can influence the stringency of hybridization and one skilled in the art can suitably select the factors to achieved the requisite stringency.

Alternatively, the polymerase chain reaction (PCR) method, is utilized to isolate a DNA encoding a protein functionally equivalent to the human ZNFN3A1 protein, using a primer synthesized based on the sequence information of the DNA (SEQ. ID. NO. 1) encoding the human ZNFN3A1 protein.

Proteins that are functionally equivalent to the human ZNFN3A1 protein encoded by the DNA isolated through the above hybridization techniques or gene amplification techniques, normally have a high homology to the amino acid sequence of the human ZNFN3A1 protein. "High homology" typically refers to a homology of 40% or higher, preferably 60% or higher, more preferably 80% or higher, even more preferably 95% or higher. The homology of a protein can be determined by following the algorithm in "Wilbur, W. J. and Lipman, D. J. Proc. Natl. Acad. Sci. USA (1983) 80, 726-730".

A protein of the present invention may have variations in amino acid sequence, molecular weight, isoelectric point, the presence or absence of sugar chains, or form, depending on the cell or host used to produce it or the purification method utilized. Nevertheless, so long as it has a function equivalent to that of the human ZNFN3A1 protein (SEQ. ID. NO. 2) of the present invention, it is within the scope of the present invention.

The proteins of the present invention can be prepared as recombinant proteins or natural proteins, by methods well known to those skilled in the art. A recombinant protein can be prepared by inserting a DNA, which encodes the protein of the present invention (for example, the DNA comprising the nucleotide sequence of SEQ. ID. NO. 1), into an appropriate expression vector, introducing the vector into an appropriate host cell, obtaining the extract, and purifying the protein by subjecting the extract to chromatography, for example, ion exchange chromatography, reverse phase chromatography, gel filtration, or affinity chromatography utilizing a column to which antibodies against the protein of the present invention is fixed, or by combining more than one of aforementioned columns.

Also when the protein of the present invention is expressed within host cells (for example, animal cells and *E. coli*) as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions other than the objective protein by cutting with thrombin or factor-Xa as required.

A natural protein is isolated by methods known to a person skilled in the art, for example, by contacting the affinity column, in which antibodies binding to the ZNFN3A1 protein described below are bound, with the extract of tissues or cells expressing the protein of the present invention. The antibodies can be polyclonal antibodies or a monoclonal antibodies.

Included in the invention are partial peptides (i.e., fragments) of the protein of the present invention. The partial peptide has an amino acid sequence specific to the protein of the present invention and consists of at least 7 amino acids, preferably 8 amino acids or more, and more preferably 9 amino acids or more. The partial peptide are used, for example, for preparing antibodies against the protein of the present invention, screening for a compound that binds to the protein of the present invention, and screening for accelerators or inhibitors of the protein of the present invention.

A partial peptide of the invention is produced by genetic engineering, by known methods of peptide synthesis, or by digesting the protein of the invention with an appropriate peptidase. For peptide synthesis, for example, solid phase synthesis or liquid phase synthesis may be used.

The isolated ZNFN3A1 protein includes a putative 428-amino acid protein with a zinc finger motif encoded by the open reading frame of the ZNFN3A1 polynucleotide sequence. The zinc finger domain (MYND) is positioned at codons 49-87 and the SET (Su 3-9, Enhancer-of-zeste, Trihorrax) domain is positioned at codons 117-246. As discussed in detail below, the ZNFN3A1 binding region resides in the SET domain. Therefore, the partial peptide of ZNFN3A1 preferably includes the SET domain.

Furthermore, the present invention provides DNA encoding the proteins of the present invention. The DNA of the present invention are used for the in vivo or in vitro production of the protein of the present invention as described above, or are applied to gene therapy for diseases attributed to genetic abnormality in the gene encoding the protein of the present invention. Any form of the DNA of the present invention can be used, so long as it encodes the protein of the present invention. Specifically, cDNA synthesized from the mRNA, genomic DNA, and chemically synthesized DNA can be used. The DNA of the present invention include a DNA comprising a given nucleotide sequences as well as its degenerate sequences, so long as the resulting DNA encodes a protein of the present invention.

The DNA of the present invention can be prepared by methods known to a person skilled in the art. For example, the DNA of the present invention can be prepared by: preparing a cDNA library from cells which express the protein of the present invention, and conducting hybridization using a partial sequence of the DNA of the present invention (for example, SEQ. ID. NO. 1) as a probe. A cDNA library can be prepared, for example, by the method described in Sambrook J. et al., Molecular Cloning, Cold Spring Harbor Laboratory Press (1989); alternatively, commercially available cDNA libraries may be used. A cDNA library can be also prepared by: extracting RNAs from cells expressing the protein of the present invention, synthesizing oligo DNAs based on the sequence of the DNA of the present invention (for example, SEQ. ID. NO. 1), conducting PCR by using the oligos as primers, and amplifying cDNAs encoding the protein of the present invention.

In addition, by sequencing the nucleotides of the obtained cDNA, the translation region encoded by the cDNA is routinely determined, and the amino acid sequence of the protein of the present invention is easily obtained. Moreover, by screening the genomic DNA library using the obtained cDNA as a probe, the genomic DNA is isolated.

More specifically, mRNAs may first be prepared from a cell, tissue, or organ (for example, ovary, testis, placenta, etc.) in which the protein of the invention is expressed. Known methods can be used to isolate mRNAs; for instance, total RNA may be prepared by guanidine ultracentrifugation (Chirgwin J. M. et al. Biochemistry 18:5294-5299 (1979)) or AGPC method (Chomczynski P. and Sacchi N. Anal. Biochem. 162:156-159 (1987)). In addition, mRNA may be purified from total RNA using mRNA Purification Kit (Pharmacia) and such or, alternatively, mRNA may be directly purified by QuickPrep mRNA Purification Kit (Pharmacia).

The obtained mRNA is used to synthesize cDNA using reverse transcriptase. cDNA are synthesized by using a commercially available kit, such as the AMV Reverse Transcriptase First-strand cDNA Synthesis Kit (Seikagaku Kogyo). Alternatively, cDNA are synthesized and amplified following the 5'-RACE method (Frohman M. A. et al. Proc. Natl. Acad. Sci. U.S.A. 85:8998-9002 (1988); Belyaysky A. et al. Nucleic Acids Res. 17:2919-2932 (1989)), which uses a primer and such, described herein, the 5'-Ampli FINDER RACE Kit (Clontech), and polymerase chain reaction (PCR).

A desired DNA fragment is prepared from the PCR products and ligated with a vector DNA. The recombinant vectors are used to transform *E. coli* and such, and a desired recombinant vector is prepared from a selected colony. The nucleotide sequence of the desired DNA are verified by conventional methods, such as dideoxynucleotide chain termination.

The nucleotide sequence of a DNA of the invention may be designed to be expressed more efficiently by taking into account the frequency of codon usage in the host to be used for expression (Grantham R. et al. Nucleic Acids Res. 9:43-74 (1981)). The DNA of the present invention may be altered by a commercially available kit or a conventional method. For instance, the DNA may be altered by digestion with restriction enzymes, insertion of a synthetic oligonucleotide or an appropriate DNA fragment, addition of a linker, or insertion of the initiation codon (ATG) and/or the stop codon (TAA, TGA, or TAG).

Specifically, the DNA of the present invention includes the DNA comprising the nucleotide sequence encoding the zinc finger domain, positioned at codons 49-87 of SEQ. ID. NO.2 and the DET domain, positioned at codons 117-246 of SEQ. ID. NO.2.

Furthermore, the present invention provides a DNA that hybridizes under stringent conditions with a DNA having a nucleotide sequence of SEQ. ID. NO. 1, and encodes a protein functionally equivalent to the protein of the invention described above. One skilled in the art may appropriately choose stringent conditions. For example, low stringent condition can be used. More preferably, high stringent condition can be used. These conditions are the same as that described above. The hybridizing DNA above is preferably a cDNA or a chromosomal DNA.

ZNFN3A1 Vectors and Host Cells

The present invention also provides a vector into which a DNA of the present invention is inserted. A vector of the present invention is useful to keep a DNA of the present invention in a host cell, or to express the protein of the present invention. When E. coli is a host cell and the vector is amplified and produced in a large amount in E. coli (e.g., JM109, DH5α, HB101, or XL1Blue), the vector should have "ori" to be amplified in E. coli and a marker gene for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc. can be used. In addition, pGEM-T, pDIRECT, and pT7 can also be used for subcloning and extracting cDNA as well as the vectors described above. When a vector is used to produce the protein of the present invention, an expression vector is especially useful. For example, an expression vector to be expressed in E. coli should have the above characteristics to be amplified in E. coli. When E. coli, such as JM109, DH5α, HB101, or XL1 Blue, are used as a host cell, the vector should have a promoter, for example, lacZ promoter (Ward et al., Nature (1989) 341, 544-546; FASEB J (1992) 6, 2422-2427), araB promoter (Better et al., Science (1988) 240, 1041-1043), or T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase),for example, can be used instead of the above vectors.

Optionally, the vector contains a signal sequence for polypeptide secretion. An exemplary signal sequence that directs the protein to be secreted to the periplasm of the E. coli is the pelB signal sequence (Lei, S. P. et al J. Bacteriol. (1987) 169, 4379). Means for introducing of the vectors into the target host cells include, for example, the calcium chloride method, and the electroporation method.

In addition to E. coli, expression vectors are derived from mammals (for example, pcDNA3 (Invitrogen) and pEGF-BOS (Nucleic Acids. Res. 1990, 18 (17), p5322), pEF, pCDM8), expression vectors derived from insect cells (for example, "Bac-to-BAC baculovirus expression system" (GIBCO BRL), pBacPAK8), expression vectors derived from plants (for example pMH1, pMH2), expression vectors derived from animal viruses (for example, pHSV, pMV, pAdexLcw), expression vectors derived from retroviruses (for example, pZIpneo), expression vector derived from yeast (for example, "Pichia Expression Kit" (Invitrogen), pNV11, SP-Q01), and expression vectors derived from Bacillus subtilis (for example, pPL608, pKTH50) can be used for producing the protein of the present invention.

In order to express the vector in animal cells, such as CHO, COS, or NIH3T3 cells, the vector includes a promoter necessary for expression in such cells, for example, the SV40 promoter (Mulligan et al., Nature (1979) 277, 108), the MMLV-LTR promoter, the EF1α promoter (Mizushima et al., Nucleic Acids Res. (1990) 18, 5322), the CMV promoter, and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV, and pOP13.

In addition, methods may be used to express a gene stably and, at the same time, to amplify the copy number of the gene in cells. For example, a vector comprising the complementary DHFR gene (for example pCHO I) may be introduced into CHO cells in which the nucleic acid synthesizing pathway is deleted, and then amplified by methotrexate (MTX). Furthermore, in case of transient expression of a gene, the method wherein a vector comprising a replication origin of SV40 (pcD, etc.) is transformed into COS cells comprising the SV40 T antigen expressing gene on the chromosome can be used.

A protein of the present invention obtained as above is isolated from inside or outside (such as medium) of host cells, and purified as a substantially pure homogeneous protein. The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity is measured standard method, for example by column chromatography, polyacrylamide gel electrophoresis, or HPLC analysis. The method for protein isolation and purification is not limited to any specific method;, any standard method may be used.

For example, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

Examples of chromatography include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies may be performed by liquid chromatography, such as HPLC and FPLC. Thus, the present invention provides for highly purified proteins prepared by the above methods.

A protein of the present invention is optionally modified or partially deleted by treating it with an appropriate protein modification enzyme before or after purification. Useful protein modification enzymes include, but are not limited to, trypsin, chymotrypsin, lysylendopeptidase, protein kinase, and glucosidase.

ZNFN3A1 Antibodies

The present invention provides an antibody that binds to the protein of the invention. The antibody of the invention is used in any form, such as monoclonal or polyclonal antibodies, and includes antiserum obtained by immunizing an animal such as a rabbit with the protein of the invention, all classes of polyclonal and monoclonal antibodies, human antibodies, and humanized antibodies produced by genetic recombination.

A protein of the invention used as an antigen to obtain an antibody is derived from any animal species, but preferably is derived from a mammal such as a human, mouse, or rat, more preferably from a human. A human-derived protein is obtained from the nucleotide or amino acid sequences disclosed herein.

According to the present invention, the protein to be used as an immunization antigen is a complete protein or a partial peptide of the protein. A partial peptide comprises, for example, the amino (N)-terminal or carboxy (C)-terminal fragment of a protein of the present invention. Herein, an antibody is defined as a protein that reacts with either the full length or a fragment of a protein of the present invention.

A gene encoding a protein of the invention or its fragment is inserted into a known expression vector, which is then used to transform a host cell as described herein. The desired protein or its fragment is recovered from the outside or inside of host cells by any standard method, and subsequently be used as an antigen. Alternatively, whole cells expressing the protein or their lysates, or a chemically synthesized protein are used as the antigen.

Any mammalian animal is immunized with the antigen, but preferably the compatibility with parental cells used for cell fusion is taken into account. In general, animals of Rodentia, Lagomorpha, or Primates are used.

Animals of Rodentia include, for example, mouse, rat, and hamster. Animals of Lagomorpha include, for example, rabbit. Animals of Primates include, for example, a monkey of Catarrhini (old world monkey) such as *Macaca fascicularis*, rhesus monkey, sacred baboon, and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the proteins of the present invention are prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies are isolated from the serum. Immunoglobulin G or M are prepared from a fraction which recognizes only the protein of the present invention using, for example, an affinity column coupled with the protein of the present invention, and further purifying this fraction by using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells are fused according to known methods, for example, the method of Milstein et al. (Galfre, G. and Milstein, C., Methods Enzymol. (1981) 73, 3-46).

Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method, in which a non human animal is immunized with an antigen for preparing hybridoma, human lymphocytes such as those infected by EB virus may be immunized with a protein, protein expressing cells, or their lysates in vitro. Then, the immunized lymphocytes are fused with human-derived myeloma cells that are capable of indefinitely dividing, such as U266, to yield a hybridoma producing a desired human antibody that is able to bind to the protein can be obtained (Unexamined Published Japanese Patent Application No. (JP-A) Sho 63-17688).

The obtained hybridomas are subsequently transplanted into the abdominal cavity of a mouse and the ascites are extracted. The obtained monoclonal antibodies are purified by, for example, ammonium sulfate precipitation, a protein A or protein G column, DEAE ion exchange chromatography, or an affinity column to which the protein of the present invention is coupled. The antibody of the present invention is used not only for purification and detection of the protein of the present invention, but also as a candidate for agonists and antagonists of the protein of the present invention. In addition, this antibody is applied to the antibody treatment for diseases related to the protein of the present invention. When the obtained antibody is administered to the human body (antibody treatment), a human antibody or a humanized antibody is preferable for reducing immunogenicity.

For example, transgenic animals having a repertory of human antibody genes are immunized with an antigen selected from a protein, protein expressing cells, or their lysates. Antibody producing cells are then collected from the animals and fused with myeloma cells to obtain hybridoma, from which human antibodies against the protein can be prepared (see WO92-03918, WO93-2227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained are also recombinantly prepared using genetic engineering techniques (see, for example, Borrebaeck C. A. K. and Larrick J. W. Therapeutic Monoclonal Antibodies, published in the United Kingdom by MacMillan Publishers LTD (1990)). For example, a DNA encoding an antibody is cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention is a fragment of an antibody or modified antibody, so long as it binds to one or more of the proteins of the invention. For instance, the antibody fragment may be Fab, $F(ab')_2$, Fv, or single chain Fv (scFv), in which Fv fragments from H and L chains are ligated by an appropriate linker (Huston J. S. et al. Proc. Natl. Acad. Sci. U.S.A. 85:5879-5883 (1988)). More specifically, an antibody fragment may be generated by treating an antibody with an enzyme, such as papain or pepsin. Alternatively, a gene encoding the antibody fragment is constructed, inserted into an expression vector, and expressed in an appropriate host cell (see, for example, Co M. S. et al. J. Immunol. 152:2968-2976 (1994); Better M. and Horwitz A. H. Methods Enzymol. 178:476-496 (1989); Pluckthun A. and Skerra A. Methods Enzymol. 178:497-515 (1989); Lamoyi E. Methods Enzymol. 121:652-663 (1986); Rousseaux J. et al. Methods Enzymol. 121:663-669 (1986); Bird R. E. and Walker B. W. Trends Biotechnol. 9:132-137 (1991)).

An antibody is modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention is obtained as a chimeric antibody, between a variable region derived from nonhuman antibody and the constant region derived from human antibody, or as a humanized antibody, comprising the complementarity determining region (CDR) derived from nonhuman antibody, the frame work region (FR) derived from human antibody, and the constant region. Such antibodies are prepared by using known technology.

Antibodies obtained as above are purified to homogeneity. For example, the separation and purification of the antibody can be performed according to separation and purification methods used for general proteins. For example, the antibody is separated and isolated by the appropriately selected and combined use of column chromatographies, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988), but are not limited thereto.

A protein A column and protein G column is used as the affinity column. Exemplary protein A columns to be used include, for example, Hyper D, POROS, and Sepharose F.F. (Pharmacia).

Exemplary chromatography, with the exception of affinity includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press, 1996). The chromatographic procedures are carried out by liquid-phase chromatography, such as HPLC, FPLC.

For example, measurement of absorbance, enzyme-linked immunosorbent assay (ELISA), enzyme immunoassay (EIA), radioimmunoassay (RIA), and/or immunofluorescence are used to measure the antigen binding activity of the antibody of the invention. In ELISA, the antibody of the present invention is immobilized on a plate, protein of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the protein, such as a C-terminal or N-terminal fragment, may be used as a protein. BIAcore (Pharmacia) may be used to evaluate the activity of the antibody according to the present invention.

The above methods allow for the detection or measurement of the protein of the invention, by exposing the antibody of the invention to a sample assumed to contain the protein of the invention, and detecting or measuring the immune complex formed by the antibody and the protein.

The method of detection or measurement of the protein according to the invention can specifically detect or measure a protein, thus the method is useful in a variety of experiments in which the protein is used.

ZNFN3A1 Antisense Nucleic Acids

The present invention also provides a polynucleotide which hybridizes with the DNA encoding human ZNFN3A1 protein (SEQ. ID. NO.1) or the complementary strand thereof, and which comprises at least 15 nucleotides. The polynucleotide of the present invention is preferably a polynucleotide which specifically hybridizes with the DNA encoding the protein of the present invention. The term "specifically hybridize" as used herein, means that cross-hybridization does not occur significantly with DNA encoding other proteins, under the usual hybridizing conditions, preferably under stringent hybridizing conditions. Such polynucleotides include, probes, primers, nucleotides and nucleotide derivatives (for example, antisense oligonucleotides and ribozymes), which specifically hybridize with DNA encoding the protein of the invention or its complementary strand. Moreover, such polynucleotide are utilized for the preparation of DNA chip.

The present invention includes an antisense oligonucleotide that hybridizes with any site within the nucleotide sequence of SEQ. ID. NO. 1. The antisense oligonucleotide is preferably against at least 15 continuous nucleotides of the nucleotide sequence of SEQ. ID. NO. 1. An antisense oligonucleotide, which contains an initiation codon in the above-mentioned at least 15 continuous nucleotides, is even more preferred.

Derivatives or modified products of antisense oligonucleotides can be used as antisense oligonucleotides. Examples of such modified products include lower alkyl phosphonate modifications such as methyl-phosphonate-type or ethyl-phosphonate-type, phosphorothioate modifications and phosphoroamidate modifications.

The term "antisense oligonucleotides" as used herein means, nucleotides corresponding to those constituting a specified region of a DNA or mRNA are entirely complementary, in addition to those oligonucleotide which have a mismatch of one or more nucleotides, as long as the DNA or mRNA and the antisense oligonucleotide can specifically hybridize with the nucleotide sequence of SEQ. ID. NO. 1.

Such polynucleotides are contained as those having, in the "at least 15 continuous nucleotide sequence region", a homology of at least 70% or higher, preferably at 80% or higher, more preferably 90% or higher, even more preferably 95% or higher. The algorithm stated herein can be used to determine the homology. Such polynucleotides are useful as probes for the isolation or detection of DNA encoding the protein of the invention as stated in a later example or as a primer used for amplifications.

The antisense oligonucleotide derivatives of the present invention act upon cells producing the protein of the invention by binding to the DNA or mRNA encoding the protein, inhibiting its transcription or translation, promoting the degradation of the mRNA, and inhibiting the expression of the protein of the invention, thereby resulting in the inhibition of the protein's function.

An antisense oligonucleotide derivative of the present invention is made into an external preparation, such as a liniment or a poultice, by mixing with a suitable base material which is inactive against the derivatives.

Also, as needed, the derivatives can be formulated into tablets, powders, granules, capsules, liposome capsules, injections, solutions, nose-drops and freeze-drying agents by adding excipients, isotonic agents, solubilizers, stabilizers, preservatives, pain-killers, and such. These are prepared by methods known in the art.

The antisense oligonucleotide derivative is given to the patient by directly applying onto the ailing site or by injecting into a blood vessel so that it will reach the site of ailment. An antisense-mounting medium can also be used to increase durability and membrane-permeability. Examples are, liposome, poly-L-lysine, lipid, cholesterol, lipofectin or derivatives of these.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

The antisense oligonucleotide of the invention inhibits the expression of the protein of the invention and is thereby useful for suppressing the biological activity of the protein of the invention. Also, expression-inhibitors, comprising the antisense oligonucleotide of the invention, are useful in the point that they can inhibit the biological activity of the protein of the invention.

Screening and Detection Methods

The present invention provides a method of screening for a compound that binds to the protein of the present invention by using the protein of the present invention. This screening method comprises the steps of: (a) contacting the protein of the present invention or a partial peptide thereof with a subject sample, (b) detecting the binding activity between the protein of the present invention or the partial peptide thereof and the subject sample, and (c) selecting a compound that binds to the protein of the present invention or the partial peptide thereof.

The protein of the present invention to be used for screening is a recombinant protein or a protein derived from the nature, or a partial peptide thereof. Any subject sample, for example, cell extracts, cell culture supernatant, products of fermenting microorganism, extracts from marine organism, plant extracts, purified or crude proteins, peptides, non-peptide compounds, synthetic micromolecular compounds and natural compounds, can be used. The protein of the present invention to be contacted with a subject sample is, for example, a purified protein, a soluble protein, a form bound to a carrier, or a fusion protein fused with other proteins.

As a method of screening for proteins, that bind to the protein of the present invention using the protein of the present invention, many methods well known by a person skilled in the art can be used. Such a screening are conducted by, for example, immunoprecipitation method, specifically, in the following manner. The gene encoding the protein of the present invention is expressed in animal cells and so on by inserting the gene to an expression vector for foreign genes, such as pSV2neo, pcDNA I, and pCD8. The promoter to be used for the expression may be any promoter that can be used commonly and include, for example, the SV40 early promoter (Rigby in Williamson (ed.), Genetic Engineering, vol. 3. Academic Press, London, p. 83-141 (1982)), the EF-1α promoter (Kim et al., Gene 91, p217-223 (1990)), the CAG promoter (Niwa et al. Gene 108, p. 193-200 (1991)), the RSV LTR promoter (Cullen Methods in Enzymology 152, p. 684-704 (1987)) the SRα promoter (Takebe et al., Mol. Cell. Biol. 8, p. 466 (1988), the CMV immediate early promoter (Seed and Aruffo Proc. Natl. Acad. Sci. USA 84, p. 3365-3369 (1987)), the SV40 late promoter (Gheysen and Fiers J. Mol. Appl. Genet. 1, p. 385-394 (1982)), the Adenovirus late promoter (Kaufman et al., Mol. Cell. Biol. 9, p. 946 (1989)), the HSV TK promoter and so on. The introduction of the gene into animal cells to express a foreign gene can be performed according to any methods, for example, the electroporation method (Chu G. et al. Nucl. Acids Res. 15, 1311-1326 (1987)), the calcium phosphate method (Chen, C. and Okayama, H. Mol. Cell. Biol. 7, 2745-2752 (1987)), the DEAE dextran method (Lopata, M. A. et al. Nucl. Acids Res. 12, 5707-5717 (1984)), Sussman, D. J. and Milman, G. Mol. Cell. Biol. 4, 1642-1643 (1985)), the Lipofectin method (Derijard, B. Cell 7 1025-1037 (1994); Lamb, B. T. et al. Nature Genetics 5, 22-30 (1993): Rabindran, S. K. et al. Science 259, 230-234 (1993)), and so on. The protein of the present invention can be expressed as a fusion protein comprising a recognition site (epitope) of a monoclonal antibody by introducing the epitope of the monoclonal antibody, whose specificity has been revealed, to the N- or C-terminus of the protein of the present invention. A commercially available epitope-antibody system can be used (Experimental Medicine 13, 85-90 (1995)). Vectors which can express a fusion protein with, for example, β-galactosidase, maltose binding protein, glutathione S-transferase, green florescence protein (GFP) and so on by the use of its multiple cloning sites are commercially available.

A fusion protein prepared by introducing only small epitopes consisting of several to a dozen amino acids so as not to change the property of the protein of the present invention by the fusion is also reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage), and such, and monoclonal antibodies recognizing them can be used as the epitope-antibody system for screening proteins binding to the protein of the present invention (Experimental Medicine 13, 85-90 (1995)).

In immunoprecipitation, an immune complex is formed by adding these antibodies to cell lysate prepared by using an appropriate detergent. The immune complex consists of the protein of the present invention, a protein comprising the binding ability with the protein, and an antibody. Immunoprecipitation is conducted by using antibodies against the protein of the present invention, besides using antibodies against the above epitopes. An antibody against the protein of the present invention can be prepared, for example, by introducing a gene encoding the protein of the present invention to an appropriate E. coli expression vector, expressing the gene in E. coli, purifying the expressed protein, and immunizing rabbits, mice, rats, goats, domestic fowls and such against the protein. The antibody is also prepared by immunizing the above animals against a synthesized partial peptide of the protein of the present invention.

An immune complex is precipitated, for example by Protein A Sepharose or Protein G sepharose when the antibody is a mouse IgG antibody. If the protein of the present invention is prepared as a fusion protein with an epitope, such as GST, an immune complex can be formed in the same manner as in the use of the antibody against the protein of the present invention, by using a substance specifically binding to these epitopes, such as glutathione-Sepharose 4B.

Immunoprecipitation is performed by following or according to, for example, the methods in the literature (Harlow, E. and Lane, D.: Antibodies pp. 511-552, Cold Spring Harbor Laboratory publications, New York (1988))

SDS-PAGE is commonly used for analysis of immunoprecipitated proteins and the bound protein can be analyzed by the molecular weight of the protein by using gels with an appropriate concentration. Since the protein bound to the protein of the present invention is difficult to detect by a common staining method, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein is purified directly from the SDS-polyacrylamide gel and its sequence is determined, when the molecular weight of a protein has been revealed.

As a method for isolating proteins binding to the protein of the present invention by using the protein, for example, West-Western blotting analysis (Skolnik, E. Y. et al., Cell (1991) 65, 83-90) can be used. Specifically, a protein binding to the protein of the present invention can be obtained by preparing a cDNA library from cells, tissues, organs (for example, tissues such as ovary, testis, and placenta or cultured cells) expected to express a protein binding to the protein of the present invention by using a phage vector (e.g., ZAP), expressing the protein on LB-agarose, fixing the protein expressed on a filter, reacting the purified and labeled protein of the present invention with the above filter, and detecting the plaques expressing proteins bound to the protein of the present invention according to the label. The protein of the invention may be labeled by utilizing the binding between biotin and avidin, or by utilizing an antibody that specifically binds to the protein of the present invention, or a peptide or polypeptide (for example, GST) that is fused to the protein of the present invention. Methods using radioisotope or fluorescence and such may be also used.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton S, and Treisman R (1992) Cell 68, 597-612", "Fields S, and Sternglanz R. Trends Genet. (1994) 10:286-292").

In the two-hybrid system, the protein of the invention is fused to the SRF-binding region or GAL4-binding region and expressed in yeast cells. A cDNA library is prepared from cells expected to express a protein binding to the protein of the invention, such that the library, when expressed, is fused to the VP16 or GAL4 transcriptional activation region. The cDNA library is then introduced into the above yeast cells and the cDNA derived from the library is isolated from the positive clones detected (when a protein binding to the protein of the invention is expressed in yeast cells, the binding of the two activates a reporter gene, making positive clones detectable). A protein encoded by the cDNA can be prepared by introducing the cDNA isolated above to *E. coli* and expressing the protein.

In addition to HIS2, exemplary reporter genes, includes, Ade2 gene, lacZ gene, CAT gene, luciferase gene A compound binding to the protein of the present invention is screened using affinity chromatography. For example, the protein of the invention is immobilized on a carrier of an affinity column, and a test sample, containing a protein capable of binding to the protein of the invention is supposed to be expressed, is applied to the column. A test sample herein may be, for example, cell extracts, cell lysates, etc. After loading the test sample, the column is washed, and proteins bound to the protein of the invention is prepared.

The amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the protein of the invention and a test compound can be observed real-time as a surface plasmon resonance signal, using only a minute amount of protein and without labeling (for example, BIAcore, Pharmacia). Therefore, it is possible to evaluate the binding between the protein of the invention and a test compound using a biosensor such as BIAcore.

The methods of screening for molecules that bind when the immobilized protein of the present invention is exposed to synthetic chemical compounds, or natural substance banks, or a random phage peptide display library, or the methods of screening using high-throughput based on combinatorial chemistry techniques (Wrighton N c, Farrel F X, Chang R, Kashyap A K, Barbone F P, Mulcahy L S, Johnson D L, Barret R W, Jolliffe L K, Dower W J; Small peptides as potent mimetics of the protein hormone erythropoietin, Science (UNITED STATES) Jul. 26, 1996, 273 p 458-64, Verdine G L., The combinatorial chemistry of nature. Nature (ENGLAND) Nov. 7, 1996, 384, p 11-13, Hogan J C Jr., Directed combinatorial chemistry. Nature (ENGLAND) Nov. 7, 1996, 384 p 17-9) to isolate not only proteins but chemical compounds that bind to protein of the present invention (including agonist and antagonist) are well known to one skilled in the art.

A compound isolated by the screening is a candidate for drugs which promote or inhibit the activity of the protein of the present invention, for treating or preventing diseases attributed to, for example, cell proliferative diseases such as cancer. A compound in which a part of the structure of the compound obtained by the present screening method having the activity of binding to the protein of the present invention is converted by addition, deletion and/or replacement, is included in the compounds obtained by the screening method of the present invention.

Moreover the present invention provides a method for screening a compound which promotes or inhibits the activity of the protein of the present invention. Since the ZNFN3A1 protein of the present invention has the activity of promoting cell proliferation, a compound which promotes or inhibits this activity of a ZNFN3A1 protein of the present invention can be screened using this activity as an index.

This screening method includes the steps of: (a) culturing cells which express ZNFN3A1 protein in the presence of the subject sample, (b) detecting the proliferation of the cells, and (c) selecting a compound which promotes or inhibits the proliferation in comparison with the proliferation detected in the absence of the subject sample. Compounds that inhibit the expression and/or activity of ZNFN3A1 find utility as anti-cancer agents.

Any ZNFN3A1 proteins can be used for screening so long as they comprise the activity of inhibiting cell proliferation. For example, a human ZNFN3A1 protein can be used and proteins functionally equivalent to these proteins is used. ZNFN3A1 proteins are expressed endogenously or exogenously by cells.

Any subject samples, for example, cell extracts, cell culture supernatant, products of fermenting microorganism, extracts of marine organism, plant extracts, purified or crude proteins, peptides, non-peptide compounds, synthetic micromolecular compounds, natural compounds, can be used. A compound obtained by the above screening for compounds that bind to the protein of the present invention are used as the subject compound.

The compound isolated by this screening is a candidate for agonists or antagonists of the protein of the present invention. The term "agonist" refers to molecules that activate the function of the protein of the present invention by binding thereto. Likewise, the term "antagonist" refers to molecules that inhibit the function of the protein of the present invention by binding thereto. Moreover, a compound isolated by this screening is a candidate for compounds which inhibit the in vivo interaction of the protein of the present invention with molecules (including DNAs and proteins).

Cell proliferation is detected, for example, by determining the speed of cell proliferation, measuring the cell cycle and such, as well as by measuring the colony forming activity as described in the Examples.

The compound isolated by the screening is a candidate for drugs which inhibit the activity of the protein of the present invention and can be applied to the treatment of diseases associated with the protein of the present invention, for example, cancer, more particularly hepatocellular carcinoma.

Moreover, compound in which a part of the structure of the compound inhibiting the activity of ZNFN3A1 proteins is converted by addition, deletion and/or replacement are also included in the compounds obtainable by the screening method of the present invention.

Pharmaceutical Compositions

When administrating the compound isolated by the method of the invention as a pharmaceutical for humans and other mammals, such as mice, rats, guinea-pigs, rabbits, cats, dogs, sheep, pigs, cattle, monkeys, baboons, chimpanzees, the isolated compound are directly administered or are formulated into a dosage form using known pharmaceutical preparation methods. For example, according to the need, the drugs are taken orally, as sugar-coated tablets, capsules, elixirs and microcapsules, or non-orally, in the form of injections of sterile solutions or suspensions with water or any other pharmaceutically acceptable liquid. The compounds are mixed with pharmacologically acceptable carriers or medium, specifically, sterilized water, physiological saline, plant-oil, emulsifiers, suspending agents, surfactants, stabilizers, flavoring agents, excipients, vehicles, preservatives, binders and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier, such as oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannnose, D-mannitol, and sodium chloride, rare used as aqueous solutions for injections. These are used in conjunction with suitable solubilizers, such as alcohol, specifically ethanol, polyalcohols such as propylene glycol and polyethylene glycol, non-ionic surfactants, such as Polysorbate 80™ and HCO-50.

Sesame oil or Soy-bean oil is used as a oleaginous liquid and may be used in conjunction with benzyl benzoate or benzyl alcohol as a solubilizers and may be formulated with a buffer, such as phosphate buffer and sodium acetate buffer; a pain-killer, such as procaine hydrochloride; a stabilizer, such as benzyl alcohol, phenol; and an anti-oxidant. The prepared injection is filled into a suitable ampule.

Methods well known to one skilled in the art are used to administer the inventive pharmaceutical compound to patients, for example as intraarterial, intravenous, percutaneous injections and also as intranasal, transbronchial, intramuscular or oral administrations. The dosage and method of administration vary according to the body-weight and age of a patient and the administration method; however, one skilled in the art can routinely select them. If said compound is encodable by a DNA, the DNA is inserted into a vector for gene therapy and the vector administered to perform the therapy. The dosage and method of administration vary according to the body-weight, age, and symptoms of a patient but one skilled in the art can select them suitably.

For example, although there are some differences according to the symptoms, the dose of a compound that binds with the protein of the present invention and regulates its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

Methods of Diagnosing Cancer

Moreover, the present invention provides a method of diagnosing cancer using ZNFN3A1 gene as a diagnostics marker. This diagnosing method comprises the steps of:
  (a) determining a expression level of the ZNFN3A1 gene in biological sample of specimen;
  (b) comparing the expression level of ZNFN3A1 gene with that in normal sample, and
  (c) defining a high expression level of the ZNFN3A1 gene in the sample as having a cancer.

The expression levels of ZNFN3A1 gene in a particular specimen are estimated, for example, by quantifying mRNA corresponding to or protein encoded by the ZNFN3A1 gene. Quantification methods for mRNA are known to those skilled in the art. The levels of mRNAs corresponding to the ZNFN3A1 gene are estimated by Northern blotting or RT-PCR. Since all the nucleotide sequences of the ZNFN3A1 gene is shown in SEQ ID NO:1, anyone skilled in the art can design the nucleotide sequences for probes or primers to quantify the ZNFN3A1 gene.

Also the expression level of the ZNFN3A1 gene are analyzed based on activity or quantity of protein encoded by the ZNFN3A1 gene. A method for determining the quantity of the ZNFN3A1 protein is shown in bellow. For example, immunoassay method is useful for determination of the protein in biological material. Any biological materials can be used for the determination of the protein or it's activity. For example, blood sample is analyzed for estimation of the protein encoded by serum marker. Another hand, a suitable method can be selected for the determination of the activity protein encoded by the ZNFN3A1 gene according to the activity of each protein to be analyzed.

Expression levels of the ZNFN3A1 gene in a specimen (test sample) are estimated and compared with those in a normal sample. When such a comparison shows that the expression level of ZNFN3A1 gene is higher than those in the normal sample, the subject is judged to be affected with a cancer. The expression level of ZNFN3A1 gene in the specimens from the normal sample and subject may be determined at the same time. Alternatively, normal ranges of the expression levels can be determined by a statistical method based on the results obtained by analyzing the expression level of ZNFN3A1 gene in specimens previously collected from a control group. A result obtained by examining the sample of a subject is compared with the normal range; when the result does not fall within the normal range, the subject is judged to be affected with the cancer. In the present invention, the cancer to be diagnosed is preferably a hepatocellular carcinoma.

A diagnostic agent for diagnosing hepatocellular carcinoma is also provided. The diagnostic agent includes a compound that binds to the DNA or the protein of the present invention. Preferably, the oligonucleotide that hybridize to polynucleotide of the present invention, or the antibodies may that bind to the protein of the present invention are used as these compound.

Methods of Inhibiting Cell Growth

The present invention relates to inhibiting cell growth, i.e, cancer cell growth by inhibiting ZNFN3A1 expression. ZNFN3A1 expression is inhibited by small interfering RNA (siRNA) that specifically target of the ZNFN3A1 gene. A ZNFN3A1 target includes, for example, nucleotides 451-471 (SEQ ID NO:69), 532-552 (SEQ ID NO:71), 623-643 (SEQ ID NO:72), 625-645 (SEQ ID NO:73), 636-656 (SEQ ID NO:74), 726-746 (SEQ ID NO:75), 923-943 (SEQ ID NO:77), 1065-1085 (SEQ ID NO:79), and 1258-1278 (SEQ ID NO:80) of SEQ ID NO:1.

In non-mammalian cells, double-stranded RNA (dsRNA) has been shown to exert a strong and specific silencing effect on gene expression, which is referred as RNA interference (RNAi) (Sharp P A. RNAi and double-strand RNA. Genes Dev. 1999 Jan. 15; 13(2):139-41.). dsRNA is processed into 20-23 nucleotides dsRNA called small interfering RNA (siRNA) by an enzyme containing RNase III motif The siRNA specifically targets complementary mRNA with a multicomponent nuclease complex (Hammond S M, Bernstein E, Beach D, Hannon G J. An RNA-directed nuclease mediates post-transcriptional gene silencing in *Drosophila* cells. Nature. 2000 Mar. 16; 404(6775):293-6., Hannon G J. RNA interference. Nature. 2002 Jul. 11; 418(6894):244-51.). In mammalian cells, siRNA composed of 20 or 21-mer dsRNA with 19 complementary nucleotides and 3' terminal oncomplementary dimmers of thymidine or uridine, have been shown to have a gene specific knock-down effect without inducing global changes in gene expression (Elbashir S M, Harborth J, Lendeckel W, Yalcin A, Weber K, Tuschl T. Duplexes of 21-nucleotide RNAs mediate RNA interference in cultured mammalian cells. Nature. 2001 May 24; 411 (6836):494-8.). In addition, plasmids containing small nuclear RNA (snRNA) U6 or polymerase III H1-RNA promoter effectively produce such short RNA recruiting type III class of RNA polymerase III and thus can constitutively suppress its target mRNA (Miyagishi M, Taira K. U6 promoter-driven siRNAs with four uridine 3' overhangs efficiently suppress targeted gene expression in mammalian cells. Nat. Biotechnol. 2002 May; 20(5):497-500, Brummelkamp T R, Bernards R, Agami R. A System for Stable Expression of Short Interfering RNAs in Mammalian Cells Science. 296 (5567):550-553, Apr. 19, 2002.).

Figure 13:
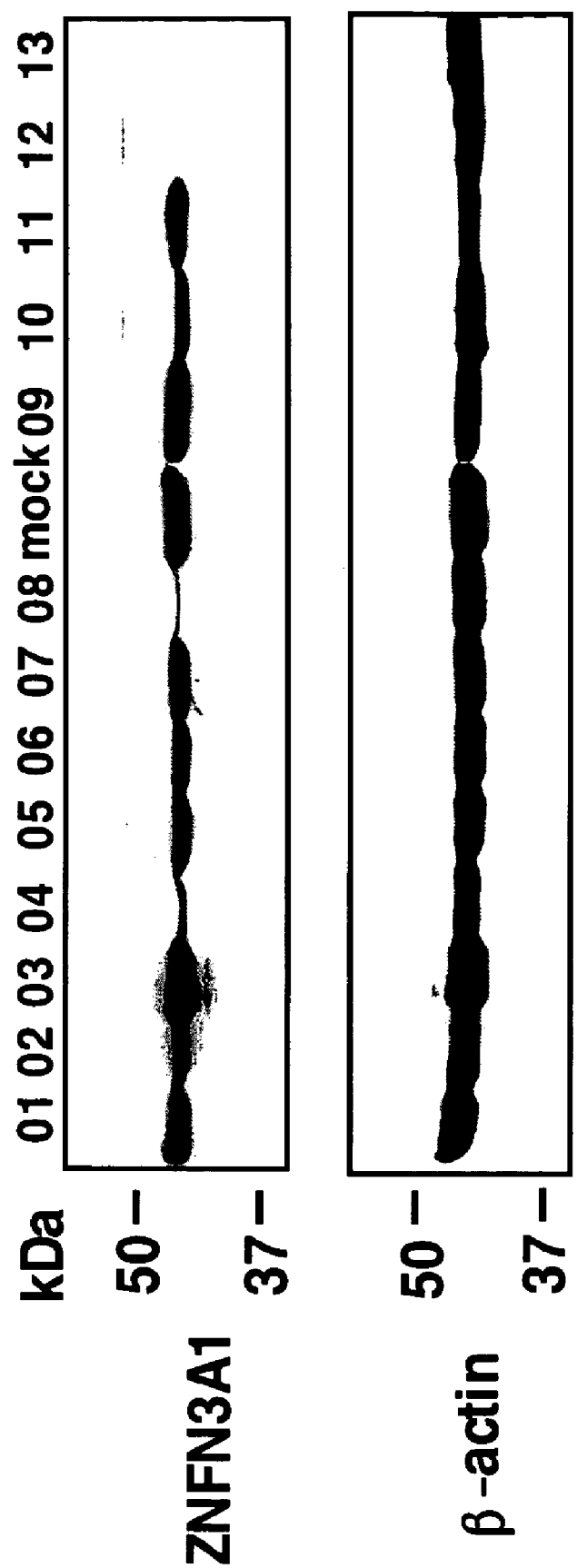
FIG. 13 is a photograph of an immunoblot showing the effect of ZNFN3A1 siRNAs on exogenous ZNFN3A1 expression in COST cells.

13 different expression plasmids were constructed to express hairpin-looped ZNFN3A1-siRNA (See Example 11). The plasmids were tested for their ability to inhibit cell growth. Four plasmids (psiU6BX-ZNFN3A1-4, -8, -12 and -13) markedly and five plasmids (psiU6BX-ZNFN3A1-2, -5, -6, -7, and -10) moderately suppressed endogenous ZNFN3A1 expression, while the remaining four plasmids (psiU6BX-ZNFN3A1-1, -3, -9 and -11 exhibited no or little effect on the expression. (FIG. 13). Various human hepatoma and colorectal cancer cells transfected with psiU6BX-siZNFN3A1-12, showed reduced number of surviving cells compared to control plasmids. FACS analysis revealed that their death was due to apoptosis.

The growth of cells are inhibited by contacting a cell, with a composition containing a ZNFN3A1 siRNA. The cell is further contacted with a transfection agent. Suitable transfection agents are known in the art. By inhibition of cell growth is meant the cell proliferates at a lower rate or has decreased viability compared to a cell not exposed to the composition. Cell growth is measured by methods known in the art such as, the MTT cell proliferation assay.

The ZNFN3A1-siRNA is directed to a single target ZNFN3A1 gene sequence. Alternatively, the siRNA is directed to multiple target ZNFN3A1 gene sequences. For example, the composition contains ZNFN3A1-siRNA directed to two, three, four, or five or more ZNFN3A1 target sequences. By ZNFN3A1 target sequence is meant a nucleotide sequence that is identical to a portion of the ZNFN3A1 gene or complementary to a portion of a naturally occurring ZNFN3A1 gene. The target sequence can include the 5' untranslated (UT) region, the open reading frame (ORF) or the 3' untranslated region of the human ZNFN3A1 gene. Alternatively, the siRNA is a nucleic acid sequence complementary to an upstream or downstream modulator of ZNFN3A1 gene expression. Examples of upstream and downstream modulators include, a transcription factor that binds the ZNFN3A1 gene promoter, a kinase or phosphatase that interacts with the ZNFN3A1 polypeptide, a ZNFN3A1 promoter or enhancer.

ZNFN3A1-siRNA which hybridize to target mRNA decrease or inhibit production of the ZNFN3A1 polypeptide product encoded by the ZNFN3A1 gene by associating with the normally single-stranded mRNA transcript, thereby interfering with translation and thus, expression of the protein. The siRNA is less than 500, 200, 100, 50, or 25 nucleotides in length. Preferably the siRNA is 19-25 nucleotides in length. Exemplary nucleic acid sequence for the production of ZNFN3A1-siRNA include the sequences of 451-471 (SEQ ID NO:69), 532-552 (SEQ ID NO:71), 623-643 (SEQ ID NO:72), 625-645 (SEQ ID NO:73), 636-656 (SEQ ID NO:74), 726-746 (SEQ ID NO:75), 923-943 (SEQ ID NO:77), 1065-1085 (SEQ ID NO:79), or 1258-1278 (SEQ ID NO:80) of SEQ ID NO:1 as the target sequence. Furthermore, in order to enhance the inhibition activity of the siRNA, nucleotide "u" can be added to 3' end of the antisense strand of the target sequence. The number of "u"s to be added is at least 2, generally 2 to 10, preferably 2 to 5. The added "u"s form single strand at the 3' end of the antisense strand of the siRNA.

The cell is any cell that expresses or over-expresses ZNFN3A1. The cell is a hepatic cell or an epithelial cell such as a colon cell. Alternatively, the cell is a tumor cell such as a carcinoma, adenocarcinoma, blastoma, leukemia, myeloma, or sarcoma. The cell is a hepatocellular carcinoma or a colorectal adenocarcinoma cell.

An ZNFN3A1-siRNA is directly introduced into the cells in a form that is capable of binding to the mRNA transcripts. Alternatively, the DNA encoding the ZNFN3A1-siRNA is in a vector.

Vectors are produced for example by cloning a ZNFN3A1 target sequence into an expression vector operatively-linked regulatory sequences flanking the ZNFN3A1 sequence in a manner that allows for expression (by transcription of the DNA molecule) of both strands. An RNA molecule that is antisense to ZNFN3A1 mRNA is transcribed by a first promoter (e.g., a promoter sequence 3' of the cloned DNA) and an RNA molecule that is the sense strand for the ZNFN3A1 mRNA is transcribed by a second promoter (e.g., a promoter sequence 5' of the cloned DNA). The sense and antisense strands hybridize in vivo to generate siRNA constructs for silencing of the ZNFN3A1 gene. Alternatively, two constructs are utilized to create the sense and anti-sense strands of a siRNA construct. Cloned ZNFN3A1 can encode a construct having secondary structure, e.g., hairpins, wherein a single transcript has both the sense and complementary antisense sequences from the target gene.

A loop sequence consisting of an arbitrary nucleotide sequence can be located between the sense and antisense sequence in order to form the hairpin loop structure.

Thus, the present invention also provides siRNA having the general formula 5'-[A]-[B]-[A']-3', wherein [A] is a ribonucleotide sequence corresponding to a sequence selected from the group consisting of nucleotides 451-471 (SEQ ID NO:69), 532-552 (SEQ ID NO:71), 623-643 (SEQ ID NO:72), 625-645 (SEQ ID NO:73), 636-656 (SEQ ID NO:74), 726-746 (SEQ ID NO:75), 923-943 (SEQ ID NO:77), 1065-1085 (SEQ ID NO:79), and 1258-1278 (SEQ ID NO:80) of SEQ ID NO:1,

[B] is a ribonucleotide sequence consisting of 3 to 23 nucleotides, and

[A'] is a ribonucleotide sequence consisting of the complementary sequence of [A]

The region [A] hybridizes to [A'], and then a loop consisting of region [B] is formed. The loop sequence may be preferably 3 to 23 nucleotide in length. The loop sequence, for example, can be selected from group consisting of following sequences (http://www.ambion.com/techlib/tb/tb_506.html). In the siRNA of the present invention, nucleotide "u" can be added to the 3' end of [A'], in order to enhance the inhibiting activity of the siRNA. The number of "u"s to be added is at least 2, generally 2 to 10, preferably 2 to 5. Furthermore, loop sequence consisting of 23 nucleotides also provides active siRNA (Jacque, J.-M., Triques, K., and Stevenson, M. (2002) Modulation of HIV-1 replication by RNA interference. Nature 418: 435-438.).

AUG: Sui, G., Soohoo, C., Affar, E. B., Gay, F., Shi, Y., Forrester, W. C., and Shi, Y. (2002) A DNA vector-based RNAi technology to suppress gene expression in mammalian cells. Proc. Natl. Acad. Sci. USA 99(8): 5515-5520.

CCC, CCACC or CCACACC: Paul, C. P., Good, P. D., Winer, I., and Engelke, D. R. (2002) Effective expression of small interfering RNA in human cells. Nature Biotechnology 20:505-508.

UUCG: Lee, N. S., Dohjima, T., Bauer, G., Li, H., Li, M.-J., Ehsani, A., Salvaterra, P., and Rossi, J. (2002) Expression of small interfering RNAs targeted against HIV-1 rev transcripts in human cells. Nature Biotechnology 20:500-505.

CTCGAG or AAGCUU: Editors of Nature Cell Biology (2003) Whither RNAi? Nat Cell Biol. 5:489-490.

UUCAAGAGA: Yu, J.-Y., DeRuiter, S. L., and Turner, D. L. (2002) RNA interference by expression of short-interfering RNAs and hairpin RNAs in mammalian cells. Proc. Natl. Acad. Sci. USA 99(9): 6047-6052. For example, preferable siRNAs having hairpin loop structure of the present invention are shown below. In the following structure, the loop sequence can be selected from group consisting of AUG, CCC, UUCG, CCACC, CTCGAG, AAGCUU, CCACACC, and UUCAAGAGA. Preferable loop sequence is UUCAAGAGA ("ttcaagaga" in DNA).

```
aaucagagaagcuuuacucau-[B]-augaguaaagcuucucugauu
(for target sequence of SEQ ID NO: 69)

aacucguaaugacauuucaac-[B]-guugaaaugucauuacgaguu
(for target sequence of SEQ ID NO: 71)

aaaagugaucugcaacucuuu-[B]-aaagaguugcagaucacuuuu
(for target sequence of SEQ ID NO: 72)

aagugaucugcaacucuuuca-[B]-ugaaagaguugcagaucacuu
(for target sequence of SEQ ID NO: 73)

aacucuuucaccaucuguaau-[B]-auuacagauggugaaagaguu
(for target sequence of SEQ ID NO: 74)

aacuguucgauuguguucaau-[B]-auugaacacaaucgaacaguu
(for target sequence of SEQ ID NO: 75)

aacuggugaugagcaaguaug-[B]-cauacuugcucaucaccaguu
(for target sequence of SEQ ID NO: 77)

aacaucuaccagcugaaggug-[B]-caccuucagcugguagauguu
(for target sequence of SEQ ID NO: 79)

aagcaaugaagaaucugagac-[B]-gucucagauucuucauugcuu
(for target sequence of SEQ ID NO: 80)
```

The regulatory sequences flanking the ZNFN3A1 sequence are identical or are different, such that their expression can be modulated independently, or in a temporal or spatial manner. siRNAs are transcribed intracellularly by cloning the ZNFN3A1 gene templates into a vector containing, e.g., a RNA pol III transcription unit from the small nuclear RNA (snRNA) U6 or the human H1 RNA promoter. For introducing the vector into the cell, transfection-enhancing agent can be used. FuGENE (Rochediagnostices), Lipofectamin 2000 (Invitrogen), Oligofectamin (Invitrogen), and Nucleofactor (Wako pure Chemical) are useful as the transfection-enhancing agent.

Oligonucleotides and oligonucleotides complementary to various portions of ZNFN3A1 mRNA were tested in vitro for their ability to decrease production of ZNFN3A1 in tumor cells (e.g., using the Alexander and HepG2 hepatocellular carcinoma (HCC) cell line and the HCT116 and SW948) according to standard methods. A reduction in ZNFN3A1 gene product in cells contacted with the candidate siRNA composition compared to cells cultured in the absence of the candidate composition is detected using ZNFN3A1-specific antibodies or other detection strategies. Sequences which decrease production of ZNFN3A1 in in vitro cell-based or cell-free assays are then tested for there inhibitory effects on cell growth. Sequences which inhibit cell growth in in vitro cell-based assay are test in in vivo in rats or mice to confirm decreased ZNFN3A1 production and decreased tumor cell growth in animals with malignant neoplasms.

Methods of Treating Malignant Tumors

Patients with tumors characterized as over-expressing ZNFN3A1 are treated by administering ZNFN3A1-siRNA. siRNA therapy is used to inhibit expression of ZNFN3A1 in patients suffering from or at risk of developing, for example, hepatocellular carcinomas, or colorectal cancer. Such patients are identified by standard methods of the particular tumor type. Hepatocellular carcinoma is diagnosed for example, by enlargement of the liver, tomography, ultrasound or biopsy. Colorectal cancer is diagnosed for example, by blood in stool, colonosopy, flexible sigmoidoscopy, CEA Assay, double contrast barium enema CT Scan, tomography or biopsy.

Treatment is efficacious if the treatment leads to clinical benefit such as, a reduction in expression of ZNFN3A1, or a decrease in size, prevalence, or metastatic potential of the tumor in the subject. When treatment is applied prophylactically, "efficacious" means that the treatment retards or prevents tumors from forming or prevents or alleviates a symptom of clinical symptom of the tumor. Efficaciousness is determined in association with any known method for diagnosing or treating the particular tumor type.

siRNA therapy is carried out by administering to a patient a siRNA by standard vectors and/or gene delivery systems. Suitable gene delivery systems may include liposomes, receptor-mediated delivery systems, or viral vectors such as herpes viruses, retroviruses, adenoviruses and adeno-associated viruses, among others. A reduction in ZNFN3A1 production results in a decrease ZNFN3A1 complex formation with KIAA0054 protein and RNA polymerase II or a decrease in ZNFN3A1 protein expression. A therapeutic nucleic acid composition is formulated in a pharmaceutically acceptable carrier. The therapeutic composition may also include a gene delivery system as described above. Pharmaceutically acceptable carriers are biologically compatible vehicles which are suitable for administration to an animal, e.g., physiological saline. A therapeutically effective amount of a compound is an amount which is capable of producing a medically desirable result such as reduced production of a ZNFN3A1 gene product, reduction of cell growth, e.g., proliferation, or a reduction in tumor growth in a treated animal.

Parenteral administration, such as intravenous, subcutaneous, intramuscular, and intraperitoneal delivery routes, may be used to deliver ZNFN3A1-siRNA compositions. For treatment of hepatic tumors, direct infusion the portal vein is useful.

Dosages for any one patient depends upon many factors, including the patient's size, body surface area, age, the particular nucleic acid to be administered, sex, time and route of administration, general health, and other drugs being administered concurrently. Dosage for intravenous administration of nucleic acids is from approximately $10^6$ to $10^{22}$ copies of the nucleic acid molecule.

The polynucleotides are administered by standard methods, such as by injection into the interstitial space of tissues such as muscles or skin, introduction into the circulation or into body cavities or by inhalation or insufflation. Polynucleotides are injected or otherwise delivered to the animal with a pharmaceutically acceptable liquid carrier, e.g., a liquid carrier, which is aqueous or partly aqueous. The polynucleotides are associated with a liposome (e.g., a cationic or anionic liposome). The polynucleotide includes genetic information necessary for expression by a target cell, such as a promoters.

The invention will be further described in the following examples, which do not limit the scope of the invention described in the claims.

EXAMPLE 1

General Methods

Cell Lines and Tissue Specimens

Human hepatoma cell lines Huh7, Alexander, and HepG2, human colon cancer lines HCT116 and SW948, human cervix cell line HeLA, mouse fibroblast cell line NIH3T3 and monkey fibroblast cell line COS 7 were obtained from the American Type Culture Collection (ATCC). In example 11, human hepatoma cell line Huh7 was also obtained from Japanese Collection of Research Bioresources (JCRB). Human hepatoma cell lines, SNU398, SNU423, SNU449 and SNU475 were obtained from the Korea cell-line bank. All these cells are publicly available.

All cell lines were grown in monolayers in appropriate media: Dulbecco's modified Eagle's medium for Alexander, Huh7, HepG2, NIH3T3 and COS 7; Eagle's Minimum Essential Medium for HeLa; McCoy's 5A for HCT116; Leibovitz's L-15 for SW948; RPMI1640 for SNU398, SNU423, SNU449 and SNU475 supplemented with 10% fetal bovine serum and 1% antibiotic/antimycotic solution (Sigma). All cells were maintained at 37° C. in humid air with 5% $CO_2$, (Alexander, Huh7, HepG2, SNU398, SNU423, SNU449, SNU475, HCT116, HeLa, NIH3T3 and COST) or without $CO_2$ (SW948).

Cloning of ZNFN3A1

Cloning of ZNFN3A1 was done by PCR using KOD-plus (TOYOBO). For *E. Coli* expression, coding region of ZNFN3A1 was cloned in the EcoR I-Kpn I site of pET21a.

For mammalian cell expression, coding region of ZNFN3A1 was cloned in the EcoR I-Kpn I site of pcDNA3.1 (+) and (−) (Invitrogen), EcoR I-Kpn I site of pFLAG and EcoR I-Kpn I site of pEGFP (Clontech). Coding region of KIAA0054 was cloned in the EcoRI-Xho I site of pCMV-HA (Clontech).

ZNFN3A1 Polyclonal Antibody Production

Rabbit anti-ZNFN3A1 polyclonal antibody was generated. Full coding sequence of ZNFN3A1 was amplified by PCR reaction using testis cDNA as a template and cloned in pET21 a (Novagen). The cloned vector was transfected into BL21-CodonPlus® competent cells (Stratagene). Recombinant ZNFN3A1 protein was induced by 1.0 mM IPTG at 30° C. for 6 h. His-ZNFN3A1 fusion protein was purified using Pro Bond™ Resin (Invitrogen). Rabbits were immunized ten times with purified His-ZNFN3A1. Immunoblotting with this polyclonal antibody showed single 50 kD band of FLAG-tagged ZNFN3A1, which was identical pattern to that detected using anti-FLAG monoclonal antibody (Sigma) (data not shown).

RNA Preparation and RT-PCR

Total RNA was extracted with the Qiagen Rneasy Kit (Qiagen) or Trizol reagent (Life technologies) according to the manufacturer's protocol. Ten-microgram aliquots of total RNA were reversely transcribed for single-stranded cDNAs using poly $dT_{12-18}$ primer (Amersham Biosciences) with Superscript II reverse transcriptase (Life Technologies). Each single-stranded cDNA was diluted for subsequent PCR amplification. Standard RT-PCR was carried out in a 20 μl volume of PCR buffer (TAKARA), and amplified for 4 min at 94° C. for denaturing, followed by 20 (for GAPDH) or 30 (for ZNFN3A1) cycles of 94° C. for 30 s, 56° C. for 30 s, 72° C. for 30 s, in the Gene Amp PCR system 9700 (Perkin-Elmer). Primer sequence were as follows, for GAPDH

```
forward;
5'-ACAACAGCCTCAAGATCATCAG-3'     (SEQ ID NO: 30)
and reverse;
5'-GGTCCACCACTGACACGTTG-3',      (SEQ ID NO: 31)

for or ZNFN3A1
forward;
5'-TTCCCGATATCAACATCTACCAG-3'    (SEQ ID NO: 32)
and reverse;
5'-AGTGTGTGACCTCAATAAGGCAT-3'.   (SEQ ID NO: 33)
```

Construction of psiU6BX6 Plasmid

The DNA fragment encoding siRNA was inserted between the part1 and part2 sequence of psiU6BX6 Plasmid.

```
Nucleotide Sequence of the psiU6BX6 Plasmid
                                       (SEQ ID NO: 44)
GACGGATCGGGAGATCTCCCGATCCCCTATGGTGCACTCTCAGTACAATC

TGCTCTGGATCCACTAGTAACGGCCGCCAGTGTGCTGGAATTCGGCTTGG
```

-continued

GGATCAGCGTTTGAGTAAGAGCCCGCGTCTGAACCCTCCGCGCCGCCCCG
GCCCCAGTGGAAAGACGCGCAGGCAAAACGCACCACGTGACGGAGCGTGA
CCGCGCGCCGAGCGCGCGCCAAGGTCGGGCAGGAAGAGGGCCTATTTCCC
ATGATTCCTTCATATTTGCATATACGATACAAGGCTGTTAGAGAGATAAT
TAGAATTAATTTGACTGTAAACACAAAGATATTAGTACAAAATACGTGAC
GTAGAAAGTAATAATTTCTTGGGTAGTTTGCAGTTTTAAAATTATGTTTT
AAAATGGACTATCATATGCTTACCGTAACTTGAAAGTATTTCGATTTCTT
GGCTTTATATATCTTGTGGAAAGGACGAAACACC-----TTTTTACATCA
GGTTGTTTTTCTGTTTGGTTTTTTTTTACACCACGTTTATACGCCGGTG
CACGGTTTACCACTGAAAACACCTTTCATCTACAGGTGATATCTTTTAAC
ACAAATAAAATGTAGTAGTCCTAGGAGACGGAATAGAAGGAGGTGGGGCC
TAAAGCCGAATTCTGCAGATATCCATCACACTGGCGGCCGCTCGAGTGAG
GCGGAAAGAACCAGCTGGGGCTCTAGGGGGTATCCCCACGCGCCCTGTAG
CGGCGCATTAAGCGCGGCGGGTGTGGTGGTTACGCGCAGCGTGACCGCTA
CACTTGCCAGCGCCCTAGCGCCCGCTCCTTTCGCTTTCTTCCCTTCCTTT
CTCGCCACGTTCGCCGGCTTTCCCCGTCAAGCTCTAAATCGGGGCTCCC
TTTAGGGTTCCGATTTAGTGCTTTACGGCACCTCGACCCCAAAAAACTTG
ATTAGGGTGATGGTTCACGTAGTGGGCCATCGCCCTGATAGACGGTTTTT
CGCCCTTTGACGTTGGAGTCCACGTTCTTTAATAGTGGACTCTTGTTCCA
AACTGGAACAACACTCAACCCTATCTCGGTCTATTCTTTTGATTTATAAG
GGATTTTGCCGATTTCGGCCTATTGGTTAAAAAATGAGCTGATTTAACAA
AAATTTAACGCGAATTAATTCTGTGGAATGTGTGTCAGTTAGGGTGTGGA
AAGTCCCCAGGCTCCCCAGCAGGCAGAAGTATGCAAAGCATGCATCTCAA
TTAGTCAGCAACCAGGTGTGGAAAGTCCCCAGGCTCCCCAGCAGGCAGAA
GTATGCAAAGCATGCATCTCAATTAGTCAGCAACCATAGTCCCGCCCCTA
ACTCCGCCCATCCCGCCCCTAACTCCGCCCAGTTCCGCCCATTCTCCGCC
CCATGGCTGACTAATTTTTTTTATTTATGCAGAGGCCGAGGCCGCCTCTG
CCTCTGAGCTATTCCAGAAGTAGTGAGGAGGCTTTTTTGGAGGCCTAGGC
TTTTGCAAAAAGCTCCCGGGAGCTTGTATATCCATTTTCGGATCTGATCA
AGAGACAGGATGAGGATCGTTTCGCATGATTGAACAAGATGGATTGCACG
CAGGTTCTCCGGCCGCTTGGGTGGAGAGGCTATTCGGCTATGACTGGGCA
CAACAGACAATCGGCTGCTCTGATGCCGCCGTGTTCCGGCTGTCAGCGCA
GGGGCGCCCGGTTCTTTTTGTCAAGACCGACCTGTCCGGTGCCCTGAATG
AACTGCAGGACGAGGCAGCGCGGCTATCGTGGCTGGCCACGACGGGCGTT
CCTTGCGCAGCTGTGCTCGACGTTGTCACTGAAGCGGGAAGGGACTGGCT
GCTATTGGGCGAAGTGCCGGGGCAGGATCTCCTGTCATCTCACCTTGCTC
CTGCCGAGAAAGTATCCATCATGGCTGATGCAATGCGGCGGCTGCATACG
CTTGATCCGGCTACCTGCCCATTCGACCACCAAGCGAAACATCGCATCGA
GCGAGCACGTACTCGGATGAAGCCGGTCTTGTCGATCAGGATGATCTGG
ACGAAGAGCATCAGGGGCTCGCGCCAGCCGAACTGTTCGCCAGGCTCAAG

-continued

GCGCGCATGCCCGACGGCGAGGATCTCGTCGTGACCCATGGCGATGCCTG
CTTGCCGAATATCATGGTGGAAAATGGCCGCTTTTCTGGATTCATCGACT
GTGGCCGGCTGGGTGTGGCGGACCGCTATCAGGACATAGCGTTGGCTACC
CGTGATATTGCTGAAGAGCTTGGCGGCGAATGGGCTGACCGCTTCCTCGT
GCTTTACGGTATCGCCGCTCCCGATTCGCAGCGCATCGCCTTCTATCGCC
TTCTTGACGAGTTCTTCTGAGCGGGACTCTGGGGTTCGAAATGACCGACC
AAGCGACGCCCAACCTGCCATCACGAGATTTCGATTCCACCGCCGCCTTC
TATGAAAGGTTGGGCTTCGGAATCGTTTTCCGGGACGCCGGCTGGATGAT
CCTCCAGCGCGGGGATCTCATGCTGGAGTTCTTCGCCCACCCCAACTTGT
TTATTGCAGCTTATAATGGTTACAAATAAAGCAAAGCATCACAAATTTCA
CAAATAAAGCATTTTTTTCACTGCATTCTAGTTGTGGTTTGTCCAAACTC
ATCAATGTATCTTATCATGTCTGTATACCGTCGACCTCTAGCTAGAGCTT
GGCGTAATCATGGTCATAGCTGTTTCCTGTGTGAAATTGTTATCCGCTCA
CAATTCCACACAACATACGAGCCGGAAGCATAAAGTGTAAAGCCTGGGGT
GCCTAATGAGTGAGCTAACTCACATTAATTGCGTTGCGCTCACTGCCCGC
TTTCCAGTCGGGAAACCTGTCGTGCCAGCTGCATTAATGAATCGGCCAAC
GCGCGGGGAGAGGCGGTTTGCGTATTGGGCGCTCTTCCGCTTCCTCGCTC
ACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAA
AGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAA
AAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGC
GCCTTATCCGGTAACTATCGTCTTGAGTCCAACCCGGTAAGACACGACTT
ATCGCCACTGGCAGCAGCCACTGGTAACAGGATTAGCAGAGCGAGGTATG
TAGGCGGTGCTACAGAGTTCTTGAAGTGGTGGCCTAACTACGGCTACACT
AGAAGAACAGTATTTGGTATCTGCGCTCTGCTGAAGCCAGTTACCTTCGG
AAAAAGAGTTGGTAGCTCTTGATCCGGCAAACAAACCACCGCTGGTAGCG
GTTTTTTTGTTTGCAAGCAGCAGATTACGCGCAGAAAAAAAGGATCTCAA
GAAGATCCTTTGATCTTTTCTACGGGGTCTGACGCTCAGTGGAACGAAAA
CTCACGTTAAGGGATTTTGGTCATGAGATTATCAAAAAGGATCTTCACCT
AGATCCTTTTAAATTAAAAATGAAGTTTTAAATCAATCTAAAGTATATAT
GAGTAAACTTGGTCTGACAGTTACCAATGCTTAATCAGTGAGGCACCTAT
CTCAGCGATCTGTCTATTTCGTTCATCCATAGTTGCCTGACTCCCCGTCG
TGTAGATAACTACGATACGGGAGGGCTTACCATCTGGCCCCAGTGCTGCA
ATGATACCGCGAGACCCACGCTCACCGGCTCCAGATTTATCAGCAATAAA
CCAGCCAGCCGGAAGGGCCGAGCGCAGAAGTGGTCCTGCAACTTTATCCG
CCTCCATCCAGTCTATTAATTGTTGCCGGGAAGCTAGAGTAAGTAGTTCG

-continued

```
CCAGTTAATAGTTTGCGCAACGTTGTTGCCATTGCTACAGGCATCGTGGT

GTCACGCTCGTCGTTTGGTATGGCTTCATTCAGCTCCGGTTCCCAACGAT

CAAGGCGAGTTACATGATCCCCCATGTTGTGCAAAAAAGCGGTTAGCTCC

TTCGGTCCTCCGATCGTTGTCAGAAGTAAGTTGGCCGCAGTGTTATCACT

CATGGTTATGGCAGCACTGCATAATTCTCTTACTGTCATGCCATCCGTAA

GATGCTTTTCTGTGACTGGTGAGTACTCAACCAAGTCATTCTGAGAATAG

TGTATGCGGCGACCGAGTTGCTCTTGCCCGGCGTCAATACGGGATAATAC

CGCGCCACATAGCAGAACTTTAAAAGTGCTCATCATTGGAAAACGTTCTT

CGGGGCGAAAACTCTCAAGGATCTTACCGCTGTTGAGATCCAGTTCGATG

TAACCCACTCGTGCACCCAACTGATCTTCAGCATCTTTTACTTTCACCAG

CGTTTCTGGGTGAGCAAAAACAGGAAGGCAAAATGCCGCAAAAAAGGGAA

TAAGGGCGACACGGAAATGTTGAATACTCATACTCTTCCTTTTTCAATAT

TATTGAAGCATTTATCAGGGTTATTGTCTCATGAGCGGATACATATTTGA

ATGTATTTAGAAAAATAAACAAATAGGGGTTCCGCGCACATTTCCCCGAA

AAGTGCCACCTGACGTC
``` snRNA U6 gene is reported to be transcribed by RNA polymerase III, which produce short transcripts with uridines at the 3' end. The genomic fragment of the snRNA U6 gene containing the promoter region was amplified by PCR using a set of primers, 5'-GGGGATCAGCGTTTGAGTAA-3 (SEQ ID NO:45)', and 5'-TAGGCCCCACCTCCTTCTAT (SEQ ID NO:46)-3' and human placental DNA as a template. The product was purified and cloned into pCR plasmid vector using a TA cloning kit according to the supplier's protocol (Invitrogen). The BamHI, XhoI fragment containing the snRNA U6 gene was purified and cloned into nucleotide 1257 to 56 fragment of pcDNA3.1(+) plasmid, which was amplified by PCR with a set of primer, 5'-TGCGGATCCAGAGCAGATTGTACTGAGAGT-3'(SEQ ID NO:47) and 5'-CTC-TATCTCGAGTGAGGCGGAAAGAACCA-3'(SEQ ID NO:48). The ligated DNA was used for a template of PCR with primers, 5'-TTTAAGCTTGAAGACTATTTTTACAT-CAGGTTGTTTTTCT-3' (SEQ ID NO:49) and 5'-TT-TAAGCTTGAAGACACGGTGTTTCGTCCTTTCCACA-3'(SEQ ID NO:50). The product was digested with HindIII, which was subsequently self-ligated to produce psiU6BX vector plasmid. For the control, psiU6BX-EGFP was prepared by cloning double-stranded oligonucleotides of
   5'-CACCGAAGCAGCACGACTTCTTCTTCAA-GAGAGAAGAAGTCGTGCTGCTTC-3'(SEQ ID NO:51) and
   5'-AAAAGAAGCAGCACGACTTCTTCTCTCT-TGAAGAAGAAGTCGTGCTGCTTC -3' (SEQ ID NO:52) into the BbsI site in the psiU6BX vector.

Immunoblotting

Cells were washed twice with PBS and harvested in lysis buffer (150 mM NaCl, 1% Triton X-100, 50 mM Tris-HCl pH 7.4, 1 mM DTT, and 1X complete Protease Inhibitor Cocktail (Roche)). After the cells were homogenized and centrifuged at 10,000×g for 30 min, the supernatant were standardized for protein concentration by the Bradford assay (Bio-Rad). Proteins were separated by 10% SDS-PAGE and immunoblotted with mouse anti-Flag, rabbit anti-RNA polymerase II, rabbit anti-HA antibody, and rabbit anti-ZNFN3A1 antibody. HRP-conjugated goat anti-mouse IgG and anti-rabbit IgG (Santa Cruz Biotechnology, Santa Cruz, Calif.) served as the secondary antibody for the ECL Detection System (Amersham Pharmacia Biotech, Piscataway, N.J.).

Immunohistochemistry

Immunohistochemical staining was carried out using anti-ZNFN3A1 antibody. Paraffin-embedded tissue sections were subjected to the SAB-PO peroxidase immunostaining system (Nichirei, Tokyo, Japan) according to the manufacturer's recommended method. Antigens were retrieved from deparaffinized and re-hydrated tissues by pretreating the slides in citrate buffer (pH6) in a microwave oven for 10 mm at 700W. 3-(4,5-dimethylthiazol-2-yl)-2,5-diphenyltetrazolium bromide (MTT) assay Cells were transfected with psiU6BX-siZNFN3A1 or control plasmids and maintained in the culture media supplemented with optimum concentration of geneticin. Six to twelve days after transfection, the medium was replaced with fresh medium containing 500 µg/ml of MTT (3-(4,5-dimethylthiazol-2-yl)-2,5-diphenyl tetrazolium bromide) (Sigma) and the plates were incubated for four hours at 37° C. Subsequently, the cells were lysed by the addition of 1 ml of 0.01 N HCl/10% SDS and absorbance of lysates was measured with an ELISA plate reader at a test wavelength of 570 nm (reference, 630 nm). The cell viability was represented by the absorbance compared to that of control cells.

Flow Cytometry

The effect of ZNFN3A1 in cell cycle progression was determined by flow cytometry. Cells were plated at a density of $1 \times 10^5$ cells/100 mm dish. The cells were trypsinized at the given time course, collected in PBS and fixed in 70% cold ethanol. After RNase treatment, cells were stained with propidium iodide (50 µg/ml) in PBS. Flow cytometry was performed on a Becton Dickinson FACScan and analyzed by CellQuest and ModFit software (Verity Software House), The percentages of nuclei in G0/G1, S and G2/M phases of the cell cycle, and any sub-G1 population were determined from at least 20,000 ungated cells.

To examine the role of ZNFN3A1-siRNAs in cell cycle, $1 \times 10^5$ of SNU475 cells transfected with psiU6BX-ZNFN3A1 or control plasmids were collected by trypsinization at 5 days after transfection. After fixation in 70% cold ethanol, cells were treated with RNase and propidium iodide (50 µg/ml) in PBS, and analyzed by a FACScan (Becton Dickinson, San Jose, Calif.). The percentages of cells in G0/G1, S and G2/M phases of the cell cycle, and any sub-G1 population were determined from at least 20,000 ungated cells using ModFit software (Verity Software House).

EXAMPLE 2

Identification of a Novel Gene Frequently Up-regulated in HCCs

Figure 1B:
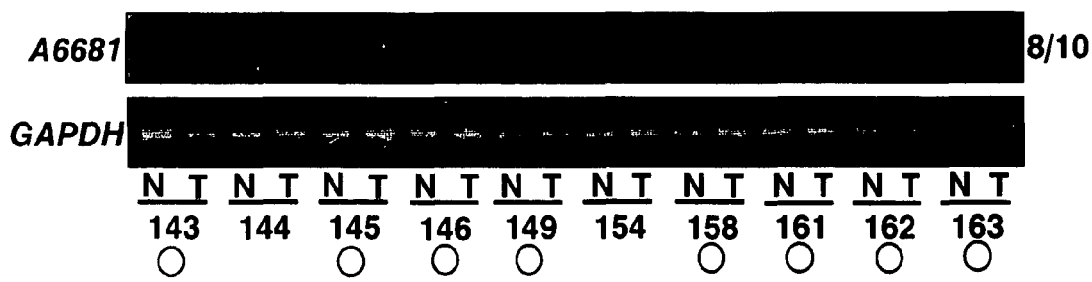

Using genome-wide cDNA microarray with 23040 genes, we identified an expressed sequence tag (EST), which was commonly up-regulated in hepatitis B-positive and/or hepatitis C-positive HCCs. Among them, we focused on a gene, A6681, corresponding to an EST (Hs. 8109), because its expression was significantly up-regulated in eleven of twelve (91.7%) clinical HCCs compared with the corresponding noncancerous liver tissues (FIG. 1A). The elevated expression of the gene A6681 was also confirmed in another 10 HCC cases by RT-PCR (FIG. 1B). The relative expression confirmed by semi-quantitative RT-PCR were well correlated to those confirmed by cDNA microarray.

EXAMPLE 3A

Isolation and Characterization of a Novel Human Gene, ZNFN3A1

Figure 1C:
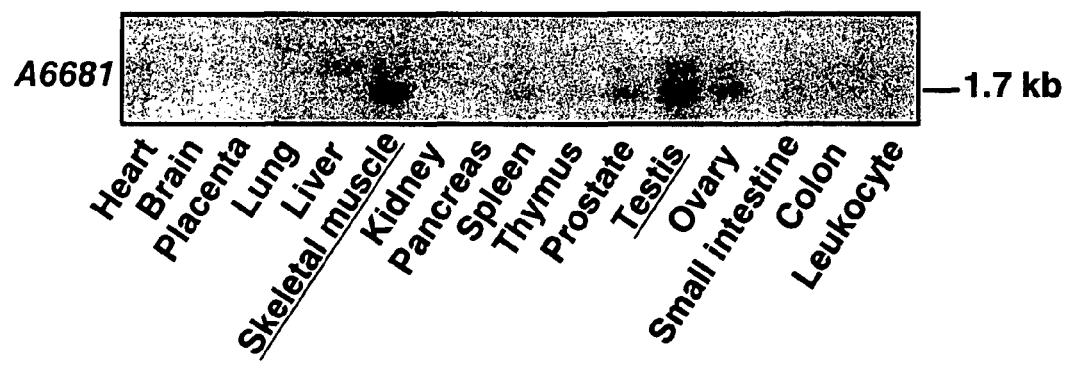

Multi-tissue northern blots from Clonetech were used to hybridize a $^{32}$P labeled partial A6681 cDNA with an approximately 1.7-kb transcript expressed in testis and skeletal muscle purchased from Clontech. (FIG. 1C) The A6681 probe was prepared by RT-PCR using a set of primers, 5'-TTCCCGATATCAACATCTACCAG-3' (SEQ. ID. NO. 32) and 5'-AGTGTGTGACCTCAATAAGGCAT-3'(SEQ. ID. NO. 33). Pre-hybridization, hybridization and washing were performed according to the supplier's recommendations. The blots were autoradiographed with intensifying screens at −80° C. for 24 h. The approximately 1.7 kb polynucleotide transcript was termed the ZNFN3A1 gene.

The sequence of the 5' region of the transcript was determined by 5' rapid amplification of cDNA ends (5'RACE) which was performed using the Marathon cDNA amplification kit by Clontech in accordance with the manufacturer's instructions. For the amplification of the 5' part of ZNFN3A1 cDNA, a gene specific reverse primer (5'-CTGCCAAGAAGTCGGAGTCTGGAG) [SEQ. ID. NO. 34] was used. The cDNA template was synthesized from human testis mRNA by RT-PCR. The PCR products were cloned using TA cloning kit by Invitrogen and their sequences were determined with an ABI PRISM 377 DNA sequencer from Applied Biosystems. As a result, 1622 nucleotides sequence was assembled and obtained as shown and described in SEQ. ID. NO: 1 that contained an open reading frame of 1284 nucleotides encoding 428 amino acids.

Because no EST clones containing the 5' part of the ZNFN3A1 gene was identified in EST data bases: Genomic sequences were searched corresponding to the ZNFN3A1 cDNA in the genomic databases. Cosmid sequences were found in the genomic sequence comparison that were assigned to chromosomal band 1q44, which also included the ZNFN3A1 gene. Using GENSCAN and Gene Recognition (GENSCAN from MIT (http://genes.mit.edu/GENSCAN.html) and GRAIL 2 from IMS (http://www.genome.ad.jp)) and Assembly Internet Link program (AutoAssembler 2.1) provided by ABI, the candidate-exon sequences were predicted and exon-connection was performed.

EXAMPLE 3B

Isolation and Characterization of a Novel Human Protein, ZNFN3A1

Figure 2A:
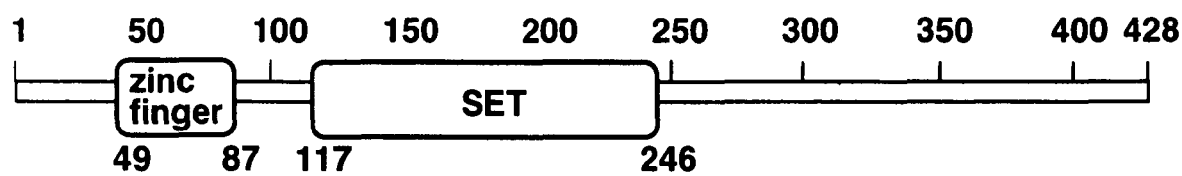
FIG. 2A is an illustration depicting the predicted protein structure and protein motifs of ZNFN3A1. The protein motifs of ZNFN3A1 were predicted by Simple Modular Architecture Research Tool (SMART).
Figures 3M, 3N, 3O, 3P, 3Q, 3R:
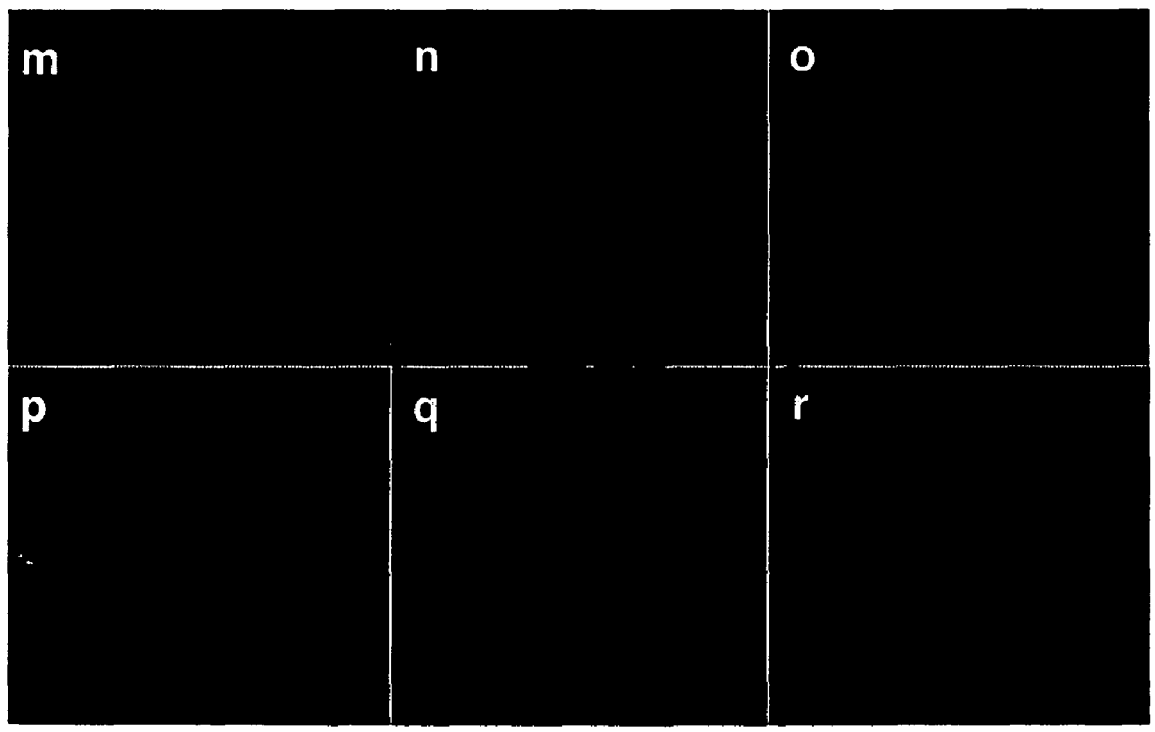

With the 1622 nucleotide sequence that contained an open reading frame encoding 428 amino acids, the protein ZNFN3A1 was identified using a Simple Modular Architecture Research Tool (SMART) from EMBL (http://smart.embl-heidelberg.de). SMART suggested that the ZNFN3A1 protein contained a zf-MYND [zinc finger protein (MYND domain containing)] domain (codons 49-87) as well as a SET [(Su (var) 3-9, Enhancer-of-zeste, Trithorax)] domain (codons 117-246) (FIG. 2A). The amino acid sequence of the ZNFN3A1 protein shared 94% identity with amino acid sequence of the *Mus musculus* ES cells cDNA (GenBank Accession number: AK010447) (FIG. 2B) and the gene encoding the protein was termed "ZNFN3A1"/(zinc finger protein, subfamily 3A (MYND domain containing), 1) by nomenclature committee.

EXAMPLE 4

Sub-cellular Localization of ZNFN3A1

The entire coding region corresponding to ZNFN3A1 was cloned into a pEGFP-N1 vector and a pFLAG-CMV-5a vector, and these constructs were transfected into SNU475 cells and expressed. Expression of EGFP tagged ZNFN3A1 and FLAG tagged ZNFN3A1 was confirmed by western blotting (data not shown). Both ZNFN3A1-EGFP fusion protein and FLAG-tagged ZNFN3A1 protein were detected homogenously in cytoplasm and nucleus by fluorescent immunocytochemistry (FIG. 3A-F). Sub-cellular localization of endogenous ZNFN3A1 protein was observed by using specific antibody against ZNFN3A1.

Interestingly subcellular localization of ZNFN3A1 protein is altered during cell cycle progression or due to the density of cultured cells. Performing immunocytochemistry for endogenous ZNFN3A1 protein, some amount of proteins were localized in nucleus at the case of low cell concentration culture (FIG. 3G-I and FIG. 3M-O). However, in the case of high cell concentration culture, most of ZNFN3A1 protein localized in cytoplasm (FIG. 3J-L and FIG. 3P-R). These results revealed that sub-localization of ZNFN3A1 depends on cell concentration. ZNFN3A1 accumulates in the nucleus when cells are in middle to late S phase or cultured in sparse condition, while ZNFN3A1 localizes in the cytoplasm as well as nucleus when they are in other phases or grown in dense condition.

The immunocytochemistry was performed by fixing cultured cells on chamber slides with PBS containing 4% paraformaldehyde for 15 min, then rendered permeable with PBS containing 0.1% Triton X-100 for 2.5 min at RT. The cells were covered with 2% BSA in PBS for 24 h at 4° C. to block non-specific hybridization and subsequently incubated with mouse anti-FLAG antibody at 1:2000 dilution and rabbit anti-ZNFN3A1 antibody at 1:3000 for the first antibody. Antibodies were stained fluorescent substrate conjugated anti-mouse IgG and anti-rabbit IgG second antibody (ICN/Cappel and Jackson Immuno Research). Nuclei were counter stained by 4',6'-diamidine-2'-phenylindole dihydrochloride (DAPI). Fluorescence image was obtained with an ECLIPSE E800 microscope.

Localization of ZNFN3A1 may be dependant on cell cycle and thus cell cycle was analyzed using flow cytometry in different cell concentration of SNU475 cells. Cells were plated at a density of $1 \times 10^5$ cells/100 mm dish. The cells were trypsinized at the given time course, collected in PBS and fixed in 70% cold ethanol. After RNase treatment, cells were stained with propidium iodide (50 μg/ml) in PBS. Flow cytometry was performed on a Becton Dickinson FACScan and analyzed by CellQuest and ModFit software (Verity Software House). The percentages of nuclei in G0/G1, S and G2/M phases of the cell cycle, and any sub-G1 population were determined from at least 20,000 ungated cells.

Figure 4A:
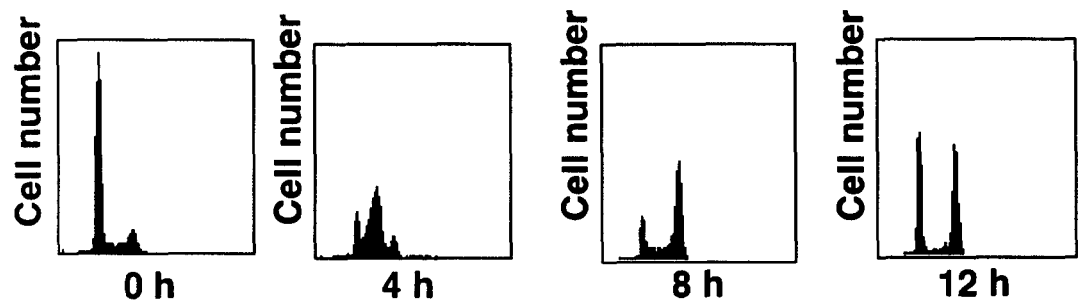
FIGS. 4A and 4B depict the effect of cell cycle progression on the sub-cellular localization of ZNFN3A1.
Figure 4B:

Compared with low cell concentration and high cell concentration, the population of cells in G0/G1 phase increased in the case of high cell concentration, however the population of cells in S and G2/M phase decreased drastically. To determine the effect of cell cycle to localization of ZNFN3A1 in detail, Huh7 cells were synchronized using aphidicolin and sub-cellular localization of ZNFN3A1 was observed (FIG. 4*a, b*). Most of the Huh7 cells stayed G0/G1 phase 36 h after treatment of aphidicolin and the ZNFN3A1 was localized in the cytoplasm. When aphidicolin was removed from culture medium, cell cycle was progressed and ZNFN3A1 protein moved to nucleus from cytoplasm. These data showed that sub-cellular localization of ZNFN3A1 protein was regulated by cell cycle status, and ZNFN3A1 protein moved to nucleus in the proliferative condition.

EXAMPLE 5

Promotion of Growth of Normal Tissue Cell Line NIH3T3 Cells by ZNFN3A1

To analyze the effects of ZNFN3A1 gene transfer on growth of hepatoma cell lines, normal tissue cell line NIH3T3 cells were transfected with an expression plasmid pcDNA3.1 containing sense ZNFN3A1 and antisense-ZNFN3A1.

NIH3T3 cells were transfected by pcDNA3.1 vectors (Invitrogen) containing full coding sequence of ZNFN3A1 using FuGENE 6 transfection reagent according to the supplier's recommendations. Cells were maintained in DMEM containing 10% FBS and 0.9 mg/ml geneticin, and single colonies were selected. Constitutive ZNFN3A1 expression was determined by RT-PCR.

Figure 5A:
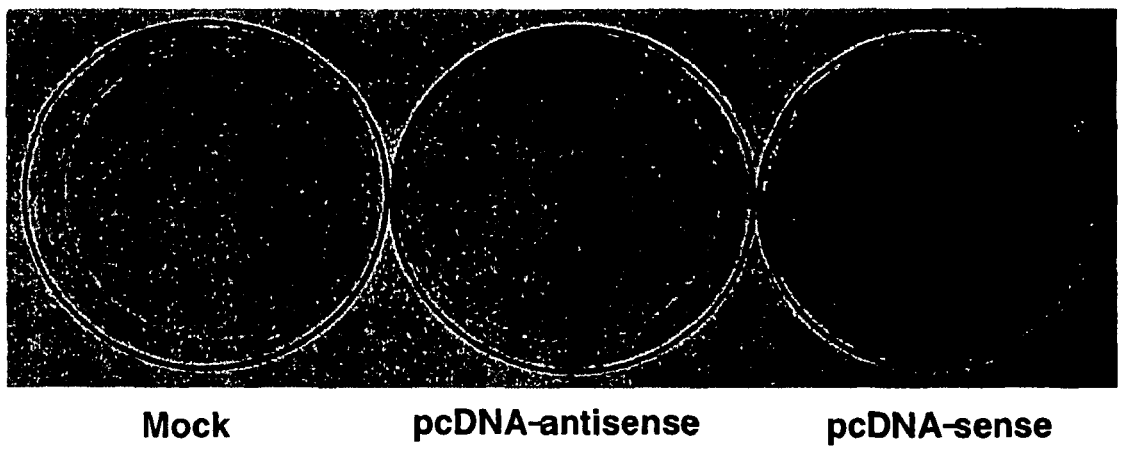
FIGS. 5A-5D depict the growth promoting effect of ZNFN3A1 in NIH3T3.
Figure 5B:
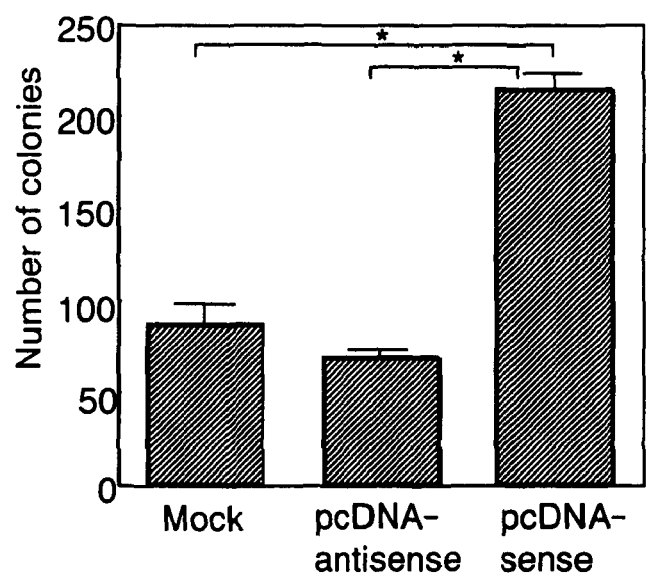

The NIH3T3 cells generally showed no endogenous expression of ZNFN3A1 mRNA. Upon colony formation, the sense ZNFN3A1 expression vector promoted colony formation in NIH3T3 cells compared with mock and antisense-ZNFN3A1 vectors demonstrated no growth as shown in FIGS. 5A, 5B.

Colony formation assays were performed on the plating cells at a density of $1 \times 10^5$ cells/100 mm dish. After 24 h, the cells were transfected by plasmid vector using FuGENE 6 transfection reagent (Roche) and were cultured with appropriate concentration of geneticin for 2 weeks. Cells were fixed with 100% methanol and stained by Giemsa solution. These colony formation assays were confirmed by three independent experiments.

Figure 5C:
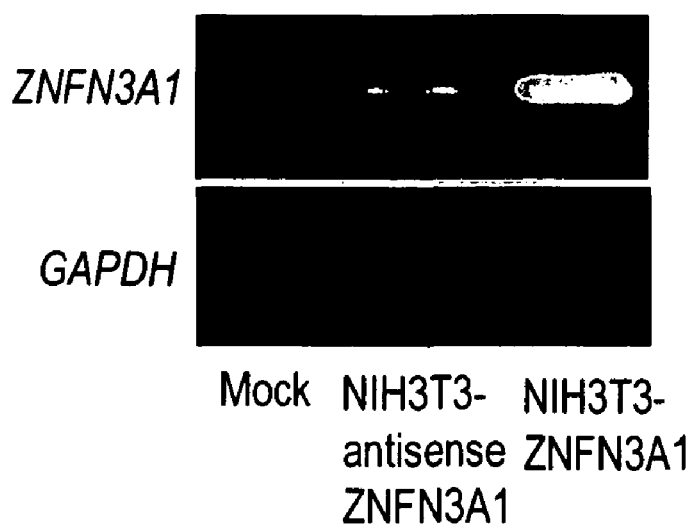
Figure 5D:
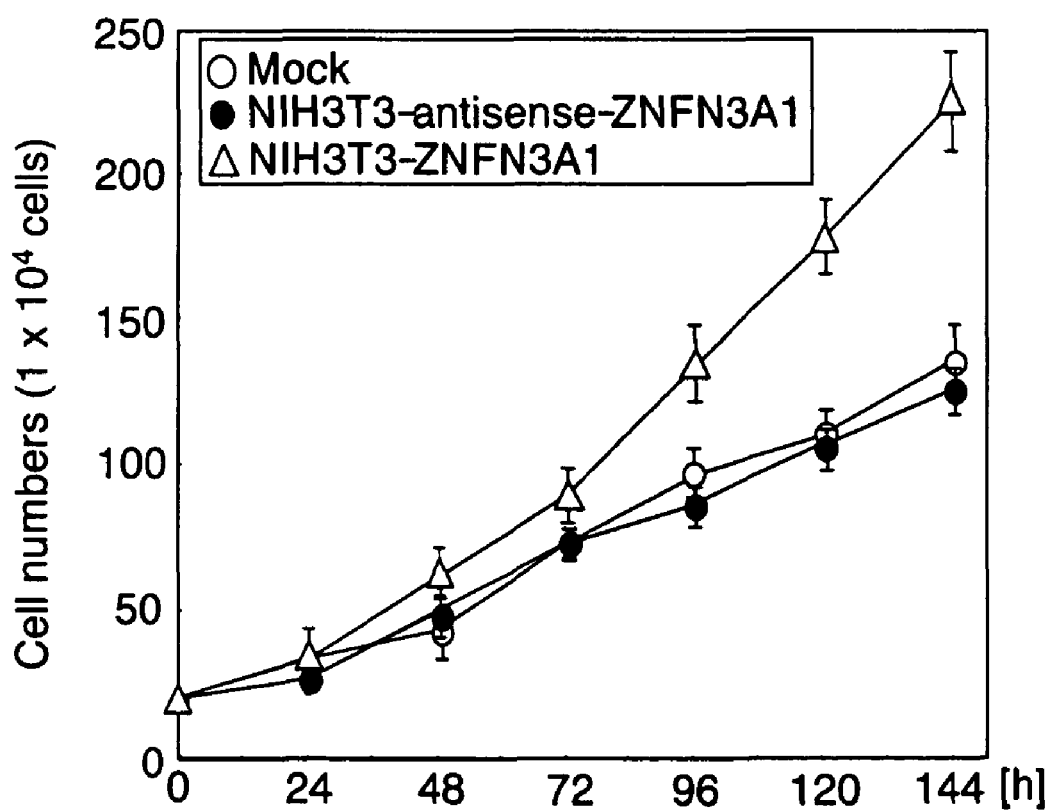

To further investigate the growth promotive effects of ZNFN3A1, stable NIH3T3 transfectant cells of ZNFN3A1 were further examined. The sense ZNFN3A1 stable transfectant cells expressed constitutive ZNFN3A1 mRNA (FIGS. 5C, 5D). Expression was determined by RT-PCR. As shown FIGS. 5C, 5D, the clone which expressed ZNFN3A1 constantly showed high growth ability compared with antisense ZNFN3A1 and control vector transfectant cells showing that ZNFN3A1 plays an important role for growth promotion of hepatocellular carcinoma cells.

EXAMPLE 6

Reduced Expression of ZNFN3A1 by Antisense Oligonucleotides Suppresses Growth of Hepatoma Cells To examine whether suppression of ZNFN3A1 may induce growth retardation and/or cell death to HCC cells, various antisense S-oligonucleotides were synthesized to suppress ZNFN3A1 expression. Sense or antisense S-oligonucleotides of ZNFN3A1 encompassing initiation codon was transfected using LIPOFECTIN Reagent (GIBCO-BRL). The sequences of phosphorothioate-modified ODNs were as follows: antisense S-oligonucleotides; 5'-GCGGGAGGAT GGAGCC (SEQ. ID. NO.29).

The cells were cultured with the antisense and sense S-oligonucleotides for 24 hours, and analyzed for their expression of ZNFN3A1 and ZNFN3A1 by RT-PCR and western blotting using anti-ZNFN3A1 antibody.

Figure 6A:
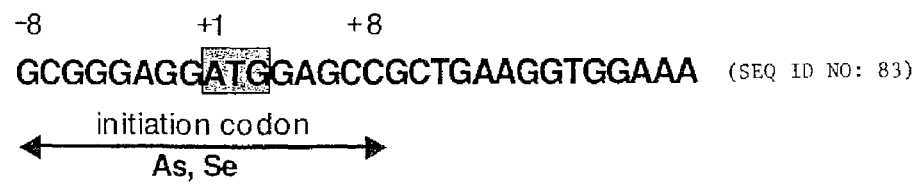
FIGS. 6A-6E depicts the growth suppressive effect of antisense S-oligonucleotides designated to suppress ZNFN3A1.
Figure 6B:
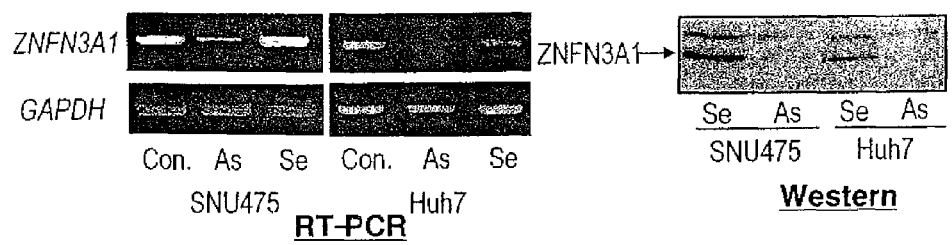

The cells transfected with antisense S-oligonucleotides, encompassing the initiation codon significantly decreased endogenous expression of ZNFN3A1 in SNU475 and Huh7 cells that constitutively express abundant amount of ZNFN3A1 (FIGS. 6A, B). Transfection of antisense S-oligonucleotides also significantly suppressed cell numbers of the Huh7 and SNU475 cells as determined by a colony formation assay as previously described.

An MTT assay was performed by plating cells at a density of $5 \times 10^5$ cells/100 mm dish. On the next day, the cells were transfected in triplicate with sense or antisense S-oligonucleotides of ZNFN3A1. After 72 h of culture, the medium was replaced with 10 ml of fresh medium containing 5 mg 3-(4, 5-dimethylthiazol-2-yl)-2,5-diphenyltetrazolium in bromide (MTT) (SIGMA). After further 4 h of incubation at 37° C., cells were lysed by the addition of 1 ml of 0.01 N HCl/10% SDS. The color reaction was quantified with an ELISA plate reader at a test wavelength of 570 nm (reference, 630 nm). The cell viability was represented by the absorbance compared to the control.

Figure 6C:
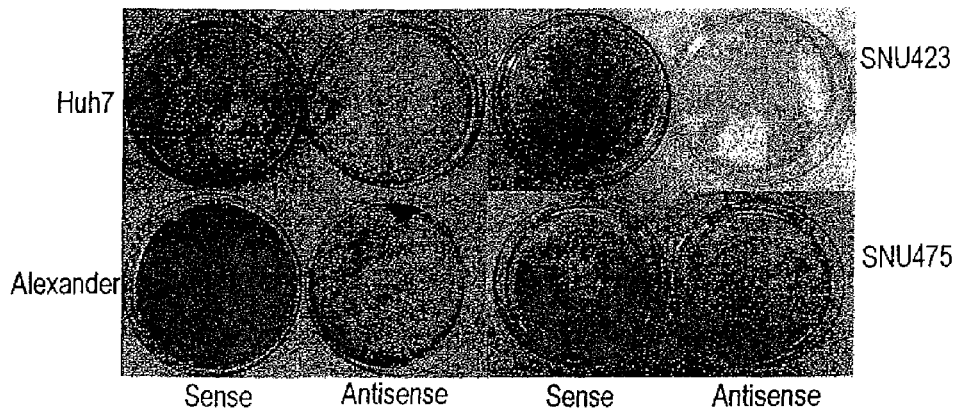
Figure 6D:
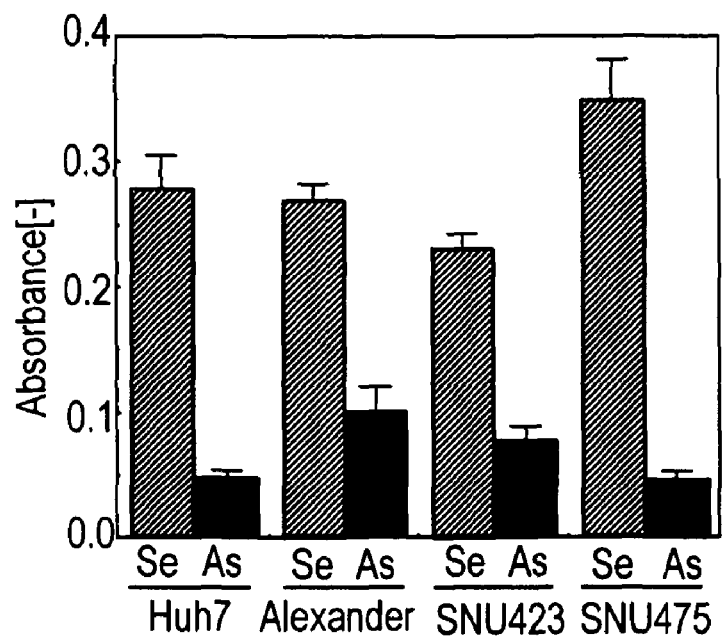
Figure 6E:
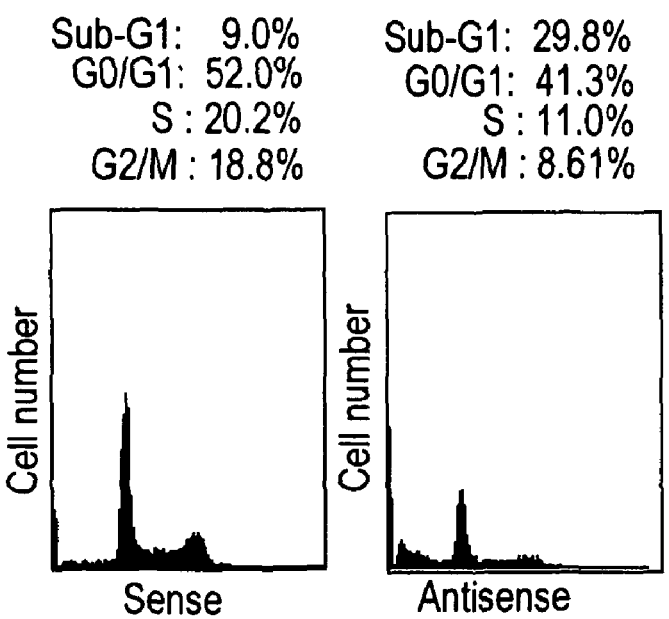

Suppression of cell growth from transfection of antisense-ZNFN3A1 was also seen in other HCC cell lines including Alexander cells and SNU423 cells, both of which also constitutively express abundant amount of ZNFN3A1 compared with that of control S-oligonucleotides as shown in FIGS. 6C, 6D. The results of the colony formation assay was confirmed by three independent experiments. Furthermore, flow-cytometry demonstrated that inhibition of ZNFN3A1 expression significantry decreased numbers of cells in S phase population and increased numbers of sub-G1 phase (FIG. 6E). These results revealed that the suppression of ZNFN3A1 expression induced inhibition of growth and promotion of apoptosis of HCC.

EXAMPLE 7

Interaction of ZNFN3A1 with RNA Helicase KIAA0054

To examine the oncogenic mechanism of ZNFN3A1, ZNFN3A1-interacting proteins were searched using yeast two-hybrid screening system. Yeast two-hybrid assay was performed with MATCHMAKER GAL4 Two-Hybrid System 2 and System 3 by Clontech according to the manufacturer's protocols. The full coding sequence of ZNFN3A1 was cloned in EcoR I site of pAS2-1 as a bait vector. For library screening, a human testis library was cloned in pACT2 (Clontech). Simultaneously co-transformed AH109 yeast cells (with pAS2-1 bait vector and a variety of pACT2 prey vectors) were plated on SD minimal Medium (-Ade/-His/-Leu/-Trp) in addition of 25 mg/L X-α, -Gal (Clontech) and 25 mM 3-amino-1,2,4,-trizole (Sigma). Library plasmid was isolated from the positive colonies and the sequence and the frame was confirmed.

Figure 7A:
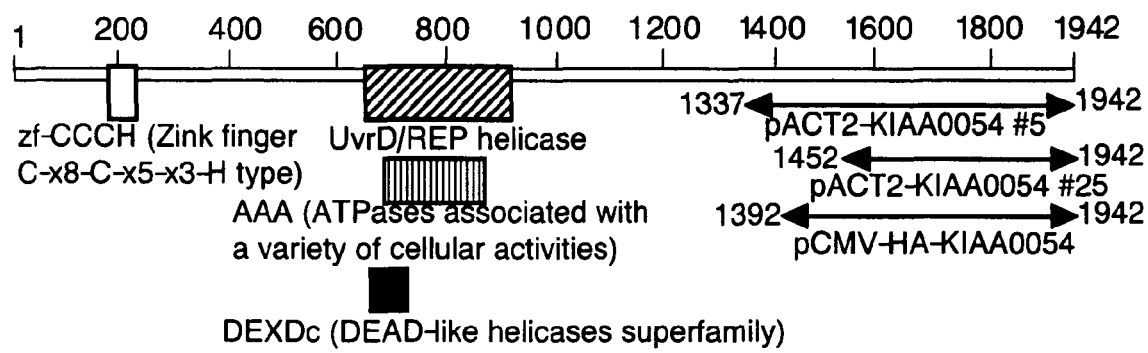
FIGS. 7A-7C depict the interaction between ZNFN3A1 and RNA Helicase KIAA0054.
Figure 7B:
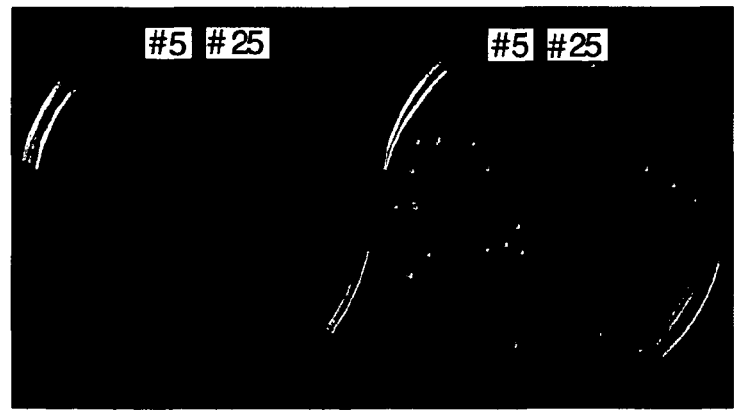

Among the clones identified, the C-terminal region of RNA helicase KIAA0054 interacted with ZNFN3A1 by simultaneous transformation using pAS2.1-ZNFN3A1 and pACT2-KIAA0054 (FIGS. 7A, 7B). RNA helicases constitute a family of proteins that unwind double-stranded RNA by using nucleotide triphosphates as a source of energy. It is clear that RNA helicases are a widely dispersed group of proteins found in virtually all biological processes.

Figure 7C:
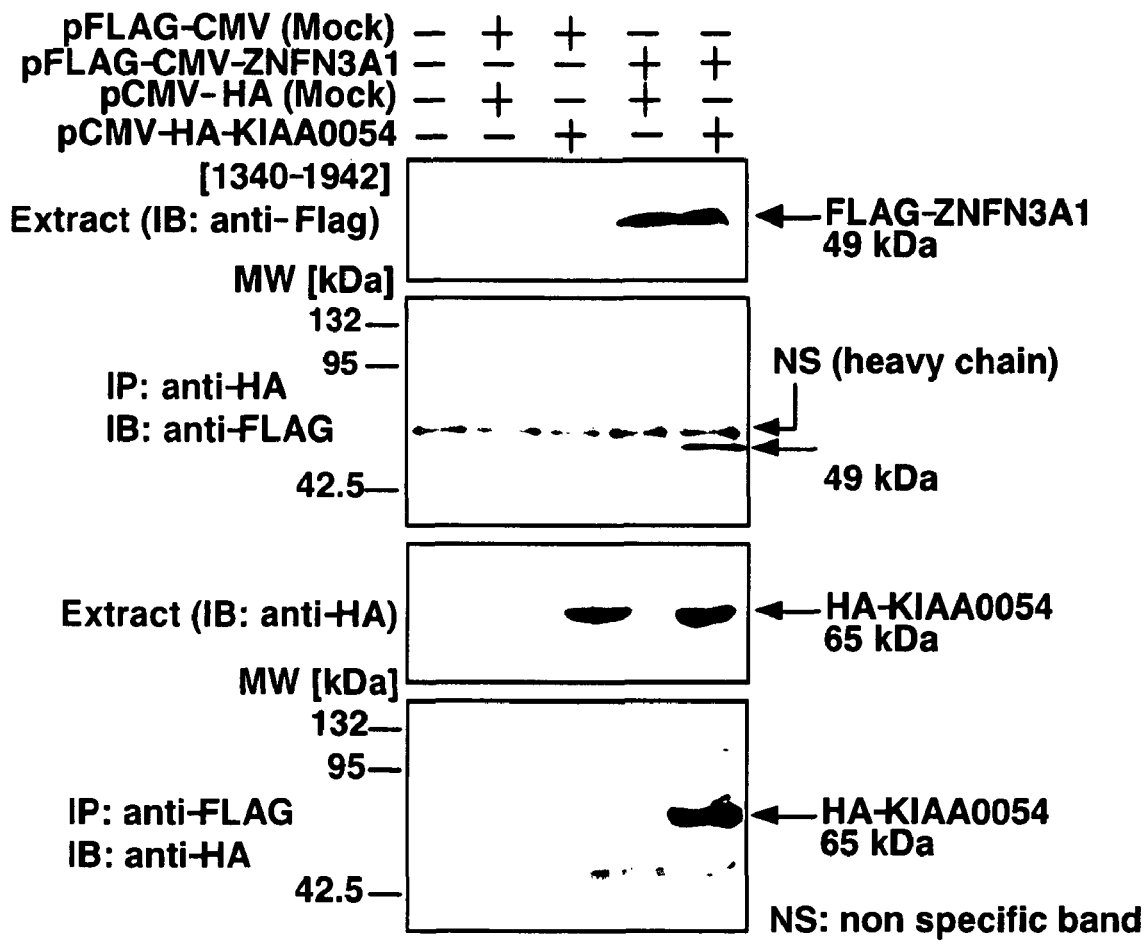

To further confirm the interaction of ZNFN3A1 with KIAA0054, FLAG-tagged ZNFN3A1 protein was prepared. HeLa cells were transfected with 8 μg pFLAG-CMV-ZNFN3A1 and pCMV-HA-KIAA0054 DNA per 10-cm dish and collected after an additional 48 h. Cells were washed once with 10 mM sodium phosphate buffer (pH 7.4) containing 150 mM NaCl (PBS) and lysed in NET-N buffer (150 mM NaCl, 0.5% NP-40, mM Tris-HCl pH8.0, 1 mM EDTA, and 1X complete Protease Inhibitor Cocktail). In a typical immunoprecipitation reaction, 300 µg of the HeLa whole-cell lysate extract was incubated with 1 µg of the desired antibody and 20 p. 1 of protein A or protein G Sepharose beads (Zymed) at 4° C. for 1-2 hr. Beads were washed four times in 1 ml of NET-N buffer. Proteins bound to the beads were eluted by boiling in SDS sample buffer, separated by SDS-PAGE, and transferred to nitrocellulose membranes. The membranes were used for immunoblotting as described above. The lysate was directly analyzed by immunoblotting with anti-FLAG antibody and anti-HA antibody as a control. The ZNFN3A1 protein revealed its association to HA-tagged KIAA0054 protein expressed in HeLa mammalian cells (FIG. 7C).

Figure 8:
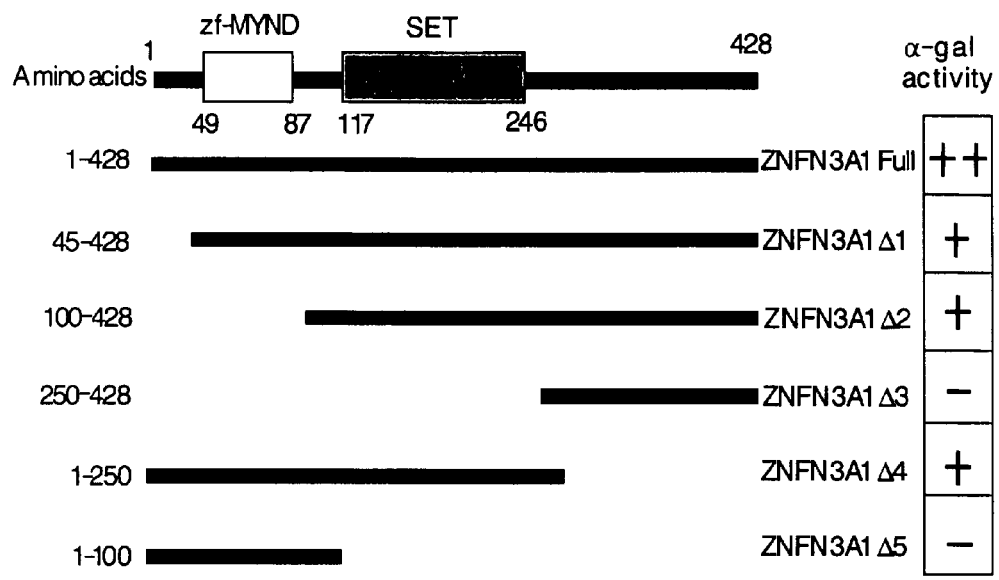
FIG. 8 are photographs demonstrating that the interaction of ZNFN3A1 with KIAA0054 is mediated by SET domain and C-terminal region of KIAA0054. Deletion constructs of ZNFN3A1 were analysed for their ability to interact with KIAA0054 C-terminal region in the two-hybrid system.
Figure 8:
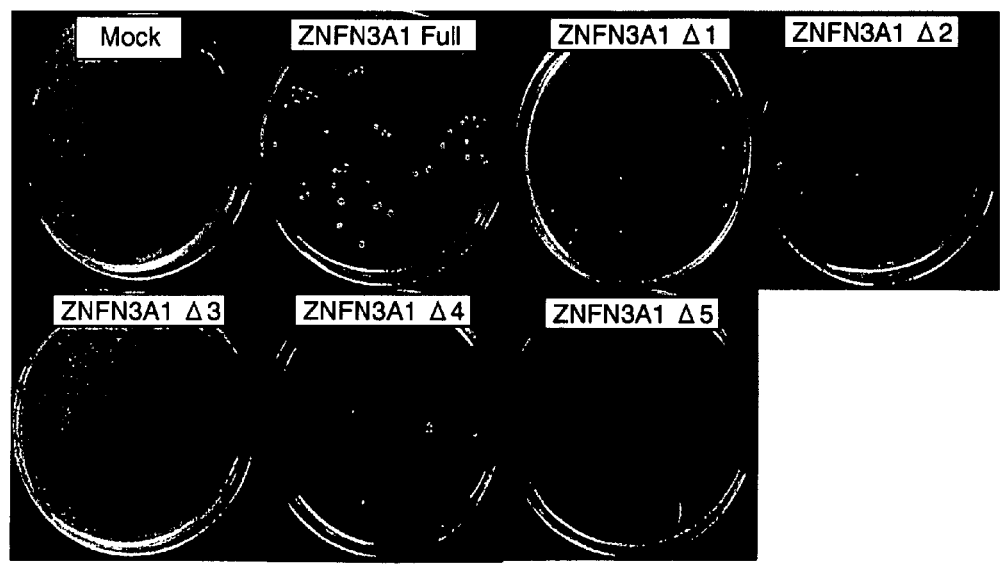

To identify the region of ZNFN3A1 responsible for its interaction with KIAA0054, two-hybrid assay was performed using deletion fragments of ZNFN3A1. Mutants lacking amino acids 1 to 250 or 100 to 428 were negative for interaction with KIAA0054 C-terminal region, whereas a fragment containing amino acids 100 to 250 was positive (FIG. 8). This indicates that the ZNFN3A1-binding region resides in the region of the SET domain.

EXAMPLE 8

Interaction Among ZNFN3A1, RNA Helicase and RNA Polymerase II

Figure 9:
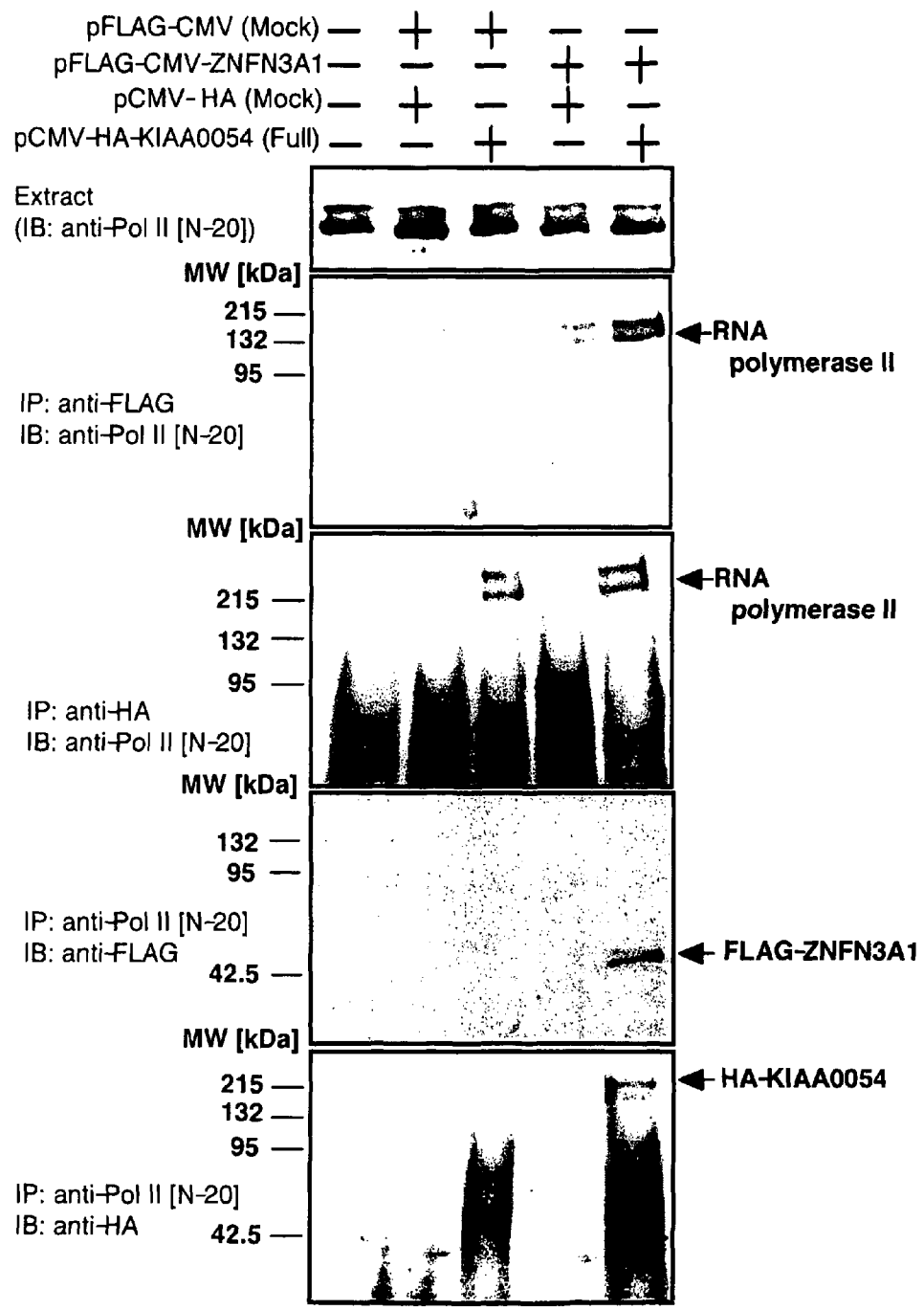
FIG. 9 are photographs showing that RNA helicase KIAA0054 associates with ZNFN3A1 and RNA polymerase II in vivo. Cellular extracts were prepared from HeLa cells transfected with 8 µg of the pFLAG-CMV-ZNFN3A1 (Full) and the pCMV-HA-KIAA0054 (Full length) expression vector. The extracts was immunoprecipitated with anti-RNA polymerase II antibody, anti-HA antibody or anti-FLAG antibody. The immunoprecipitates were analysed by immunoblotting with anti-RNA polymerase II antibody, anti-HA antibody or anti-FLAG antibody. Lysate was directly analysed by immunoblotting as a control.

RNA helicase plays a crucial role for transcription by binding to transcription factor and RNA polymerase II. These results revealed that there was a possibility that zinc finger protein ZNFN3A1 regulated transcription through association with not only RNA helicase KIAA0054 but also RNA polymerase II. The association among ZNFN3A1, RNA helicase KIAA0054 and RNA polymerase II was tested by co-immunoprecipitation (FIG. 9). HeLa cells were transfected with 8 µg pFLAG-CMV-ZNFN3A1 and pCMV-HA-KIAA0054 DNA per 10-cm dish and collected after an additional 48 h. Cells were washed once with 10 mM sodium phosphate buffer (pH 7.4) containing 150 mM NaCl (PBS) and lysed in NET-N buffer (150 mM NaCl, 0.5% NP-40, 20 mM Tris-HCl pH8.0, 1 mM EDTA, and 1X complete Protease Inhibitor Cocktail). In a typical immunoprecipitation reaction, 300 µg of whole-cell extract was incubated with 1 µg of antibody and 20 µl of protein A or protein G Sepharose beads (Zymed) at 4° C. for 1-2 hr. Beads were washed four times in 1 ml of NET-N buffer. Proteins bound to the beads were eluted by boiling in SDS sample buffer, separated by SDS-PAGE, and transferred to nitrocellulose membranes. The membranes were used for immunoblotting as described above.

Figure 12:
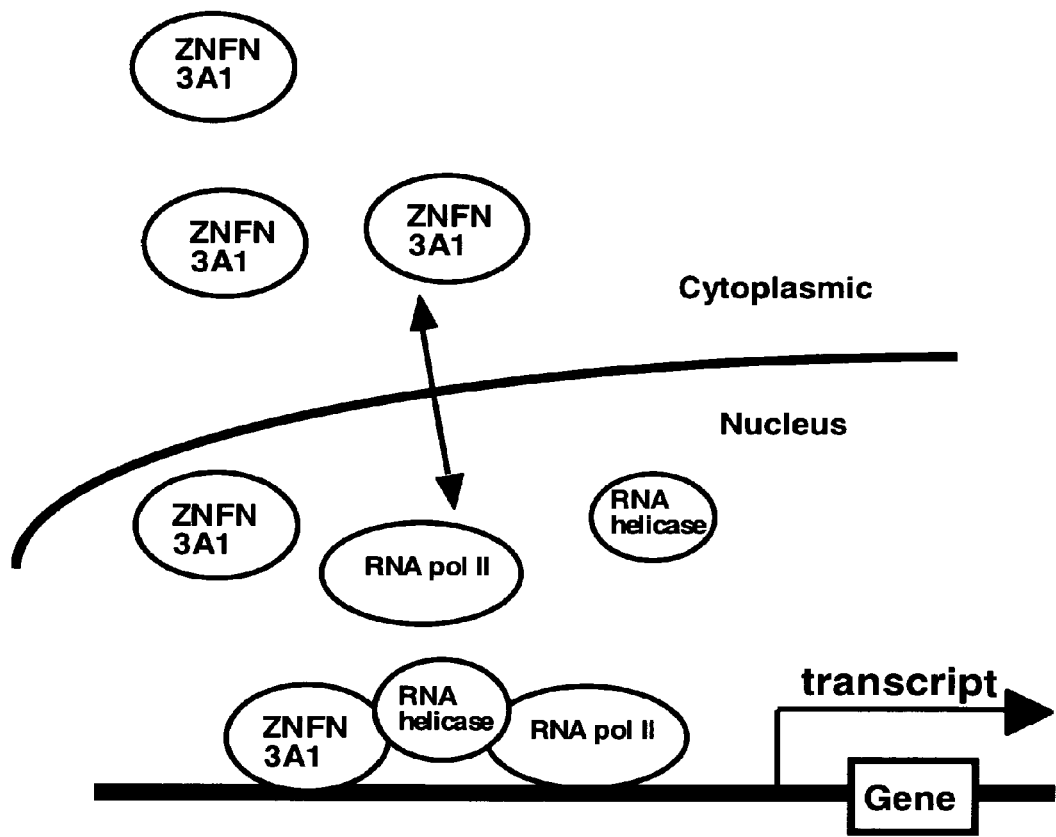
FIG. 12 is an illustration of complex formed between ZNFN3A1, RNA helicase, and RNA polymerase II to regulate transcription of gene.

An association with endogenous RNA polymerase II was detected by using anti-FLAG antibody, anti-HA antibody and anti-RNA polymerase II antibody. When an anti-FLAG antibody was used for immunoprecipitation and an anti-RNA polymerase II antibody was used for immunoblotting, RNA polymerase II specific band was detected strongly in the case of expressing FLAG-ZNFN3A1 protein and HA-KIAA0054 protein together, and detected marginally in the case of expressing only FLAG-ZNFN3A1 protein. On the other hand, when anti-HA antibody was used for immunoprecipitation and anti-RNA polymerase II antibody was used for immunoblotting, RNA polymerase specific band was detected strongly not only in the case of expressing FLAG-ZNFN3A1 protein and HA-KIAA0054 protein together, but also expressing HA-KIAA0054 alone. Moreover, co-immunoprecipitation was worked reversely by changing antibody for immunoprecipitation and immunoblotting. The results were similar in the case of using opposite antibody. These results show that RNA helicase KIAA0054 can mediate complex formation between ZNFN3A1 protein and RNA polymerase II via contacts with each protein. Thus, transcriptional regulation by ZNFN3A1, RNA helicase KIAA0054 and RNA polymerase II may play an important role for promotion of cell growth in hepatocellular carcinogenesis. FIG. 12 is an illustration of complex formed between ZNFN3A1, RNA helicase, and RNA polymerase II to regulate transcription of gene.

EXAMPLE 9

Sequence-specific Binding of ZNFN3A1 Protein

Figures 10A, 10B:
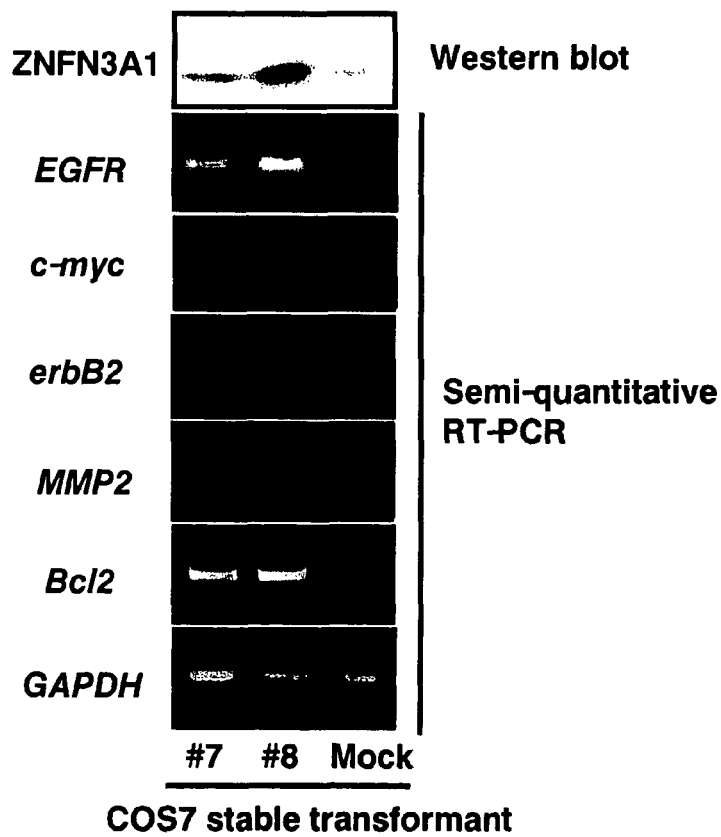
FIGS. 10A and 10B demonstrate that candidate downstream genes regulated by ZNFN3A1.

A consensus DNA binding site for ZNFN3A1 was determined by using an oligonucleotide construct containing a core of 20 random nucleotides. The putative consensus sequences were searched that were able to associate with ZNFN3A1 protein in vitro by means of DNA selection using random oligonucleotides. A GST-ZNFN3A1 fusion protein was prepared and immobilized with Sepharose 4B, and double-stranded random oligonucleotide DNAs were selected that associated with the protein. After ten times of selection and subsequent amplification, the amplified DNA was cloned into pCR vector (Clontech) and 92 clones were sequenced. Among the 92 clones, 32 (34.8%) contained a consensus sequence of 5'-CCCTCC-3', which is 102-fold higher incidence than calculated probability (FIG. 10A). To prepare recombinant protein expressing the zinc finger domain of ZNFN3A1, a cDNA fragment corresponding codons full length of ZNFN3A1 was amplified by RT-PCR using a set of primers, 5'-CGGAATTCATGGAGCCGCT-GAAGGTGGAAAAG-3' [SEQ. ID. NO. 35] and 5'-CCGCTCGAGGGATGCTCTGATGTTGGCGTCG-3' [SEQ. ID. NO. 36], which was subcloned into an appropriate cloning site of pGEX-6P plasmid. Recombinant fusion protein was prepared and purified by Sepharose 46 column as described previously. Oligonucleotides with the sequence "5'-GGGAGAATTCCGACACGCGT(N20)CTC-GAGCGTCTACATGGATCCTCA-3'" [SEQ. ID. NO. 37], were used for selection and amplification as previously described.

By using Eukaryotic Promoter Database (http://www.epd.isb-slb.ch/index.html), candidate downstream genes of ZNFN3A1 was searched and five candidate genes were picked. First, the expression level of each genes was determined by semi-quantitative RT-PCR in COS 7 stable transformant that expressed ZNFN3A1 exogenousiy (FIG. 10B). These results revealed that the expression of EGFR, c-myc and Bcl2 was up-regulated by ZNFN3A1.

Four putative binding sites for ZNFN3A1, whose consensus target sequence is 5'-(C)CCCTCC(T) or (A)GGAGGG(G)-3', were identified in the 5' flanking region of EGFR, between −213-bp and −207-bp (CBS1), between −106-bp and −100-bp (CBS2), between −65-bp and −59-bp (CBS3) and between −46-bp and −40-bp (CBS4). A wild-type reporter plasmid (P1) containing CBS1 CBS2, CBS3, and CBS4 as well as four deletion constructs of the plasmid (P2, P3, P4 and P5) were prepared by cloning each sequence into the appropriate enzyme sites of pGL3-Basic vector (Promega). Plasmids P1, P2, P3, P4 and P5 were constructed by amplification of

P1-F (5'-GGGGTACCCAGTGCTGGGAACGC-CCCTCTCG-3') [SEQ. ID. NO. 38],

P2-F (5'-GGGGTACCCACTCCCGCCGGAGACTAG-GTCC-3') [SEQ. ID. NO. 39],

3-F (5'-GGGGTACCCTCGCATTCTCCTCCTCCTCTGC-3') [SEQ. ID. NO. 40],
4-F (5'-GGGGTACCTGGTCCCTCCTCCTCCCGCCCTG-3') [SEQ. ID. NO. 41] or
P5-F (5'-GGGGTACCTCCCGCCCTGCCTCCCGCGC-CTC-3') [SEQ. ID. NO. 42]
with the same reverse primer (P1-R; 5'-GAAGATCTAG GTGGCCTGTC GTCCGGTCTG G-3') [SEQ. ID. NO. 43]. Site-directed mutagenesis was carried out for both putative ZNFN3A1 binding sites, replacing CCCTCC by CATTCC using the QuickChange Site-Directed Mutagenesis Kit according to the supplier's recommendations (Stratagene).

Each reporter plasmid (2 µg) was co-transfected with 0.2 µg of pRL-TK plasmid (Promega) using FuGENE6 Reagent (Boehringer) according to the manufacturer's instructions. Luciferase assays were carried out using a Dual-Luciferase Reporter Assay System (Promega) following the manufacturer's protocol.

EXAMPLE 10

Up-regulation of EGFR Promoter Activity by ZNFN3A1

Figure 11A:
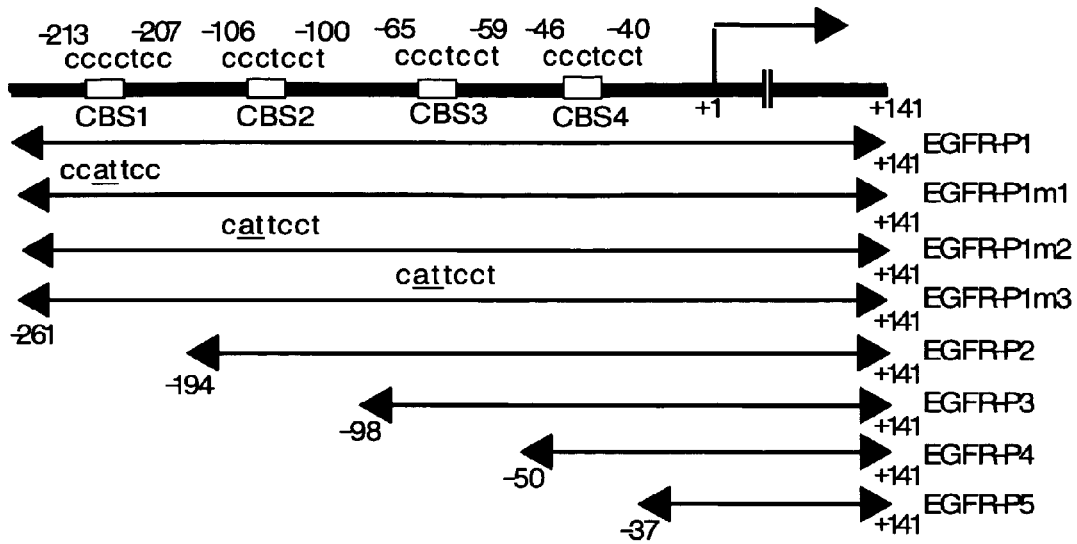
FIG. 11A is a schematic presentation of various reporter plasmids containing putative ZNFN3A1-binding elements in the 5' flanking region of EGFR. Nucleotide positions relative to the putative transcription-initiating site are indicated by plus or minus numbers.
Figure 11B:
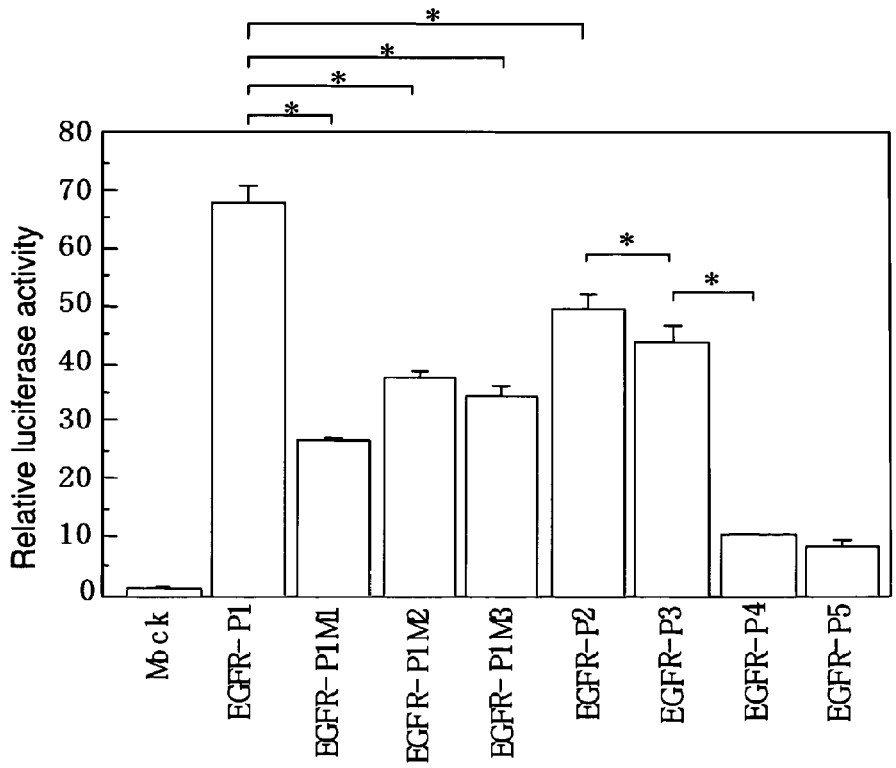
FIG. 11B is a bar chart depicting the results of an assay of the EGFR promoter in SNU475 cells using the indicated reporter plasmids. Bars, SD. *, a significant difference (p<0.05) as determined by a Fisher's protected least-significant test.

Since enhanced expression of EGFR had been reported in HCCs, we focused on that receptor molecule and tested whether its promoter was regulated by the ZNFN3A1-binding sequences. We identified four possible ZNFN3A1-binding motifs (CBS1, 2, 3 and 4) in its 5' flanking region and prepared reporter plasmids containing the four motifs (P1) as well as various deletion forms (P2, P3, P4 and P5). When these reporter plasmids were transfected into SNU475 cells, the activity of P1 was significantly higher than that of P2, P3, P4 or P5. Given the fact that the activity of P4 was very similar to that of P5, we suspected that a region between −261 and −50, containing CBS1, CBS2 and CBS3, might be associated with transcriptional activation of EGFR. To disclose the roles of these domains, we constructed reporter plasmids containing mutant CBS1 (P1 m1) and mutant CBS2 (P1m2) or mutant CBS3 (P1m3) in which each of the candidate binding motifs was changed from 5'-CCCTCC-3' to 5'-CATTCC-3' (FIG. 11A). Reporter assays revealed that fragments containing mutated motifs (P1m1, P1m2 and P1m3) activated transcription of EGFR much more weakly than did P1 (FIG. 11B). These results implied that the three putative ZNFN3A1-binding motifs were involved in transcriptional activation of EGFR.

EXAMPLE 11

Production and Characterization of Plasmids Expressing ZNFN3A1 siRNAs

The entire coding sequence of ZNFN3A1 was amplified with a set of primers, 5'-GGGGTACCAGGATGGAGC-CGCTGAAGGTGG-3'(SEQ ID NO:53), and 5'-GGGAAT-TCTTAGGATGCTCTGATGTTGGCGTCG-3' (SEQ ID NO:54) and cloned into the appropriate cloning sites of pcDNA 3.1(+) vector (Invitrogen) (pcDNA-ZNFN3A1). Plasmids expressing ZNFN3A1-siRNAs were prepared by cloning of double-stranded oligonucleotides into psiU6BX vector.
The nucleotide sequence of the siRNAs were designed using an siRNA design computer program available from the Ambion website. (http://www.ambion.com/techlib/misc/siRNA_finder.html). The computer program selects nucleotide sequences for siRNA synthesis based on the following protocol.

Selection of siRNA Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl, et al. recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with the binding of the siRNA endonuclease complex.
2. Compare the potential target sites to the human genome database and eliminate from consideration any target sequences with significant homology to other coding sequences. The homology search can be performed using BLAST, which can be found on the NCBI server at: www.ncbi.nlm.nih.gov/BLAST/.
3. Select qualifying target sequences for synthesis. At Ambion, preferably several target sequences can be selected along the length of the gene for evaluation.

The oligonucleotides used for ZNFN3A1 siRNAs are shown below. psiU6BX-ZNFN3A1 1-13 (siRNA 1-13) were prepared by cloning the following double-stranded oligonucleotide into the Bbsl site of the psiU6 vector. The corresponding nucleotide position relative to the ZNFN3A1 nucleic acid sequence of SEQ ID NO:1 is listed for each oligonucleotide sequence. Each oligionucleotide is a combination of a sense nucleotide sequence and an antisense nucleotide sequence of the target sequence ZNFN3A1. The nucleotide sequences of the hairpin loop structure and target sequence of siRNA1 to 13 are shown in SEQ ID NO:55 to SEQ ID NO:67 and SEQ ID NO:68 to SEQ ID NO:80, respectively (endonuclease recognition sites are eliminated from each hairpin loop structure sequence).

psiU6BX-ZNFN3A1-1/siRNA1: (Nucleotide Numbers 426-446 of SEQ ID NO:1)

```
                                              (SEQ ID NO: 3)
5'- CACCAAACTTATGGATGGAGCACCTTTCAAGAGAAGGTGCTCCATC
CATAAGTTT-3'
and
                                              (SEQ ID NO: 4)
5'- AAAAAAACTTATGGATGGAGCACCTTCTCTTGAAAGGTGCTCCATC
CATAAGTTT-3'
``` psiU6BX-ZNFN3A1-2/siRNA2: (Nucleotide Numbers 451-471 of SEQ ID NO:1)

```
                                              (SEQ ID NO: 5)
5'- CACCAATCAGAGAAGCTTTACTCATTTCAAGAGAATGAGTAAAGCT
TATATGATT-3'
and
                                              (SEQ ID NO: 6)
5'-AAAAAATCAGAGAAGCTTTACTCATTCTCTTGAAATGAGTAAAGCT
TATATGATT-3'
``` psiU6BX-ZNFN3A1-3/siRNA3: (Nucleotide Numbers 495-515 of SEQ ID NO:1)

(SEQ ID NO: 7)
5'-CACCAACAAACTGACTGAAGATAAGTTCAAGAGAAGGTGCTCCATCCATAAGTTT-3'
and (SEQ ID NO: 8)
5'-AAAAACAAACTGACTGAAGATAAGTCTCTTGAAGGTGCTCCATCCATAAGTTT-3' psiU6BX-ZNFN3A1-4/siRNA4: (Nucleotide Numbers 532-552 of SEQ ID NO:1)

(SEQ ID NO: 9)
5'-CACCAACTCGTAATGACATTTCAACTTCAAGAGAGTTGAAATGTCATTACGAGTT-3'
and (SEQ ID NO: 10)
5'-AAAAACTCGTAATGACATTTCAACTCTCTTGAAGTTGAAATGTCATTACGAGTT-3' psiU6BX-ZNFN3A1-5/siRNA5: (Nucleotide Numbers 623-643 of SEQ ID NO:1)

(SEQ ID NO: 11)
5'-CACCAAAGTGATCTGCAACTCTTTTCAAGAGAAAAGAGTTGCAGATCACTTTT-3'
and (SEQ ID NO: 12)
5'-AAAAAAAGTGATCTGCAACTCTTTTCTCTTGAAAAAGAGTTGCAGATCACTTTT-3' psiU6BX-ZNFN3A1-6/siRNA6: (Nucleotide Numbers 625-645 of SEQ ID NO:1)

(SEQ ID NO: 13)
5'-CACCAAGTGATCTGCAACTCTTTCATTCAAGAGATGAAAGAGTTGCAGATCACTT-3'
and (SEQ ID NO: 14)
5'-AAAAAAGTGATCTGCAACTCTTTCATCTCTTGAATGAAAGAGTTGCAGATCACTT-3' psiU6BX-ZNFN3A1-7/siRNA7: (Nucleotide Numbers 636-656 of SEQ ID NO:1)

(SEQ ID NO: 15)
5'-CACCAACTCTTTCACCATCTGTAATTTCAAGAGAATTACAGATGGTGAAAGAGTT-3'
and (SEQ ID NO: 16)
5'-AAAAACTCTTTCACCATCTGTAATTCTCTTGAAATTACAGATGGTGAAAGAGTT-3' psiU6BX-ZNFN3A1-8/siRNA8: (Nucleotide Numbers 726-746 of SEQ ID NO:1)

(SEQ ID NO: 17)
5'-CACCAACTGTTCGATTGTGTTCAATTTCAAGAGAATTGAACACAATCGAACAGTT-3'
and (SEQ ID NO: 18)
5'-AAAAACTGTTCGATTGTGTTCAATTCTCTTGAAATTGAACACAATCGAACAGTT-3' psiU6BX-ZNFN3A1-9/siRNA9: (Nucleotide Numbers 906-926 of SEQ ID NO:1)

(SEQ ID NO: 19)
5'-CACCAAGGATGCTGATATGCTAACTTTCAAGAGAAGTTAGCATATCAGCATCCTT-3'
and (SEQ ID NO: 20)
5'-AAAAAGGATGCTGATATGCTAACTTCTCTTGAAAGTTAGCATATCAGCATCCTT-3' psiU6BX-ZNFN3A1-10/siRNA10: (Nucleotide Numbers 923-943 of SEQ ID NO:1)

(SEQ ID NO: 21)
5'-CACCAACTGGTGATGAGCAAGTATGTTCAAGAGACATACTTGCTCATCACCAGTT-3'
and (SEQ ID NO: 22)
5'-AAAAACTGGTGATGAGCAAGTATGTCTCTTGAACATACTTGCTCATCACCAGTT-3' psiU6BX-ZNFN3A1-11/siRNA11: (Nucleotide Numbers 937-957 of SEQ ID NO:1)

(SEQ ID NO: 23)
5'-CACCAAGTATGGAAGGAAGTTCAAGTTCAAGAGACTTGAACTTCCTTCCATACTT-3'
and (SEQ ID NO: 24)
5'-AAAAAGTATGGAAGGAAGTTCAAGTCTCTTGAACTTGAACTTCCTTCCATACTT-3' psiU6BX-ZNFN3A1-12/siRNA12: (Nucleotide Numbers 1065-1085 of SEQ ID NO:1)

(SEQ ID NO: 25)
5'-CACCAACATCTACCAGCTGAAGGTGTTCAAGAGACACCTTCAGCTGGTAGATGTT-3'
and (SEQ ID NO: 26)
5'-AAAAACATCTACCAGCTGAAGGTGTCTCTTGAACACCTTCAGCTGGTAGATGTT-3' psiU6BX-ZNFN3A1-13/siRNA13: (Nucleotide Numbers 1258-1278 of SEQ ID NO:1)

```
                                       (SEQ ID NO: 27)
5'-CACCAAGCAATGAAGAATCTGAGACTTCAAGAGAGTCTCAGATTCTT
CATTGCTT-3'
```
and

```
                                       (SEQ ID NO: 28)
5'-AAAAAAGCAATGAAGAATCTGAGACTCTCTTGAAGTCTCAGATTCTT
CATTGCTT-3'
``` psiU6BX-siZNFN3A1 or psiU6BX-mock plasmids were transfected with pcDNA-ZNFN3A1 into COS 7 cells using FuGENE6 reagent according to the supplier's recommendations (Roche). The plasmids were solely transfected into SNU479 cells expressing abundant amount of endogenous ZNFN3A1. Whole extracts of the cells were lysed 2 days after the transfection and utilized for immunoblot analysis.

Figure 14:
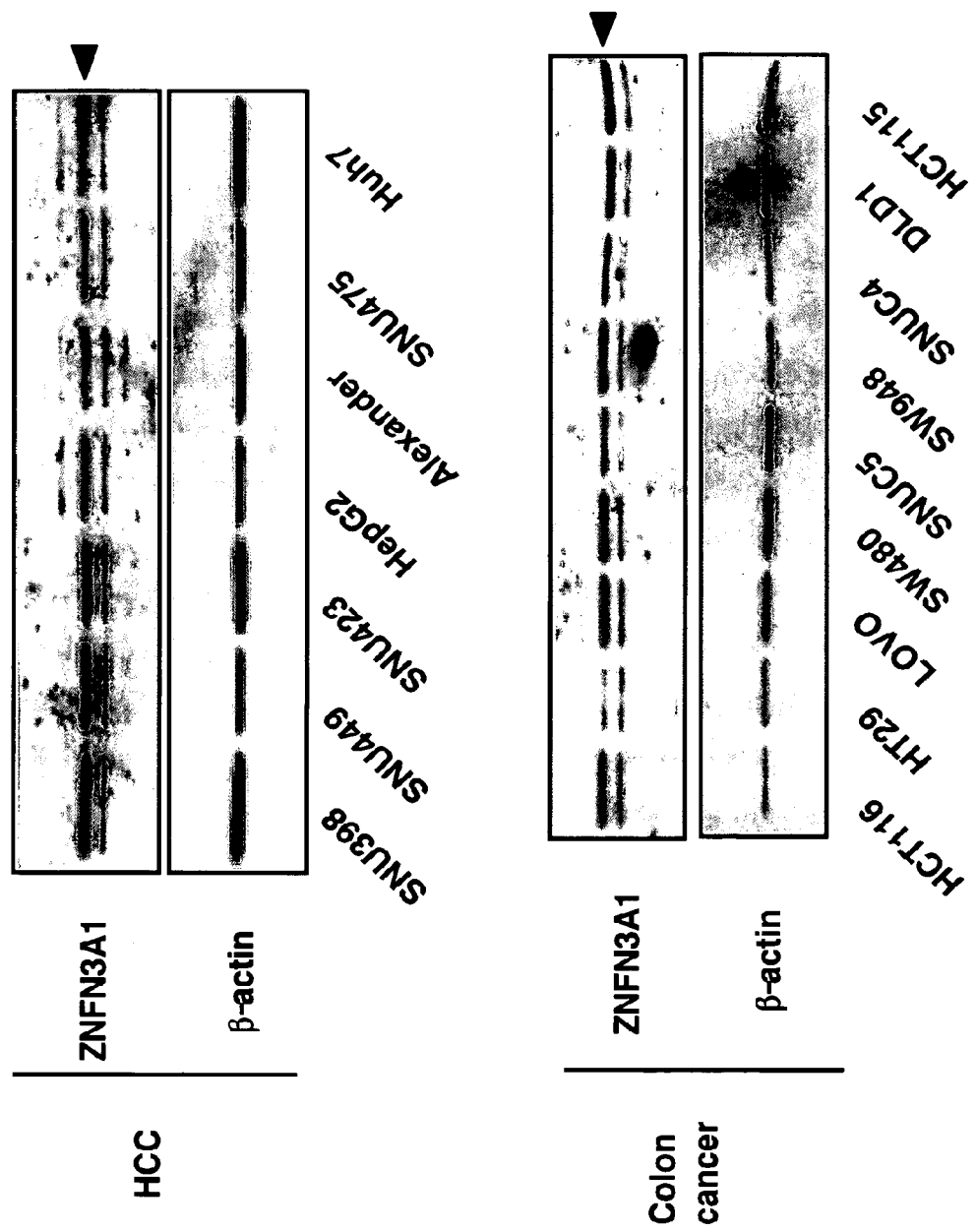
FIG. 14 is a photograph of an immunoblot showing the expression of ZNFN3A1 protein in hepatoma and colon cancer cell lines.
Figure 15:
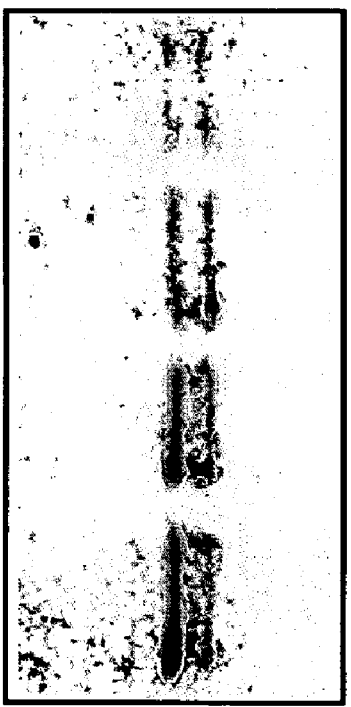
FIG. 15 is a photograph of an immunoblot showing the effect of ZNFN3A1-siRNAs on endogeneous ZNFN3A1 expression in SNU475 cell transfected with psiU6BX-ZNFN3A1-1, -4, -12 or psiU6BX-mock plasmids.
Figure 15:

Among the 13 different expression plasmids expressing ZNFN3A1 siRNAs, psiU6BX-ZNFN3A1-8, -12, and -13 most significantly reduced expression of exogenous ZNFN3A1 by western blot analysis, when they were transfected into COS 7 cells together with pcDNA-ZNFN3A1. Among other plasmids, psiU6BX-ZNFN3A1-4 showed marked reduction, and psiU6BX-ZNFN3A1-2, -5, -6, -7 and -10 exerted moderate suppression, whereas psiU6BX-ZNFN3A1-1, -3, -9 and -11 had no or little effect on the expression (FIG. 13). To further examine RNAi activity of ZNFN3A1 siRNAs, we transfected psiU6BX-ZNFN3A1-1, -4, -12, or psiU6BX-mock into SNU475 cells that express abundant amount of ZNFN3A1 (FIG. 14). Western blot analysis using the extracts of transfected cells demonstrated marked reduction of endogenous ZNFN3A1 by psiU6BX-ZNFN3A1-12, and moderate suppression by psiU6BX-ZNFN3A1-4 compared to cells transfected with psiU6BX-mock. On the other hand transfection with psiU6BX-ZNFN3A1-1 did not affect expression of ZNFN3A1 (FIG. 15).

EXAMPLE 11

Growth Suppression of Hepatoma and Colon Cancer Cells by ZNFN3A1 siRNA

Figure 16B:
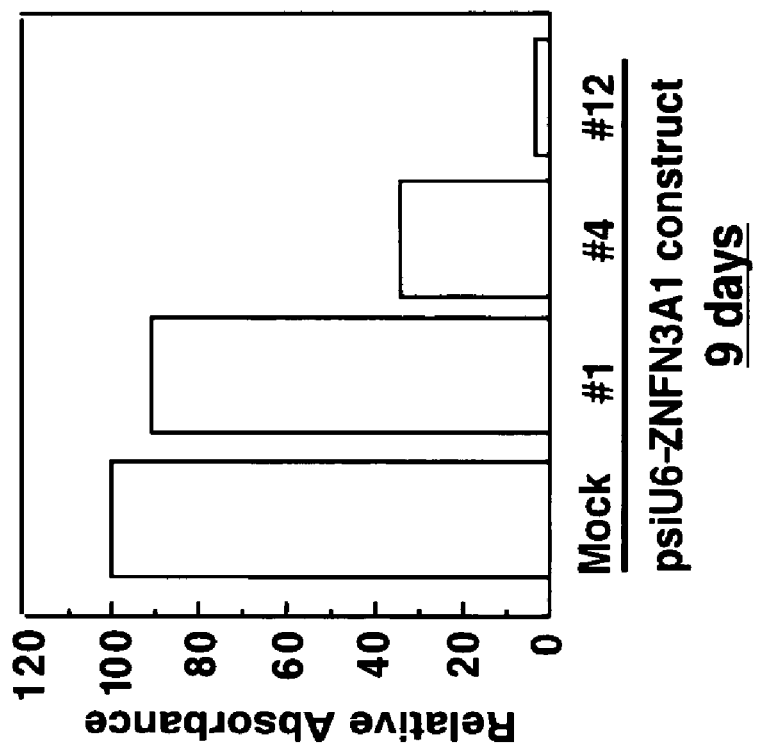
FIG. 16 A-B are bar charts showing the effect of ZNFN3A1-siRNAs on cell growth in SNU475 cells. Viability of transfected cells was measured by MTT assay 6 (Panel A) and 9 (panel B) days after the transfection.
Figure 16A:
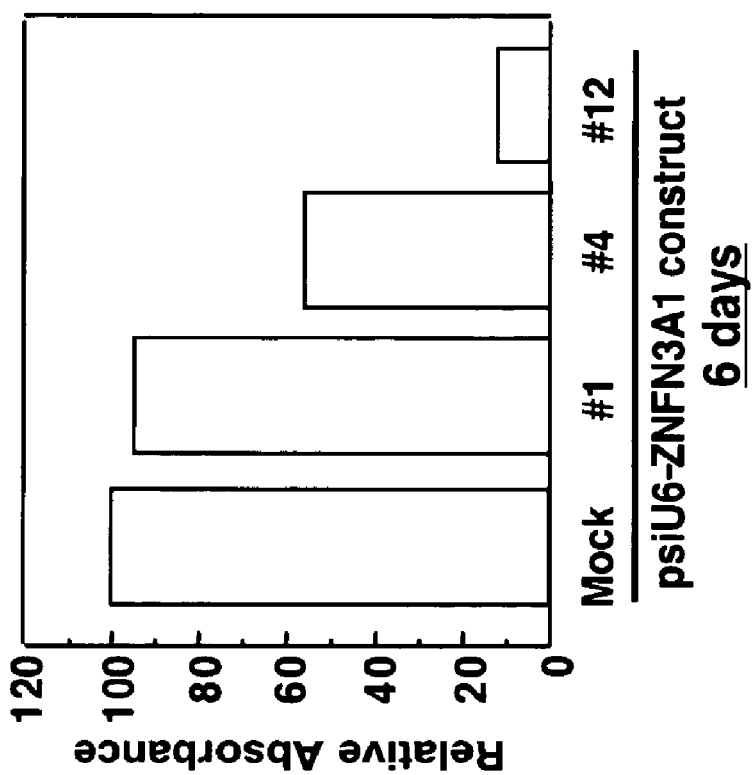
Figure 17A:
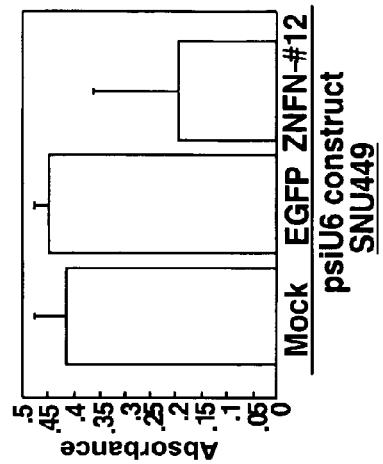
FIG. 17 A-H are bar charts showing growth suppressive effect of ZNFN3A1-siRNAs in various human hepatoma and colon cancer cells. Viability of transfected cells was measured by MTT assay, 9 to 12 days after the transfection.
Figure 17B:
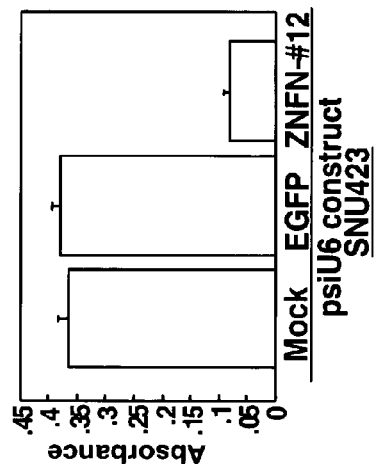
Figure 17C:
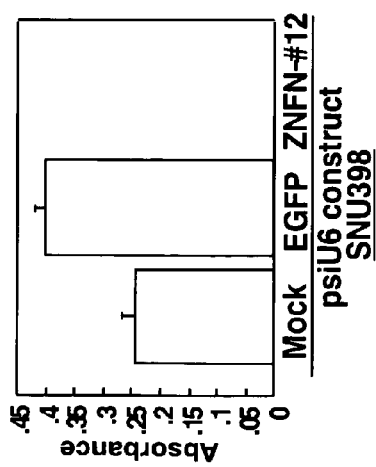
Figure 17D:
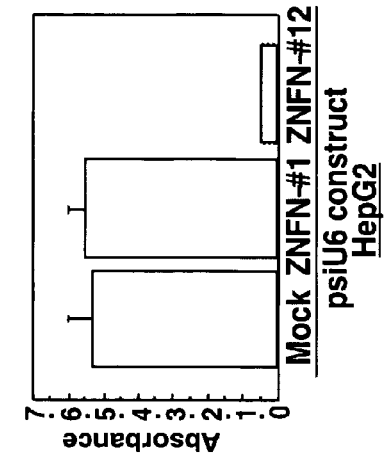
Figure 17E:
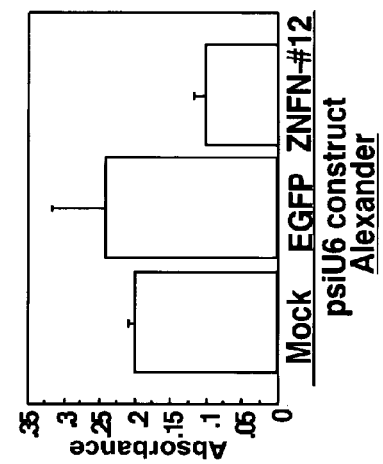
Figure 17F:
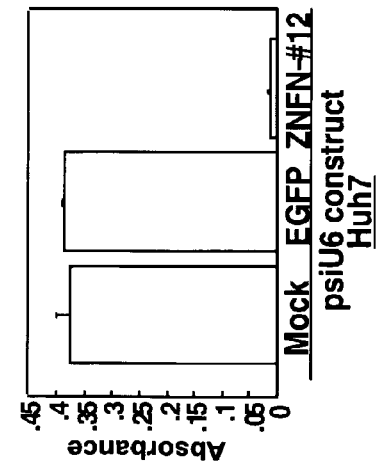
Figure 17H:
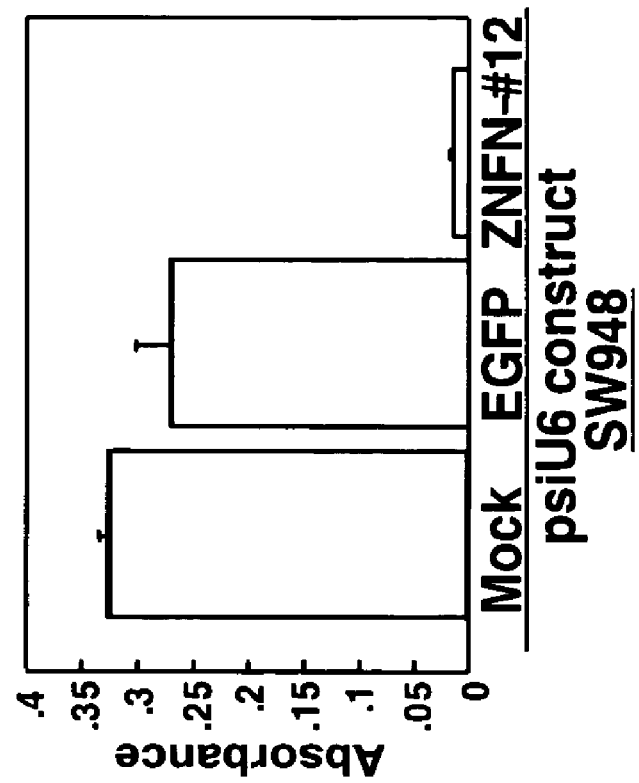
Figure 17G:
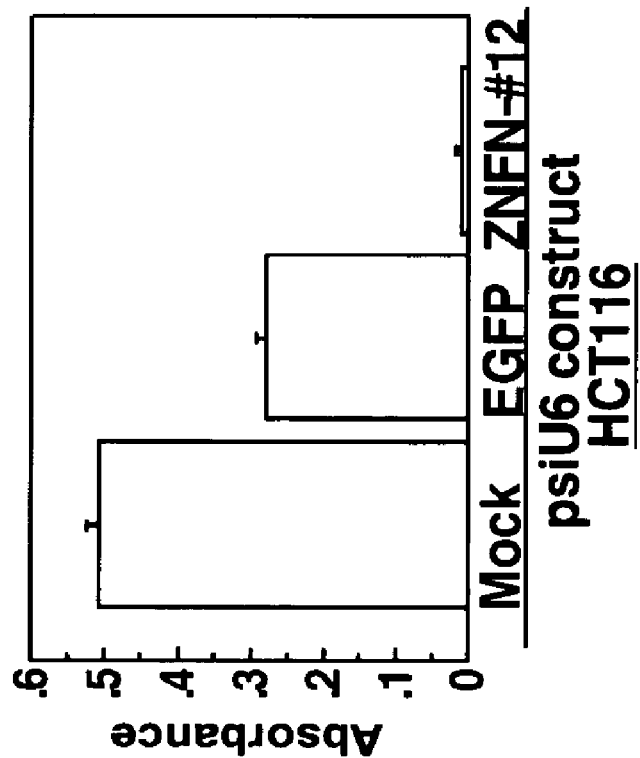
Figure 18:
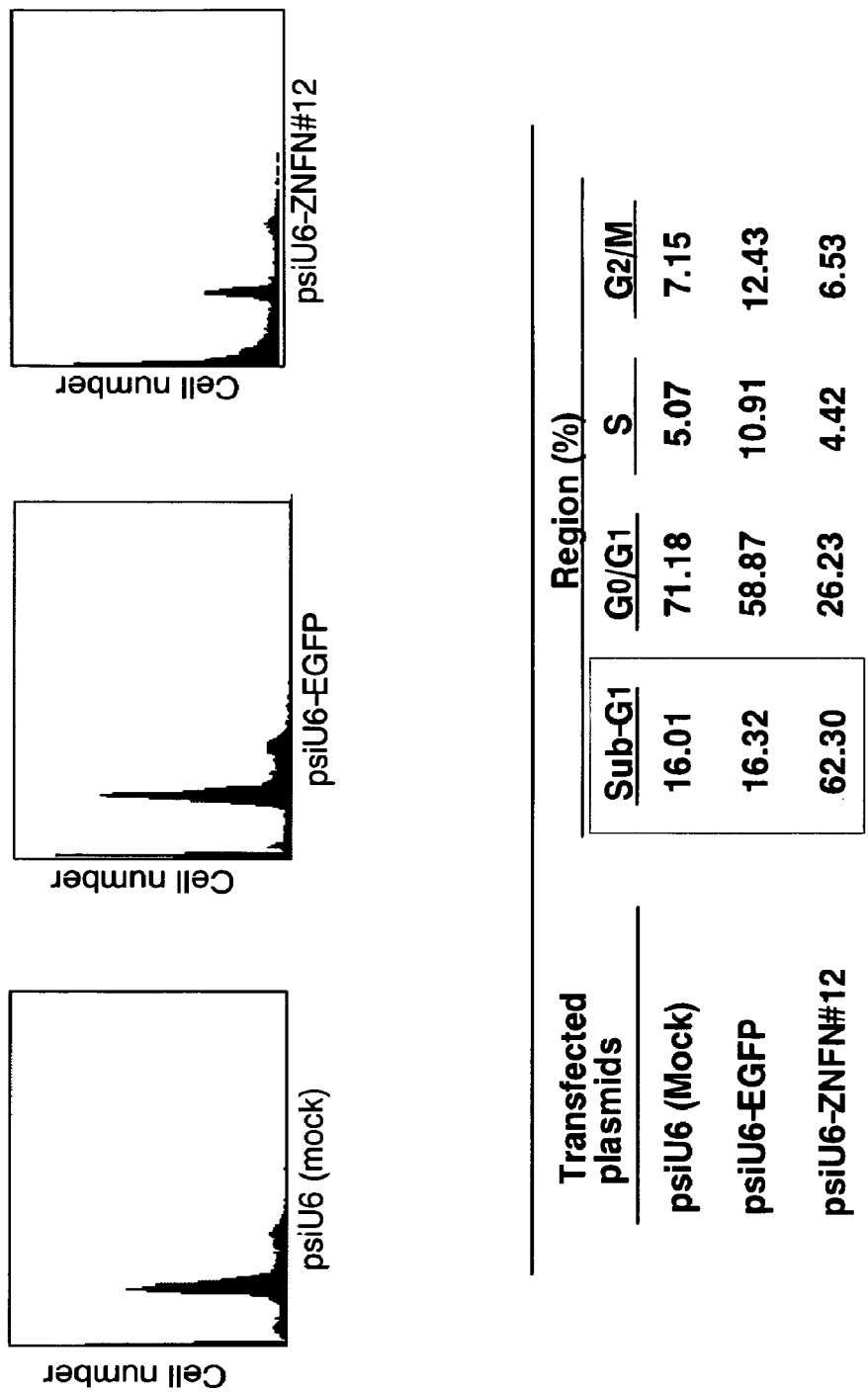
FIG. 18 is an illustration showing induction of apoptosis in response to ZNFN3A1-siRNAs in SNU475 cell detected by FACS analysis.

To test whether suppression of ZNFN3A1 may result in growth suppression of hepatoma cells, SNU475 cells were transfected with either psiU6BX-ZNFN3A1-12, the vector that demonstrated the most knock down effect on the expression; psiU6BX-ZNFN3A1-4 which demonstrated mild silencing effect; psiU6BX-ZNFN3A1-1 which demonstrated no silencing effect, or psiU6BX-mock. MTT assays at both 6 days and 9 days of transfection showed that psiU6BX-ZNFN3A1-12 has the highest growth inhibitory effect and that psiU6BX-ZNFN3A1-1 did not change the number of surviving cells compared with cells transfected with psiU6BX-mock (FIG. 16). The growth inhibitory effect of the plasmids was correlated to their gene silencing activity. To further demonstrate the growth inhibitory effect of ZNFN3A1-siRNAs, psiU6BX-ZNFN3A1-12; psiU6BX-EGFP For the control, psiU6BX-EGFP was prepared by cloning the following double-stranded oligonucleotide 5'-CACCGAAGCAGCACGACTTCTTCTTCAA-GAGAGAAGAAGTCGTGCT GCTTC-3' (SEQ ID NO:51) and 5'-AAAAGAAGCAGCACGACTTCTTCTCTCT-TGAAGAAGAAGTCGTGCT GCTTC -3' (SEQ ID NO:52) into the BbsI site of the psiU6BX vector.

or psiU6BX-mock was transfected into various hepatoma cell lines including SNU398, SNU423, SNU449, Huh7, Alexander, and HepG2 and two colon cancer cell lines, SW948 and HCT116. Transfection of psiU6BX-ZNFN3A1-12 significantly reduced number of surviving cells compared with that of psiU6BX-EGFP or psiU6BX-mock (FIG. 17). Furthermore, FACS analysis demonstrated that transfection of psiU6BX-ZNFN3A1-12 increased the number of cells in sub-G1 phase (FIG. 18). These results indicate that ZNFN3A1 contributes to aberrant cell growth and/or survival in a wide range of human cancer cells.

INDUSTRIAL APPLICABILITY

The expression of novel human gene ZNFN3A1 is markedly elevated in hepatocellular carcinoma as compared to non-cancerous liver tissues. Accordingly, this gene may serve as a diagnostic marker of HCC and the protein encoded thereby may be used in diagnostic assays therefore.

The present inventors have also shown that the expression of novel protein ZNFN3A1 promotes cell growth whereas cell growth is suppressed by antisense oligonucleotides corresponding to the ZNFN3A1. These findings suggest that ZNFN3A1 stimulates oncogenic activity. Thus, this novel oncoprotein is a useful target for the development of anti-cancer pharmaceuticals. For example, agents that block the expression of ZNFN3A1 or prevent its activity may find therapeutic utility as anti-cancer agents, particularly anti-cancer agents for the treatment of HCC. Examples of such agents include antisense oligonucleotides, siRNAs, and antibodies that recognize ZNFN3A1.

Furthermore, the present inventors have shown that ZNFN3A1 directly associates with an RNA helicase and forms a complex with RNA polymerase II. This complex then activates transcription of downstream target genes, including EGFR, through direct binding of the complex with an element "(C)CCCTCC(T)" in the 5' flanking region. Thus, agents that inhibit the activity of the complex may also find utility in the treatment and prevention of HCC.

While the invention has been described in detail and with reference to specific embodiments thereof, it will be apparent to one skilled in the art that various changes and modifications can be made therein without departing from the spirit and scope of the invention.

The invention claimed is:

1. A method of diagnosing hepatocellular carcinoma, wherein said method comprises the steps of:
   (a) determining an expression level of the ZNFN3A1 gene consisting of the nucleotide sequence of SEQ ID NO:1 in a liver tissue sample derived from a subject;
   (b) comparing the expression level of the ZNFN3A1 gene with that of a normal sample, and
   (c) defining an increased expression level of the ZNFN3A1 gene in the sample compared to that of the normal sample as having hepatocellular carcinoma.

* * * * *

UNITED STATES PATENT AND TRADEMARK OFFICE
CERTIFICATE OF CORRECTION

PATENT NO. : 8,148,080 B2
APPLICATION NO. : 12/727370
DATED : April 3, 2012
INVENTOR(S) : Yusuke Nakamura et al.

It is certified that error appears in the above-identified patent and that said Letters Patent is hereby corrected as shown below:

In the Specifications:

Column 34, line 62, that portion reading "Nucleotide Sequence of the psiU6BX6 Plasmid" should read --Nucleotide Sequence of the psiU6BX6 Plasmid Part 1--.

Column 35, line 14, that portion reading "GAAACACC- - - -TTTTTACATCA" should read --GAAACACC--.

Column 35, line 15, should read --Nucleotide Sequence of the psiU6BX6 Plasmid Part 2 (SEQ ID NO: 84) TTTTTACATCA--.

Signed and Sealed this
Ninth Day of July, 2013

Teresa Stanek Rea
*Acting Director of the United States Patent and Trademark Office*

SEQUENCE LISTING

<160> NUMBER OF SEQ ID NOS: 84

<210> SEQ ID NO 1
<211> LENGTH: 1622
<212> TYPE: DNA
<213> ORGANISM: Homo sapiens

```
<220> FEATURE:
<221> NAME/KEY: CDS
<222> LOCATION: (96)..(1382)

<400> SEQUENCE: 1
gtgcgcgcag ggcgcaggcg cgcgggtccc ggcagcccgt gagacgcccg ctgctggacg        60
cgggtagccg tctgaggtgc cggagctgcg ggagg atg gag ccg ctg aag gtg          113
                                      Met Glu Pro Leu Lys Val
                                        1               5 gaa aag ttc gca acc gcc aac agg gga aac ggg ctg cgc gcc gtg acc         161
Glu Lys Phe Ala Thr Ala Asn Arg Gly Asn Gly Leu Arg Ala Val Thr
           10                  15                  20 ccg ctg cgc ccc gga gag cta ctc ttc cgc tcg gat ccc ttg gcg tac         209
Pro Leu Arg Pro Gly Glu Leu Leu Phe Arg Ser Asp Pro Leu Ala Tyr
    25                  30                  35 acg gtg tgc aag ggg agt cgt ggc gtc gtc tgc gac cgc tgc ctt ctc         257
Thr Val Cys Lys Gly Ser Arg Gly Val Val Cys Asp Arg Cys Leu Leu
40                  45                  50 ggg aag gaa aag ctg atg cga tgc tct cag tgc cgc gtc gcc aaa tac         305
Gly Lys Glu Lys Leu Met Arg Cys Ser Gln Cys Arg Val Ala Lys Tyr
55                  60                  65                  70 tgt agt gct aag tgt cag aaa aaa gct tgg cca gac cac aag cgg gaa         353
Cys Ser Ala Lys Cys Gln Lys Lys Ala Trp Pro Asp His Lys Arg Glu
                75                  80                  85 tgc aaa tgc ctt aaa agc tgc aaa ccc aga tat cct cca gac tcc gtt         401
Cys Lys Cys Leu Lys Ser Cys Lys Pro Arg Tyr Pro Pro Asp Ser Val
            90                  95                 100 cga ctt ctt ggc aga gtt gtc ttc aaa ctt atg gat gga gca cct tca         449
Arg Leu Leu Gly Arg Val Val Phe Lys Leu Met Asp Gly Ala Pro Ser
        105                 110                 115 gaa tca gag aag ctt tac tca ttt tat gat ctg gag tca aat att aac         497
Glu Ser Glu Lys Leu Tyr Ser Phe Tyr Asp Leu Glu Ser Asn Ile Asn
    120                 125                 130 aaa ctg act gaa gat aag aaa gag ggc ctc agg caa ctc gta atg aca         545
Lys Leu Thr Glu Asp Lys Lys Glu Gly Leu Arg Gln Leu Val Met Thr
135                 140                 145                 150 ttt caa cat ttc atg aga gaa gaa ata cag gat gcc tct cag ctg cca         593
Phe Gln His Phe Met Arg Glu Glu Ile Gln Asp Ala Ser Gln Leu Pro
                155                 160                 165 cct gcc ttt gac ctt ttt gaa gcc ttt gca aaa gtg atc tgc aac tct         641
Pro Ala Phe Asp Leu Phe Glu Ala Phe Ala Lys Val Ile Cys Asn Ser
            170                 175                 180 ttc acc atc tgt aat gcg gag atg cag gaa gtt ggt gtt ggc tta tat         689
Phe Thr Ile Cys Asn Ala Glu Met Gln Glu Val Gly Val Gly Leu Tyr
        185                 190                 195 ccc agt atc tct ttg ctc aat cac agc tgt gac ccc aac tgt tcg att         737
Pro Ser Ile Ser Leu Leu Asn His Ser Cys Asp Pro Asn Cys Ser Ile
    200                 205                 210 gtg ttc aat ggg ccc cac ctc tta ctg cga gca gtc cga gac atc gag         785
Val Phe Asn Gly Pro His Leu Leu Leu Arg Ala Val Arg Asp Ile Glu
215                 220                 225                 230 gtg gga gag gag ctc acc atc tgc tac ctg gat atg ctg atg acc agt         833
Val Gly Glu Glu Leu Thr Ile Cys Tyr Leu Asp Met Leu Met Thr Ser
                235                 240                 245 gag gag cgc cgg aag cag ctg agg gac cag tac tgc ttt gaa tgt gac         881
Glu Glu Arg Arg Lys Gln Leu Arg Asp Gln Tyr Cys Phe Glu Cys Asp
            250                 255                 260 tgt ttc cgt tgc caa acc cag gac aag gat gct gat atg cta act ggt         929
Cys Phe Arg Cys Gln Thr Gln Asp Lys Asp Ala Asp Met Leu Thr Gly
        265                 270                 275
```

```
gat gag caa gta tgg aag gaa gtt caa gaa tcc ctg aaa aaa att gaa    977
Asp Glu Gln Val Trp Lys Glu Val Gln Glu Ser Leu Lys Lys Ile Glu
    280                 285                 290 gaa ctg aag gca cac tgg aag tgg gag cag gtt ctg gcc atg tgc cag   1025
Glu Leu Lys Ala His Trp Lys Trp Glu Gln Val Leu Ala Met Cys Gln
295                 300                 305                 310 gcg atc ata agc agc aat tct gaa cgg ctt ccc gat atc aac atc tac   1073
Ala Ile Ile Ser Ser Asn Ser Glu Arg Leu Pro Asp Ile Asn Ile Tyr
                315                 320                 325 cag ctg aag gtg ctc gac tgc gcc atg gat gcc tgc atc aac ctc ggc   1121
Gln Leu Lys Val Leu Asp Cys Ala Met Asp Ala Cys Ile Asn Leu Gly
            330                 335                 340 ctg ttg gag gaa gcc ttg ttc tat ggt act cgg acc atg gag cca tac   1169
Leu Leu Glu Glu Ala Leu Phe Tyr Gly Thr Arg Thr Met Glu Pro Tyr
        345                 350                 355 agg att ttt ttc cca gga agc cat ccc gtc aga ggg gtt caa gtg atg   1217
Arg Ile Phe Phe Pro Gly Ser His Pro Val Arg Gly Val Gln Val Met
    360                 365                 370 aaa gtt ggc aaa ctg cag cta cat caa ggc atg ttt ccc caa gca atg   1265
Lys Val Gly Lys Leu Gln Leu His Gln Gly Met Phe Pro Gln Ala Met
375                 380                 385                 390 aag aat ctg aga ctg gct ttt gat att atg aga gtg aca cat ggc aga   1313
Lys Asn Leu Arg Leu Ala Phe Asp Ile Met Arg Val Thr His Gly Arg
                395                 400                 405 gaa cac agc ctg att gaa gat ttg att cta ctt tta gaa gaa tgc gac   1361
Glu His Ser Leu Ile Glu Asp Leu Ile Leu Leu Leu Glu Glu Cys Asp
            410                 415                 420 gcc aac atc aga gca tcc taa gggaacgcag tcagagggaa atacggcgtg      1412
Ala Asn Ile Arg Ala Ser
        425 tgtctttgtt gaatgcctta ttgaggtcac acactctatg ctttgttagc tgtgtgaacc 1472 tctcttattg gaaattctgt tccgtgtttg tgtaggtaaa taaaggcaga catggtttgc 1532 aaaccacaag aatcattagt tgtagagaag cacgattata ataaattcaa acatttggt  1592 tgaggatgcc aaaaaaaaaa aaaaaaaaa                                    1622

<210> SEQ ID NO 2
<211> LENGTH: 428
<212> TYPE: PRT
<213> ORGANISM: Homo sapiens

<400> SEQUENCE: 2

Met Glu Pro Leu Lys Val Glu Lys Phe Ala Thr Ala Asn Arg Gly Asn
1               5                   10                  15

Gly Leu Arg Ala Val Thr Pro Leu Arg Pro Gly Glu Leu Leu Phe Arg
            20                  25                  30

Ser Asp Pro Leu Ala Tyr Thr Val Cys Lys Gly Ser Arg Gly Val Val
        35                  40                  45

Cys Asp Arg Cys Leu Leu Gly Lys Glu Lys Leu Met Arg Cys Ser Gln
    50                  55                  60

Cys Arg Val Ala Lys Tyr Cys Ser Ala Lys Cys Gln Lys Lys Ala Trp
65                  70                  75                  80

Pro Asp His Lys Arg Glu Cys Lys Cys Leu Lys Ser Cys Lys Pro Arg
                85                  90                  95

Tyr Pro Pro Asp Ser Val Arg Leu Leu Gly Arg Val Val Phe Lys Leu
            100                 105                 110

Met Asp Gly Ala Pro Ser Glu Ser Glu Lys Leu Tyr Ser Phe Tyr Asp
        115                 120                 125
```

| Leu | Glu | Ser | Asn | Ile | Asn | Lys | Leu | Thr | Glu | Asp | Lys | Glu | Gly | Leu |
| | 130 | | | | 135 | | | | | 140 | | | | |

| Arg | Gln | Leu | Val | Met | Thr | Phe | Gln | His | Phe | Met | Arg | Glu | Glu | Ile | Gln |
| 145 | | | | | 150 | | | | | 155 | | | | | 160 |

| Asp | Ala | Ser | Gln | Leu | Pro | Pro | Ala | Phe | Asp | Leu | Phe | Glu | Ala | Phe | Ala |
| | | | | 165 | | | | | 170 | | | | | 175 | |

| Lys | Val | Ile | Cys | Asn | Ser | Phe | Thr | Ile | Cys | Asn | Ala | Glu | Met | Gln | Glu |
| | | | | 180 | | | | | 185 | | | | | 190 | |

| Val | Gly | Val | Gly | Leu | Tyr | Pro | Ser | Ile | Ser | Leu | Leu | Asn | His | Ser | Cys |
| | | | 195 | | | | | 200 | | | | | 205 | | |

| Asp | Pro | Asn | Cys | Ser | Ile | Val | Phe | Asn | Gly | Pro | His | Leu | Leu | Leu | Arg |
| | 210 | | | | | 215 | | | | | 220 | | | | |

| Ala | Val | Arg | Asp | Ile | Glu | Val | Gly | Glu | Glu | Leu | Thr | Ile | Cys | Tyr | Leu |
| 225 | | | | | 230 | | | | | 235 | | | | | 240 |

| Asp | Met | Leu | Met | Thr | Ser | Glu | Glu | Arg | Arg | Lys | Gln | Leu | Arg | Asp | Gln |
| | | | | 245 | | | | | 250 | | | | | 255 | |

| Tyr | Cys | Phe | Glu | Cys | Asp | Cys | Phe | Arg | Cys | Gln | Thr | Gln | Asp | Lys | Asp |
| | | | 260 | | | | | 265 | | | | | 270 | | |

| Ala | Asp | Met | Leu | Thr | Gly | Asp | Glu | Gln | Val | Trp | Lys | Gly | Val | Gln | Glu |
| | | 275 | | | | | 280 | | | | | 285 | | | |

| Ser | Leu | Lys | Lys | Ile | Glu | Glu | Leu | Lys | Ala | His | Trp | Lys | Trp | Glu | Gln |
| | 290 | | | | | 295 | | | | | 300 | | | | |

| Val | Leu | Ala | Met | Cys | Gln | Ala | Ile | Ile | Ser | Ser | Asn | Ser | Glu | Arg | Leu |
| 305 | | | | | 310 | | | | | 315 | | | | | 320 |

| Pro | Asp | Ile | Asn | Ile | Tyr | Gln | Leu | Lys | Val | Leu | Asp | Cys | Ala | Met | Asp |
| | | | | 325 | | | | | 330 | | | | | 335 | |

| Ala | Cys | Ile | Asn | Leu | Gly | Leu | Leu | Glu | Glu | Ala | Leu | Phe | Tyr | Gly | Thr |
| | | | 340 | | | | | 345 | | | | | 350 | | |

| Arg | Thr | Met | Glu | Pro | Tyr | Arg | Ile | Phe | Phe | Pro | Gly | Ser | His | Pro | Val |
| | | 355 | | | | | 360 | | | | | 365 | | | |

| Arg | Gly | Val | Gln | Val | Met | Lys | Val | Gly | Lys | Leu | Gln | Leu | His | Gln | Gly |
| | 370 | | | | | 375 | | | | | 380 | | | | |

| Met | Phe | Pro | Gln | Ala | Met | Lys | Asn | Leu | Arg | Leu | Ala | Phe | Asp | Ile | Met |
| 385 | | | | | 390 | | | | | 395 | | | | | 400 |

| Arg | Val | Thr | His | Gly | Arg | Glu | His | Ser | Leu | Ile | Glu | Asp | Leu | Ile | Leu |
| | | | | 405 | | | | | 410 | | | | | 415 | |

| Leu | Leu | Glu | Glu | Cys | Asp | Ala | Asn | Ile | Arg | Ala | Ser |
| | | | 420 | | | | | 425 | | | |

<210> SEQ ID NO 3
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 3
caccaaactt atggatggag cacctttcaa gagaaggtgc tccatccata agttt       55

<210> SEQ ID NO 4
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 4
aaaaaaactt atggatggag caccttctct tgaaaggtgc tccatccata agttt       55

<210> SEQ ID NO 5
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 5
caccaatcag agaagcttta ctcatttcaa gagaatgagt aaagcttata tgatt        55

<210> SEQ ID NO 6
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 6
aaaaaatcag agaagcttta ctcattctct tgaaatgagt aaagcttata tgatt        55

<210> SEQ ID NO 7
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 7
caccaacaaa ctgactgaag ataagttcaa gagaaggtgc tccatccata agttt        55

<210> SEQ ID NO 8
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 8
aaaaaacaaa ctgactgaag ataagtctct tgaaggtgc tccatccata agttt         55

<210> SEQ ID NO 9
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 9
caccaactcg taatgacatt tcaacttcaa gagagttgaa atgtcattac gagtt        55

<210> SEQ ID NO 10
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 10
aaaaaactcg taatgacatt tcaactctct tgaagttgaa atgtcattac gagtt        55

<210> SEQ ID NO 11
<211> LENGTH: 55
<212> TYPE: DNA
<213> ORGANISM: Artificial Sequence
<220> FEATURE:
<223> OTHER INFORMATION: An Artificially Synthesized Sequence

```
<400> SEQUENCE: 11
caccaaaagt gatctgcaac tctttttcaa gagaaaagag ttgcagatca ctttt          55

<210> SEQ ID NO 12
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 12
aaaaaaaagt gatctgcaac tcttttctct tgaaaagag ttgcagatca ctttt           55

<210> SEQ ID NO 13
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 13
caccaagtga tctgcaactc tttcattcaa gagatgaaag agttgcagat cactt          55

<210> SEQ ID NO 14
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 14
aaaaaagtga tctgcaactc tttcatctct tgaatgaaag agttgcagat cactt          55

<210> SEQ ID NO 15
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 15
caccaactct ttcaccatct gtaatttcaa gagaattaca gatggtgaaa gagtt          55

<210> SEQ ID NO 16
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 16
aaaaaactct ttcaccatct gtaattctct tgaaattaca gatggtgaaa gagtt          55

<210> SEQ ID NO 17
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 17
caccaactgt tcgattgtgt tcaatttcaa gagaattgaa cacaatcgaa cagtt          55

<210> SEQ ID NO 18
<211> LENGTH: 55
```

```
<212> TYPE: DNA
<213> ORGANISM: Artificial Sequence
<220> FEATURE:
<223> OTHER INFORMATION: An Artificially Synthesized Sequence

<400> SEQUENCE: 18
aaaaaactgt cgattgtgt tcaattctct tgaaattgaa cacaatcgaa cagtt          55

<210> SEQ ID NO 19
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 19
caccaaggat gctgatatgc taactttcaa gagaagttag catatcagca tcctt          55

<210> SEQ ID NO 20
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 20
aaaaaaggat gctgatatgc taacttctct tgaaagttag catatcagca tcctt          55

<210> SEQ ID NO 21
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 21
caccaactgg tgatgagcaa gtatgttcaa gagacatact tgctcatcac cagtt          55

<210> SEQ ID NO 22
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 22
aaaaaactgg tgatgagcaa gtatgtctct tgaacatact tgctcatcac cagtt          55

<210> SEQ ID NO 23
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 23
caccaagtat ggaaggaagt tcaagttcaa gagacttgaa cttccttcca tactt          55

<210> SEQ ID NO 24
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 24
aaaaaagtat ggaaggaagt tcaagtctct tgaacttgaa cttccttcca tactt          55
```

<210> SEQ ID NO 25
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 25
caccaacatc taccagctga aggtgttcaa gagacacctt cagctggtag atgtt    55

<210> SEQ ID NO 26
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 26
aaaaaacatc taccagctga aggtgtctct tgaacacctt cagctggtag atgtt    55

<210> SEQ ID NO 27
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 27
caccaagcaa tgaagaatct gagacttcaa gagagtctca gattcttcat tgctt    55

<210> SEQ ID NO 28
<211> LENGTH: 55
<212> TYPE: DNA
<213> ORGANISM: Artificial Sequence
<220> FEATURE:
<223> OTHER INFORMATION: An Artificially Synthesized Sequence

<400> SEQUENCE: 28
aaaaaagcaa tgaagaatct gagactctct tgaagtctca gattcttcat tgctt    55

<210> SEQ ID NO 29
<211> LENGTH: 16
<212> TYPE: DNA
<213> ORGANISM: Artificial Sequence
<220> FEATURE:
<223> OTHER INFORMATION: An Artificially Synthesized Antisense
      S-Oligonucleotide Sequence

<400> SEQUENCE: 29
gcgggaggat ggagcc    16

<210> SEQ ID NO 30
<211> LENGTH: 22
<212> TYPE: DNA
<213> ORGANISM: Artificial Sequence
<220> FEATURE:
<223> OTHER INFORMATION: An Artificially Synthesized Primer Sequence

<400> SEQUENCE: 30
acaacagcct caagatcatc ag    22

<210> SEQ ID NO 31
<211> LENGTH: 20
<212> TYPE: DNA
<213> ORGANISM: Artificial Sequence
<220> FEATURE:

<223> OTHER INFORMATION: An Artificially Synthesized Primer Sequence

<400> SEQUENCE: 31
ggtccaccac tgacacgttg                                              20

<210> SEQ ID NO 32
<211> LENGTH: 23
<212> TYPE: DNA
<213> ORGANISM: Artificial Sequence
<220> FEATURE:
<223> OTHER INFORMATION: An Artificially Synthesized Primer Sequence

<400> SEQUENCE: 32
ttcccgatat caacatctac cag                                          23

<210> SEQ ID NO 33
<211> LENGTH: 23
<212> TYPE: DNA
<213> ORGANISM: Artificial Sequence
<220> FEATURE:
<223> OTHER INFORMATION: An Artificially Synthesized Primer Sequence

<400> SEQUENCE: 33
agtgtgtgac ctcaataagg cat                                          23

<210> SEQ ID NO 34
<211> LENGTH: 24
<212> TYPE: DNA
<213> ORGANISM: Artificial Sequence
<220> FEATURE:
<223> OTHER INFORMATION: An Artificially Synthesized Primer Sequence

<400> SEQUENCE: 34
ctgccaagaa gtcggagtct ggag                                         24

<210> SEQ ID NO 35
<211> LENGTH: 32
<212> TYPE: DNA
<213> ORGANISM: Artificial Sequence
<220> FEATURE:
<223> OTHER INFORMATION: An Artificially Synthesized Primer Sequence

<400> SEQUENCE: 35
cggaattcat ggagccgctg aaggtggaaa ag                                32

<210> SEQ ID NO 36
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 36
ccgctcgagg gatgctctga tgttggcgtc g                                 31

<210> SEQ ID NO 37
<211> LENGTH: 64
<212> TYPE: DNA
<213> ORGANISM: Artificial Sequence
<220> FEATURE:
<223> OTHER INFORMATION: An Artificially Synthesized Oligonucleotide
      Sequence
<220> FEATURE:
<221> NAME/KEY: misc_feature
<222> LOCATION: (21)..(40)
<223> OTHER INFORMATION: n is A, G, C or T

<400> SEQUENCE: 37

-continued

```
gggagaattc cgacacgcgt nnnnnnnnnn nnnnnnnnnn ctcgagcgtc tacatggatc    60
ctca                                                                 64
```

<210> SEQ ID NO 38
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 38

```
ggggtaccca gtgctgggaa cgccctctc g                                   31
```

<210> SEQ ID NO 39
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 39

```
ggggtaccca ctcccgccgg agactaggtc c                                  31
```

<210> SEQ ID NO 40
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 40

```
ggggtaccct cgcattctcc tcctcctctg c                                  31
```

<210> SEQ ID NO 41
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 41

```
ggggtacctg gtccctcctc ctcccgccct g                                  31
```

<210> SEQ ID NO 42
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 42

```
ggggtacctc ccgccctgcc tcccgcgcct c                                  31
```

<210> SEQ ID NO 43
<211> LENGTH: 31
<212> TYPE: DNA
<213> ORGANISM: Artificial Sequence
<220> FEATURE:
<223> OTHER INFORMATION: An Artificially Synthesized Primer Sequence

<400> SEQUENCE: 43

```
gaagatctag gtggcctgtc gtccggtctg g                                  31
```

<210> SEQ ID NO 44
<211> LENGTH: 484

```
<212> TYPE: DNA
<213> ORGANISM: Artificial Sequence
<220> FEATURE:
<223> OTHER INFORMATION: An Artificially Synthesized Sequence of the
      psiU6BX6 Plasmid Part1

<400> SEQUENCE: 44
gacggatcgg gagatctccc gatccoctat ggtgcactct cagtacaatc tgctctggat      60
ccactagtaa cggccgccag tgtgctggaa ttcggcttgg ggatcagcgt ttgagtaaga     120
gcccgcgtct gaaccctccg cgccgccccg gccccagtgg aaagacgcgc aggcaaaacg     180
caccacgtga cggagcgtga ccgcgcgccg agcgcgcgcc aaggtcgggc aggaagaggg     240
cctatttccc atgattcctt catatttgca tatacgatac aaggctgtta gagagataat     300
tagaattaat ttgactgtaa acacaaagat attagtacaa atacgtgac gtagaaagta     360 ataatttctt gggtagtttg cagttttaaa attatgtttt aaaatggact atcatatgct     420
taccgtaact tgaaagtatt tcgatttctt ggctttatat atcttgtgga aaggacgaaa     480
cacc                                                                  484

<210> SEQ ID NO 45
<211> LENGTH: 20
<212> TYPE: DNA
<213> ORGANISM: Artificial Sequence
<220> FEATURE:
<223> OTHER INFORMATION: An Artificially Synthesized Primer Sequence

<400> SEQUENCE: 45
ggggatcagc gtttgagtaa                                                  20

<210> SEQ ID NO 46
<211> LENGTH: 20
<212> TYPE: DNA
<213> ORGANISM: Artificial Sequence
<220> FEATURE:
<223> OTHER INFORMATION: An Artificially Synthesized Primer Sequence

<400> SEQUENCE: 46
taggccccac ctccttctat                                                  20

<210> SEQ ID NO 47
<211> LENGTH: 30
<212> TYPE: DNA
<213> ORGANISM: Artificial Sequence
<220> FEATURE:
<223> OTHER INFORMATION: An Artificially Synthesized Primer Sequence

<400> SEQUENCE: 47
tgcggatcca gagcagattg tactgagagt                                       30

<210> SEQ ID NO 48
<211> LENGTH: 29
<212> TYPE: DNA
<213> ORGANISM: Artificial Sequence
<220> FEATURE:
<223> OTHER INFORMATION: An Artificially Synthesized Primer Sequence

<400> SEQUENCE: 48
ctctatctcg agtgaggcgg aaagaacca                                        29

<210> SEQ ID NO 49
<211> LENGTH: 40
<212> TYPE: DNA
<213> ORGANISM: Artificial Sequence
<220> FEATURE:
```

-continued

<223> OTHER INFORMATION: An Artificially Synthesized Primer Sequence

<400> SEQUENCE: 49
tttaagcttg aagactattt ttacatcagg ttgtttttct                40

<210> SEQ ID NO 50
<211> LENGTH: 37
<212> TYPE: DNA
<213> ORGANISM: Artificial Sequence
<220> FEATURE:
<223> OTHER INFORMATION: An Artificially Synthesized Primer Sequence

<400> SEQUENCE: 50
tttaagcttg aagacacggt gtttcgtcct ttccaca                37

<210> SEQ ID NO 51
<211> LENGTH: 51
<212> TYPE: DNA
<213> ORGANISM: Artificial Sequence
<220> FEATURE:
<223> OTHER INFORMATION: An Artificially Synthesized Oligonucleotide
      Sequence

<400> SEQUENCE: 51
caccgaagca gcacgacttc ttcttcaaga gagaagaagt cgtgctgctt c                51

<210> SEQ ID NO 52
<211> LENGTH: 51
<212> TYPE: DNA
<213> ORGANISM: Artificial Sequence
<220> FEATURE:
<223> OTHER INFORMATION: An Artificially Synthesized Oligonucleotide
      Sequence

<400> SEQUENCE: 52
aaaagaagca gcacgacttc ttctctcttg aagaagaagt cgtgctgctt c                51

<210> SEQ ID NO 53
<211> LENGTH: 30
<212> TYPE: DNA
<213> ORGANISM: Artificial Sequence
<220> FEATURE:
<223> OTHER INFORMATION: An Artificially Synthesized Primer Sequence

<400> SEQUENCE: 53
ggggtaccag gatggagccg ctgaaggtgg                30

<210> SEQ ID NO 54
<211> LENGTH: 33
<212> TYPE: DNA
<213> ORGANISM: Artificial Sequence
<220> FEATURE:
<223> OTHER INFORMATION: An Artificially Synthesized Primer Sequence

<400> SEQUENCE: 54
gggaattctt aggatgctct gatgttggcg tcg                33

<210> SEQ ID NO 55
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 55
aaacttatgg atggagcacc tttcaagaga aggtgctcca tccataagtt t                51

<210> SEQ ID NO 56
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 56
aatcagagaa gctttactca tttcaagaga atgagtaaag cttctctgat t          51

<210> SEQ ID NO 57
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 57
aacaaactga ctgaagataa gttcaagaga cttatcttca gtcagtttgt t          51

<210> SEQ ID NO 58
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 58
aactcgtaat gacatttcaa cttcaagaga gttgaaatgt cattacgagt t          51

<210> SEQ ID NO 59
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 59
aaaagtgatc tgcaactctt tttcaagaga aaagagttgc agatcacttt t          51

<210> SEQ ID NO 60
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 60
aagtgatctg caactctttc attcaagaga tgaaagagtt gcagatcact t          51

<210> SEQ ID NO 61
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 61
aactctttca ccatctgtaa tttcaagaga attacagatg gtgaaagagt t          51

<210> SEQ ID NO 62
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 62
aactgttcga ttgtgttcaa tttcaagaga attgaacaca atcgaacagt t          51

<210> SEQ ID NO 63
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 63
aaggatgctg atatgctaac tttcaagaga agttagcata tcagcatcct t          51

<210> SEQ ID NO 64
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 64
aactggtgat gagcaagtat gttcaagaga catacttgct catcaccagt t          51

<210> SEQ ID NO 65
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 65
aagtatggaa ggaagttcaa gttcaagaga cttgaacttc cttccatact t          51

<210> SEQ ID NO 66
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 66
aacatctacc agctgaaggt gttcaagaga caccttcagc tggtagatgt t          51

<210> SEQ ID NO 67
<211> LENGTH: 51
<212> TYPE: DNA
<213> ORGANISM: Artificial Sequence
<220> FEATURE:
<223> OTHER INFORMATION: An Artificially Synthesized Hairpin siRNA
      Sequence

<400> SEQUENCE: 67
aagcaatgaa gaatctgaga cttcaagaga gtctcagatt cttcattgct t          51

<210> SEQ ID NO 68
<211> LENGTH: 21

```
<212> TYPE: DNA
<213> ORGANISM: Artificial Sequence
<220> FEATURE:
<223> OTHER INFORMATION: An Artificially Synthesized Target Sequence for
      siRNA

<400> SEQUENCE: 68
aaacttatgg atggagcacc t                                              21

<210> SEQ ID NO 69
<211> LENGTH: 21
<212> TYPE: DNA
<213> ORGANISM: Artificial Sequence
<220> FEATURE:
<223> OTHER INFORMATION: An Artificially Synthesized Target Sequence for
      siRNA

<400> SEQUENCE: 69
aatcagagaa gctttactca t                                              21

<210> SEQ ID NO 70
<211> LENGTH: 21
<212> TYPE: DNA
<213> ORGANISM: Artificial Sequence
<220> FEATURE:
<223> OTHER INFORMATION: An Artificially Synthesized Target Sequence

<400> SEQUENCE: 70
aacaaactga ctgaagataa g                                              21

<210> SEQ ID NO 71
<211> LENGTH: 21
<212> TYPE: DNA
<213> ORGANISM: Artificial Sequence
<220> FEATURE:
<223> OTHER INFORMATION: An Artificially Synthesized Target Sequence

<400> SEQUENCE: 71
aactcgtaat gacatttcaa c                                              21

<210> SEQ ID NO 72
<211> LENGTH: 21
<212> TYPE: DNA
<213> ORGANISM: Artificial Sequence
<220> FEATURE:
<223> OTHER INFORMATION: An Artificially Synthesized Target Sequence

<400> SEQUENCE: 72
aaaagtgatc tgcaactctt t                                              21

<210> SEQ ID NO 73
<211> LENGTH: 21
<212> TYPE: DNA
<213> ORGANISM: Artificial Sequence
<220> FEATURE:
<223> OTHER INFORMATION: An Artificially Synthesized Target Sequence

<400> SEQUENCE: 73
aagtgatctg caactctttc a                                              21

<210> SEQ ID NO 74
<211> LENGTH: 21
<212> TYPE: DNA
<213> ORGANISM: Artificial Sequence
<220> FEATURE:
<223> OTHER INFORMATION: An Artificially Synthesized Target Sequence

<400> SEQUENCE: 74
```

```
aactctttca ccatctgtaa t                                              21

<210> SEQ ID NO 75
<211> LENGTH: 21
<212> TYPE: DNA
<213> ORGANISM: Artificial Sequence
<220> FEATURE:
<223> OTHER INFORMATION: An Artificially Synthesized Target Sequence

<400> SEQUENCE: 75
aactgttcga ttgtgttcaa t                                              21

<210> SEQ ID NO 76
<211> LENGTH: 21
<212> TYPE: DNA
<213> ORGANISM: Artificial Sequence
<220> FEATURE:
<223> OTHER INFORMATION: An Artificially Synthesized Target Sequence

<400> SEQUENCE: 76
aaggatgctg atatgctaac t                                              21

<210> SEQ ID NO 77
<211> LENGTH: 21
<212> TYPE: DNA
<213> ORGANISM: Artificial Sequence
<220> FEATURE:
<223> OTHER INFORMATION: An Artificially Synthesized Target Sequence

<400> SEQUENCE: 77
aactggtgat gagcaagtat g                                              21

<210> SEQ ID NO 78
<211> LENGTH: 21
<212> TYPE: DNA
<213> ORGANISM: Artificial Sequence
<220> FEATURE:
<223> OTHER INFORMATION: An Artificially Synthesized Target Sequence

<400> SEQUENCE: 78
aagtatggaa ggaagttcaa g                                              21

<210> SEQ ID NO 79
<211> LENGTH: 21
<212> TYPE: DNA
<213> ORGANISM: Artificial Sequence
<220> FEATURE:
<223> OTHER INFORMATION: An Artificially Synthesized Target Sequence

<400> SEQUENCE: 79
aacatctacc agctgaaggt g                                              21

<210> SEQ ID NO 80
<211> LENGTH: 21
<212> TYPE: DNA
<213> ORGANISM: Artificial
<220> FEATURE:
<223> OTHER INFORMATION: An artificially Synthesized Target Sequence

<400> SEQUENCE: 80
aagcaatgaa gaatctgaga c                                              21

<210> SEQ ID NO 81
<211> LENGTH: 403
<212> TYPE: PRT
<213> ORGANISM: Artificial Sequence
```

-continued

```
<220> FEATURE:
<223> OTHER INFORMATION: Homologous sequence of SEQ ID NO:1 and SEQ ID
      NO:82

<400> SEQUENCE: 81

Met Glu Leu Lys Val Glu Lys Phe Thr Ala Asn Arg Gly Asn Gly Leu
1               5                   10                  15

Arg Ala Val Pro Leu Arg Pro Gly Glu Leu Leu Phe Arg Ser Asp Pro
                20                  25                  30

Leu Ala Tyr Thr Val Cys Lys Gly Ser Arg Gly Val Cys Asp Arg
            35                  40                  45

Cys Leu Leu Gly Lys Glu Lys Leu Met Arg Cys Ser Gln Cys Arg Ala
    50                  55                  60

Lys Tyr Cys Ser Ala Lys Cys Gln Lys Lys Ala Trp Pro Asp His Arg
65                  70                  75                  80

Glu Cys Cys Leu Lys Ser Cys Lys Pro Arg Tyr Pro Pro Asp Ser Val
                85                  90                  95

Arg Leu Leu Gly Arg Val Lys Leu Met Asp Pro Ser Glu Ser Glu Lys
                100                 105                 110

Leu Tyr Ser Phe Tyr Asp Leu Glu Ser Asn Ile Lys Leu Thr Glu Asp
            115                 120                 125

Lys Lys Glu Gly Leu Arg Gln Leu Met Thr Phe Gln His Phe Met Arg
    130                 135                 140

Glu Glu Ile Gln Asp Ala Ser Gln Leu Pro Pro Phe Asp Leu Phe Glu
145                 150                 155                 160

Ala Phe Ala Lys Val Ile Cys Asn Ser Phe Thr Ile Cys Asn Ala Glu
                165                 170                 175

Met Gln Glu Val Gly Val Gly Leu Tyr Pro Ser Ser Leu Leu Asn His
                180                 185                 190

Ser Cys Asp Pro Asn Cys Ser Ile Val Phe Asn Gly Pro His Leu Leu
            195                 200                 205

Leu Arg Ala Val Arg Ile Glu Gly Glu Leu Thr Ile Cys Tyr Leu
    210                 215                 220

Asp Met Leu Met Thr Ser Glu Glu Arg Arg Lys Gln Leu Arg Asp Gln
225                 230                 235                 240

Tyr Cys Phe Glu Cys Asp Cys Arg Cys Gln Thr Gln Asp Lys Asp Ala
                245                 250                 255

Asp Met Leu Thr Gly Asp Glu Gln Trp Lys Glu Val Gln Glu Ser Leu
                260                 265                 270

Lys Lys Ile Glu Glu Leu Lys Ala His Trp Lys Trp Glu Gln Val Leu
            275                 280                 285

Ala Cys Gln Ala Ile Ile Ser Asn Ser Arg Leu Pro Asp Ile Asn Ile
    290                 295                 300

Tyr Gln Leu Lys Val Leu Asp Cys Ala Met Asp Ala Cys Ile Asn Leu
305                 310                 315                 320

Gly Leu Glu Glu Ala Leu Phe Tyr Arg Thr Met Glu Pro Tyr Arg Ile
                325                 330                 335

Phe Phe Pro Gly Ser His Pro Val Arg Gly Val Gln Val Met Lys Val
                340                 345                 350

Gly Lys Leu Gln Leu His Gln Gly Met Phe Pro Gln Ala Met Lys Asn
            355                 360                 365

Leu Arg Leu Ala Phe Asp Ile Met Val Thr His Gly Arg Glu His Ser
    370                 375                 380

Leu Ile Glu Asp Leu Ile Leu Leu Glu Glu Cys Asp Ala Asn Ile
385                 390                 395                 400
```

Arg Ala Ser

<210> SEQ ID NO 82
<211> LENGTH: 428
<212> TYPE: PRT
<213> ORGANISM: Homo sapiens

<400> SEQUENCE: 82

Met Glu Ala Leu Lys Val Glu Lys Phe Thr Thr Ala Asn Arg Gly Asn
1               5                   10                  15

Gly Leu Arg Ala Val Ala Pro Leu Arg Pro Gly Glu Leu Leu Phe Arg
            20                  25                  30

Ser Asp Pro Leu Ala Tyr Thr Val Cys Lys Gly Ser Arg Gly Val Val
        35                  40                  45

Cys Asp Arg Cys Leu Leu Gly Lys Glu Lys Leu Met Arg Cys Ser Gln
    50                  55                  60

Cys Arg Ile Ala Lys Tyr Cys Ser Ala Lys Cys Gln Lys Lys Ala Trp
65                  70                  75                  80

Pro Asp His Arg Arg Glu Cys Ser Cys Leu Lys Ser Cys Lys Pro Arg
                85                  90                  95

Tyr Pro Pro Asp Ser Val Arg Leu Leu Gly Arg Val Ile Val Lys Leu
            100                 105                 110

Met Asp Glu Lys Pro Ser Glu Ser Glu Lys Leu Tyr Ser Phe Tyr Asp
        115                 120                 125

Leu Glu Ser Asn Ile Ser Lys Leu Thr Glu Asp Lys Lys Glu Gly Leu
    130                 135                 140

Arg Gln Leu Ala Met Thr Phe Gln His Phe Met Arg Glu Glu Ile Gln
145                 150                 155                 160

Asp Ala Ser Gln Leu Pro Pro Ser Phe Asp Leu Phe Glu Ala Phe Ala
                165                 170                 175

Lys Val Ile Cys Asn Ser Phe Thr Ile Cys Asn Ala Glu Met Gln Glu
            180                 185                 190

Val Gly Val Gly Leu Tyr Pro Ser Met Ser Leu Leu Asn His Ser Cys
        195                 200                 205

Asp Pro Asn Cys Ser Ile Val Phe Asn Gly Pro His Leu Leu Leu Arg
    210                 215                 220

Ala Val Arg Glu Ile Glu Ala Gly Glu Glu Leu Thr Ile Cys Tyr Leu
225                 230                 235                 240

Asp Met Leu Met Thr Ser Glu Glu Arg Arg Lys Gln Leu Arg Asp Gln
                245                 250                 255

Tyr Cys Phe Glu Cys Asp Cys Ile Arg Cys Gln Thr Gln Asp Lys Asp
            260                 265                 270

Ala Asp Met Leu Thr Gly Asp Glu Gln Ile Trp Lys Glu Val Gln Glu
        275                 280                 285

Ser Leu Lys Lys Ile Glu Glu Leu Lys Ala His Trp Lys Trp Glu Gln
    290                 295                 300

Val Leu Ala Leu Cys Gln Ala Ile Ile Asn Ser Asn Ser Asn Arg Leu
305                 310                 315                 320

Pro Asp Ile Asn Ile Tyr Gln Leu Lys Val Leu Asp Cys Ala Met Asp
                325                 330                 335

Ala Cys Ile Asn Leu Gly Met Leu Glu Glu Ala Leu Phe Tyr Ala Met
            340                 345                 350

Arg Thr Met Glu Pro Tyr Arg Ile Phe Phe Pro Gly Ser His Pro Val
        355                 360                 365

```
Arg Gly Val Gln Val Met Lys Val Gly Lys Leu Gln Leu His Gln Gly
            370                 375                 380

Met Phe Pro Gln Ala Met Lys Asn Leu Arg Leu Ala Phe Asp Ile Met
385                 390                 395                 400

Lys Val Thr His Gly Arg Glu His Ser Leu Ile Glu Asp Leu Ile Leu
                405                 410                 415

Leu Leu Glu Glu Cys Asp Ala Asn Ile Arg Ala Ser
            420                 425

<210> SEQ ID NO 83
<211> LENGTH: 30
<212> TYPE: DNA
<213> ORGANISM: Artificial Sequence
<220> FEATURE:
<223> OTHER INFORMATION: An Artificially Synthesized Oligonucleotide
      Sequence

<400> SEQUENCE: 83
gcgggaggat ggagccgctg aaggtggaaa                                     30

<210> SEQ ID NO 84
<211> LENGTH: 4378
<212> TYPE: DNA
<213> ORGANISM: Artificial Sequence
<220> FEATURE:
<223> OTHER INFORMATION: An Artificially Synthesized Sequence of the
      psiU6BX6 Plasmid Part2

<400> SEQUENCE: 84 ttttacatc aggttgtttt tctgtttggt tttttttta caccacgttt atacgccggt       60
gcacggttta ccactgaaaa cacctttcat ctacaggtga tatcttttaa cacaaataaa   120
atgtagtagt cctaggagac ggaatagaag gaggtggggc ctaaagccga attctgcaga   180
tatccatcac actggcggcc gctcgagtga ggcggaaaga accagctggg gctctagggg   240
gtatccccac gcgccctgta gcggcgcatt aagcgcggcg ggtgtggtgg ttacgcgcag   300
cgtgaccgct acacttgcca gcgccctagc gcccgctcct ttcgctttct tcccttcctt   360
tctcgccacg ttcgccggct ttccccgtca gctctaaat cggggctcc ctttaggggtt   420 ccgatttagt gctttacggc acctcgaccc caaaaaactt gattagggtg atggttcacg   480
tagtgggcca tcgccctgat agacggtttt tcgccctttg acgttggagt ccacgttctt   540
taatagtgga ctcttgttcc aaactggaac aacactcaac cctatctcgg tctattcttt   600
tgatttataa gggattttgc cgatttcggc ctattggtta aaaaatgagc tgatttaaca   660
aaaatttaac gcgaattaat ctgtggaat gtgtgtcagt tagggtgtgg aaagtcccca   720
ggctccccag caggcagaag tatgcaaagc atgcatctca attagtcagc aaccaggtgt   780
ggaaagtccc caggctcccc agcaggcaga agtatgcaaa gcatgcatct caattagtca   840
gcaaccatag tcccgcccct aactccgccc atcccgcccc taactccgcc cagttccgcc   900
cattctccgc cccatggctg actaattttt tttatttatg cagaggccga ggccgcctct   960
gcctctgagc tattccagaa gtagtgagga ggcttttttg gaggcctagg cttttgcaaa  1020
aagctcccgg gagcttgtat atccattttc ggatctgatc aagagacagg atgaggatcg  1080
tttcgcatga ttgaacaaga tggattgcac gcaggttctc cggccgcttg ggtggagagg  1140
ctattcggct atgactgggc acaacagaca atcggctgct ctgatgccgc cgtgttccgg  1200
ctgtcagcgc aggggcgccc ggttcttttt gtcaagaccg acctgtccgg tgccctgaat  1260
gaactgcagg acgaggcagc gcggctatcg tggctggcca cgacgggcgt tccttgcgca  1320
```

```
gctgtgctcg acgttgtcac tgaagcggga agggactggc tgctattggg cgaagtgccg    1380
gggcaggatc tcctgtcatc tcaccttgct cctgccgaga agtatccat catggctgat     1440 gcaatgcggc ggctgcatac gcttgatccg gctacctgcc cattcgacca ccaagcgaaa    1500
catcgcatcg agcgagcacg tactcggatg gaagccggtc ttgtcgatca ggatgatctg    1560
gacgaagagc atcaggggct cgcgccagcc gaactgttcg ccaggctcaa ggcgcgcatg    1620
cccgacggcg aggatctcgt cgtgacccat ggcgatgcct gcttgccgaa tatcatggtg    1680
gaaaatggcc gcttttctgg attcatcgac tgtggccggc tgggtgtggc ggaccgctat    1740
caggacatag cgttggctac ccgtgatatt gctgaagagc ttggcggcga atgggctgac    1800
cgcttcctcg tgctttacgg tatcgccgct cccgattcgc agcgcatcgc cttctatcgc    1860
cttcttgacg agttcttctg agcgggactc tggggttcga atgaccgac caagcgacgc     1920 ccaacctgcc atcacgagat ttcgattcca ccgccgcctt ctatgaaagg ttgggcttcg    1980
gaatcgtttt ccgggacgcc ggctggatga tcctccagcg cggggatctc atgctggagt    2040
tcttcgccca ccccaacttg tttattgcag cttataatgg ttacaaataa agcaaagcat    2100
cacaaatttc acaaataaag catttttttc actgcattct agttgtggtt tgtccaaact    2160
catcaatgta tcttatcatg tctgtatacc gtcgacctct agctagagct tggcgtaatc    2220
atggtcatag ctgtttcctg tgtgaaattg ttatccgctc acaattccac acaacatacg    2280
agccggaagc ataaagtgta aagcctgggg tgcctaatga gtgagctaac tcacattaat    2340
tgcgttgcgc tcactgcccg ctttccagtc gggaaacctg tcgtgccagc tgcattaatg    2400
aatcggccaa cgcgcgggga gaggcggttt gcgtattggg cgctcttccg cttcctcgct    2460
cactgactcg ctgcgctcgg tcgttcggct gcggcgagcg gtatcagctc actcaaaggc    2520
ggtaatacgg ttatccacag aatcagggga taacgcagga agaacatgt gagcaaaagg     2580 ccagcaaaag gccaggaacc gtaaaaaggc cgcgttgctg cgttttttcc ataggctccg    2640
cccccctgac gagcatcaca aaaatcgacg ctcaagtcag aggtggcgaa acccgacagg    2700
actataaaga taccaggcgt ttccccctgg aagctccctc gtgcgctctc ctgttccgac    2760
cctgccgctt accggatacc tgtccgcctt tctcccttcg ggaagcgtgg cgctttctca    2820
tagctcacgc tgtaggtatc tcagttcggt gtaggtcgtt cgctccaagc tgggctgtgt    2880
gcacgaaccc cccgttcagc ccgaccgctg cgccttatcc ggtaactatc gtcttgagtc    2940
caacccggta agacacgact tatcgccact ggcagcagcc actggtaaca ggattagcag    3000
agcgaggtat gtaggcggtg ctacagagtt cttgaagtgg tggcctaact acggctacac    3060
tagaagaaca gtatttggta tctgcgctct gctgaagcca gttaccttcg gaaaaagagt    3120
tggtagctct tgatccggca aacaaaccac cgctggtagc ggtttttttg tttgcaagca    3180
gcagattacg cgcagaaaaa aaggatctca agaagatcct ttgatctttt ctacggggtc    3240
tgacgctcag tggaacgaaa actcacgtta agggattttg gtcatgagat tatcaaaaag    3300
gatcttcacc tagatccttt taaattaaaa atgaagtttt aaatcaatct aaagtatata    3360
tgagtaaact tggtctgaca gttaccaatg cttaatcagt gaggcaccta tctcagcgat    3420
ctgtctattt cgttcatcca tagttgcctg actccccgtc gtgtagataa ctacgatacg    3480
ggagggctta ccatctggcc ccagtgctgc aatgataccg cgagacccac gctcaccggc    3540
tccagattta tcagcaataa accagccagc cggaagggcc gagcgcagaa gtggtcctgc    3600
aactttatcc gcctccatcc agtctattaa ttgttgccgg gaagctagag taagtagttc    3660
gccagttaat agtttgcgca acgttgttgc cattgctaca ggcatcgtgg tgtcacgctc    3720
```

```
-continued
gtcgtttggt atggcttcat tcagctccgg ttcccaacga tcaaggcgag ttacatgatc    3780
ccccatgttg tgcaaaaaag cggttagctc cttcggtcct ccgatcgttg tcagaagtaa    3840
gttggccgca gtgttatcac tcatggttat ggcagcactg cataattctc ttactgtcat    3900
gccatccgta agatgctttt ctgtgactgg tgagtactca accaagtcat tctgagaata    3960
gtgtatgcgg cgaccgagtt gctcttgccc ggcgtcaata cgggataata ccgcgccaca    4020
tagcagaact ttaaaagtgc tcatcattgg aaaacgttct tcggggcgaa aactctcaag    4080
gatcttaccg ctgttgagat ccagttcgat gtaacccact cgtgcaccca actgatcttc    4140
agcatctttt actttcacca gcgtttctgg gtgagcaaaa acaggaaggc aaaatgccgc    4200
aaaaaaggga ataagggcga cacggaaatg ttgaatactc atactcttcc tttttcaata    4260
ttattgaagc atttatcagg gttattgtct catgagcgga tacatatttg aatgtattta    4320
gaaaaataaa caaatagggg ttccgcgcac atttccccga aaagtgccac ctgacgtc     4378
```